US008784829B2

(12) United States Patent
Morsey et al.

(10) Patent No.: US 8,784,829 B2
(45) Date of Patent: Jul. 22, 2014

(54) LAWSONIA INTRACELLULARIS VACCINES

(75) Inventors: Mohamad A. Morsey, Elkhorn, NE (US); Stephanie M. Cook, Elkhorn, NE (US); Yuanzheng Zhang, Elkhorn, NE (US); Qing Zhang, Short Hills, NJ (US)

(73) Assignee: Intervet Inc., Summit, NJ (US)

( * ) Notice: Subject to any disclaimer, the term of this patent is extended or adjusted under 35 U.S.C. 154(b) by 277 days.

(21) Appl. No.: 13/125,019

(22) PCT Filed: Oct. 21, 2009

(86) PCT No.: PCT/US2009/061429
§ 371 (c)(1),
(2), (4) Date: Apr. 19, 2011

(87) PCT Pub. No.: WO2010/048252
PCT Pub. Date: Apr. 29, 2010

(65) Prior Publication Data
US 2011/0200631 A1 Aug. 18, 2011

Related U.S. Application Data

(60) Provisional application No. 61/107,858, filed on Oct. 23, 2008.

(51) Int. Cl.
*A61K 39/02* (2006.01)
*A61K 39/00* (2006.01)
*A61K 39/38* (2006.01)
*A61K 38/00* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl.
USPC .................. 424/190.1; 424/184.1; 424/185.1; 530/300

(58) Field of Classification Search
CPC . A61K 39/105; A61K 2039/02; A61K 39/00; A61K 2039/00
See application file for complete search history.

(56) References Cited

U.S. PATENT DOCUMENTS

| 5,414,085 | A | 5/1995 | Buechler |
| 5,580,859 | A | 12/1996 | Felgner et al. |
| 5,589,466 | A | 12/1996 | Felgner et al. |
| 5,679,647 | A | 10/1997 | Carson et al. |
| 5,736,524 | A | 4/1998 | Content et al. |
| 5,739,118 | A | 4/1998 | Carrano et al. |
| 5,804,566 | A | 9/1998 | Carson et al. |
| 5,922,687 | A | 7/1999 | Mann et al. |
| 2006/0024696 | A1* | 2/2006 | Kapur et al. ............. 435/6 |
| 2011/0129500 | A1 | 6/2011 | Biermann et al. |

FOREIGN PATENT DOCUMENTS

| JP | 2006-501846 | 1/2006 |
| WO | WO 98/04720 | 2/1998 |
| WO | WO 99/15636 | 4/1999 |
| WO | WO 2004/033631 | 4/2004 |
| WO | 2005/070958 A2 | 8/2005 |
| WO | WO 2006/116763 | 11/2006 |

OTHER PUBLICATIONS

Oke, 2011, Monitoring and preventing equine proliferative enteropathy, http://www.bloodhorse.com/horse-racing/articles/63560/monitoring-and-preventing-equine-proliferative-enteropathy.*
Sjolander et al., Journal of Leukocyte Biology, 1998; 64: 713-723.*
Stills, ILAR Journal, 2005; 46(3): 280-293.*
Altschul, Stephen F. et al. "Basic Local Alignment Search Tool", J. Mol Biol. (1990) 215:403-410.
Altschul, Stephen F. et al. "Gapped Blast and PSI-Blast: A New Generation of Protein Database Search Programs", Nucleic Acids Research (1997) 25(17):3389-3402.
Henikoff, Steven and Henikoff, Jorja G. "Amino Acid Substitution Matrices from Protein Blocks", Proc. Nat'l. Acad. Sci. USA (Nov. 1992) 89:10915-10919.
Karlin, Samuel and Altschul, Stephen F. "Applications and Statistics for Multiple High-Scoring Segments in Molecular Sequences", Proc. Nat'l. Acad. Sci. USA (Jun. 1993) 90:5873-5877.
Lawson, G.H.K. et al. "Intracellular Bacteria of Porcine Proliferative Enteropathy: Cultivation and Maintenance In Vitro", Journal of Clinical Microbiology (May 1993) 31(5):1136-1142.
McOrist, Steven et al. "Characterization of *Lawsonia intracellularis* gen. nov., sp. nov., the Obligately Intracellular Bacterium of Porcine Proliferative Enteropathy", International Journal of Systematic Bacteriology (Oct. 1995) 45(4):820-825.

(Continued)

*Primary Examiner* — Vanessa L. Ford
*Assistant Examiner* — Lakia Tongue

(57) ABSTRACT

The present invention relates to polynucleotide sequences encoding novel *Lawsonia intracellularis* polypeptides. It also relates to DNA fragments, recombinant plasmid DNA and live recombinant microorganisms comprising these sequences. Moreover, the invention relates to polypeptides encoded by these nucleotide sequences. The invention also relates to immunogenic compositions for prevention of *Lawsonia intracellularis* infections and methods for the preparation of these immunogenic compositions. The invention also relates to diagnostic tests for the detection of *Lawsonia intracellularis* DNA, the detection of *Lawsonia intracellularis* antigens and detection of antibodies against *Lawsonia intracellularis*.

16 Claims, No Drawings

(56) References Cited

OTHER PUBLICATIONS

McOrist, Steven et al. "Evaluation of Porcine Ileum Models of Enterocyte Infection by *Lawsonia intracellularis*", The Canadian Journal of Veterinary Research (2006) 70:155-159.

Morein, B. et al. "Iscom, a Novel Structure for Antigenic Presentation of Membrane Proteins from Enveloped Viruses", Nature (Mar. 1984) 308:457-460.

Needleman, Saul B. and Wunsch, Christian D. "A General Method Applicable to the Search for Similarities in the Amino Acid Sequence of Two Proteins", J. Mol. Biol. (1970) 48:443-453.

Pearson, William R. and Lipman, David J. "Improved Tools for Biological Sequence Comparison", Proc. Nat'l. Acad. Sci. USA (Apr. 1998) 85:2444-2448.

Wolff, Jon A. et al. "Direct Gene Transfer into Mouse Muscle in Vivo", Science (1990) 247:1465-1468.

International Search Report corresponding to PCT/US2009/061429, mailed Mar. 16, 2010.

* cited by examiner

```
                        SEQUENCE LISTING

<160> NUMBER OF SEQ ID NOS: 67

<210> SEQ ID NO 1
<211> LENGTH: 806
<212> TYPE: PRT
<213> ORGANISM: Lawsonia intracellularis

<400> SEQUENCE: 1

Leu Tyr Asn Leu Phe Leu Pro Phe Ile Leu Thr Asn Leu Ile Tyr Tyr
1               5                   10                  15

Ile Ile Ile Pro Ser Leu Phe Ile Ala Phe Phe Pro Leu Gln Ala Leu
            20                  25                  30

Ser Ile Ile Asn Ile Ser Glu Phe Ala Gln Pro Asp Ile Asn Gln Ser
            35                  40                  45

Gln Thr Lys Trp Asn Leu Glu Ala Asp Thr Leu Thr Leu Ser Asn
    50                  55                  60

Asn Thr Ile Ile Glu Ala Lys Gly Asn Ile Ile Leu Thr Lys Gly Gln
65                  70                  75                  80

Asp Val Phe Lys Ala Asp Phe Ala Arg Tyr Tyr Gln Lys Thr Gly Trp
                85                  90                  95

Leu Phe Leu Lys Gly His Val Thr Val Lys Met Asp Glu Asn Glu Ile
                100                 105                 110

Asn Ala Asp Glu Ala Glu Phe Asn Leu Asn Thr Lys Thr Gly Trp Leu
            115                 120                 125

Asn Asn Gly Asn Ile Phe Ile Ser Ser Ser His Val Tyr Phe Ser Gly
        130                 135                 140

Ala Arg Ile Thr Lys His Tyr Gly Asp Tyr Tyr Thr Phe Asn Asn Val
145                 150                 155                 160

Lys Val Thr Thr Cys Asp Gly Pro His Pro Ala Trp Ser Ile Ser Ala
                165                 170                 175

Lys Glu Ala Ile Val Glu Val Asp Gly Tyr Ala Gln Leu Tyr Asp Ser
                180                 185                 190

Thr Phe Lys Ile Lys Asn Ile Asp Val Met Tyr Ser Pro Ile Phe Thr
            195                 200                 205

Ile Pro Ala Lys Gln Thr Arg Gln Ser Gly Phe Leu Asn Pro Asn Tyr
    210                 215                 220

Gly Ile Ser Gln Arg Arg Gly Ile Tyr Tyr Thr Gln Pro Tyr Phe Leu
225                 230                 235                 240

Asn Ile Asp Gln Ser Ser Asp Leu Thr Phe Tyr Ala Gly Leu Met Thr
                245                 250                 255

Lys Ile Gly Pro Leu Gly Thr Val Arg Tyr Arg Ser His Lys Phe Thr
                260                 265                 270

Asn Gln Lys Thr Trp Phe Ala Ala Ser Gly Ile His Asp Lys Asn Asn
            275                 280                 285

Ile Val Thr Pro Gly Lys Asp Pro Val Tyr Pro Ser Ser Gln Leu Val
    290                 295                 300

Arg Asn Asn His Gln Arg Tyr Trp Val Arg Gly Met Ala Asp Gly Phe
305                 310                 315                 320

Ile Gly Asn Ser Thr Trp Cys Tyr Ile Ser Asn Leu Asp Tyr Val Ser
                325                 330                 335
```

-continued

```
Asp Gln Asp Tyr Leu Arg Glu Phe Asp Gln Gly Ile Thr Gly Phe Ser
            340                 345                 350
His Ser Arg Ser Glu Met Phe Gln Met Phe Gly Arg Asp Ile Gln Glu
                355                 360                 365
Asp Asp Gln Ser Arg Leu Asn Ala Leu Leu Ile Arg Lys Asp Trp Gln
370                 375                 380
Arg Ile Gly Val Val Gly Asn Ile Arg Tyr Glu Gln Asp Pro Thr Leu
385                 390                 395                 400
Gly His Gly Asn His Pro Thr Ser Gln Ser Glu Leu Thr Gln Arg Ile
                405                 410                 415
Pro Gln Ile Asp Met Phe Leu Tyr Gln Gly Lys Leu Phe Gln Pro Leu
            420                 425                 430
Ser Leu Glu Gly Ala Ile His Leu Gln Ser Ala Tyr Met Tyr Arg Ala
            435                 440                 445
Lys Gly Thr Lys Gly Trp Arg Thr Glu Leu Tyr Pro Lys Val Thr Leu
            450                 455                 460
Pro Ile Asp Leu Lys Tyr Gly Ser Val Ile Thr Thr Val Gly Leu Arg
465                 470                 475                 480
Glu Thr Tyr Tyr Gln Thr Gly Ile Lys Ser His Thr Ser Pro Val Ala
                485                 490                 495
Pro His Val Pro Asp Thr Lys Thr Pro Arg Gln Thr Gly Gln His Arg
            500                 505                 510
Ser Leu Phe Asn Leu Gln Leu Glu Ser Ser Thr Gln Ala His Arg Ile
            515                 520                 525
Trp Arg Leu Lys Asp Lys Lys Thr Ile Asn Leu His Ser Gln Ser Ile
530                 535                 540
Gly Lys Thr Phe Cys Thr Ala Leu Lys His Thr Ile Gln Pro Arg Ile
545                 550                 555                 560
Cys Tyr Ser Phe Ile Pro Arg Glu Gly Gln Glu Lys Asn Pro Phe Tyr
                565                 570                 575
Thr Leu Ser Asp Arg Ile Leu Pro Gln Asn Asp Leu Thr Tyr Ser Ile
            580                 585                 590
Val Asn Ile Leu Thr Lys Lys Asn Val Thr Ile Ser Val Asp Asn Asn
            595                 600                 605
Asn Asn Asn Asp Asn Ser Val Thr Pro Thr Leu Ile Thr Ser Tyr
            610                 615                 620
Tyr Asp Leu Leu Tyr Trp Asn Leu Ser Thr Gly Tyr Asp Phe Glu Glu
625                 630                 635                 640
Glu Arg Arg Lys Gln Tyr Val Glu Lys Tyr Pro Lys Arg Pro Ile Lys
                645                 650                 655
Asp Ile Tyr Ser Glu Leu Glu Leu Tyr Ile Leu Ser Trp Leu Thr Tyr
            660                 665                 670
Ser Gly Lys Thr Phe Ile Ser Pro Tyr Asn Gly Asn Ile Thr Arg His
            675                 680                 685
Asp His Asn Ile Ile Phe Lys Ser Asp Arg Phe Ser Trp Lys Thr Gly
            690                 695                 700
Leu Ser Phe Arg Asp Gln Tyr Tyr Asn Tyr Arg Glu His Leu Gln Tyr
705                 710                 715                 720
Arg Asp Glu Asn Asn Ile Ile Met Ser Ser Arg Leu Arg Leu Leu Gln
                725                 730                 735
Asn Ser Phe Ser Ile Gln Leu Leu Pro Asn Val Ser Val Thr Leu Glu
            740                 745                 750
Asp Phe Arg Asn Leu Arg Glu Leu Gly Thr Phe Gly Lys Thr Asn Ser
```

-continued 755 760 765

Gln Leu Val Glu Val Thr Tyr Leu Ala Gln Cys Tyr Arg Ile Ile Gly
770 775 780

Arg Tyr Arg Tyr Asp Gly Tyr Asp Arg Ser Tyr Thr Val Leu Ile Glu
785 790 795 800

Ile Pro Gly Leu Phe Glu
805

<210> SEQ ID NO 2
<211> LENGTH: 162
<212> TYPE: PRT
<213> ORGANISM: Lawsonia intracellularis

<400> SEQUENCE: 2

Met Glu Val Phe Arg Arg Tyr Gly Ile Val Leu Val Leu Leu Val Val
1 5 10 15

Leu Ser Ala Gly Phe Gly Cys Cys Lys Lys Ser Val Asp Val Glu Gln
20 25 30

Ser Leu Ala Thr Glu Cys Ile Ala Pro Ala Pro Ala Ile Asn Ala Ala
35 40 45

Ala Glu Thr Ile Thr Asp Gly Ile Ile Tyr Phe Asp Phe Asp Lys Tyr
50 55 60

Asp Ile Lys Pro Glu Tyr Arg Asp Met Leu Gln Lys Lys Ala Glu Leu
65 70 75 80

Leu Lys Glu Tyr Pro Cys Ile Arg Val Arg Ile Glu Gly Asn Cys Asp
85 90 95

Ala Arg Gly Thr Gln Glu Tyr Asn Leu Ala Leu Gly Glu Arg Arg Ala
100 105 110

Arg Ala Ala Tyr Glu Tyr Leu Val Met Leu Gly Val Asn Pro Ser Gln
115 120 125

Leu Glu Ile Ile Ser Phe Gly Lys Glu Arg Pro Ala Val Glu Gly Thr
130 135 140

Gly Pro Ala Val Trp Ala Lys Asn Arg Arg Asp Asp Phe Arg Ile Ile
145 150 155 160

Ala Lys

<210> SEQ ID NO 3
<211> LENGTH: 459
<212> TYPE: PRT
<213> ORGANISM: Lawsonia intracellularis

<400> SEQUENCE: 3

Met Lys Arg Leu Leu Leu Cys Ile Ile Thr Cys Val Ile Val Ser Ser
1 5 10 15

Cys Ser Phe Ala Pro Asp Tyr Asn Arg Pro His Leu Glu Leu Pro Glu
20 25 30

Val Trp Val Ser Ser Pro Glu Thr Gly Val Pro Ala Ser Met Gln Trp
35 40 45

Trp Lys Arg Phe Asn Asp Ser Thr Leu Asp Ile Leu Val Ala Glu Ala
50 55 60

Leu Gln His Asn Arg Asp Leu Ile Ala Ala Val Ala Arg Val Asp Tyr
65 70 75 80

Ala Gln Ala Gln Leu Gly Val Ala Arg Ser Asp Leu Phe Pro His Phe
85 90 95

Ser Gly Asn Ala Gln Ala Thr Pro Val Trp Val Asp His Lys Arg Val
100 105 110

```
Thr Asp Gly Gln Ser Pro Tyr Ser Ala Asn Phe Ser Ala Ser Trp Glu
        115                 120                 125

Ile Asp Ile Trp Gly Lys Ile Arg Asn Ala Lys Asp Ala Ala Phe Ser
    130                 135                 140

Gln Leu Met Ala Thr Glu Ala Glu Lys Glu Gly Val Phe Leu Ser Ile
145                 150                 155                 160

Ala Ala Gln Thr Ala Asn Ala Tyr Phe Leu Leu Arg Ser Leu Asp Leu
                165                 170                 175

Gln Cys Ser Ile Ala Glu Arg Thr Val Lys Thr Arg Glu Asp Ala Leu
            180                 185                 190

Ser Ile Tyr Thr Ala Gln Tyr Gln Lys Gly Phe Ile Asn Lys Leu Asp
        195                 200                 205

Leu Thr Arg Ala Lys Thr Glu Val Glu Thr Ala Arg Thr Ala Leu Tyr
    210                 215                 220

Gln Lys Arg Ile Ala Gln Glu Asn Ala Glu Thr Ala Leu Ser Val Leu
225                 230                 235                 240

Leu Gly Arg Ser Pro Arg Leu Ile Met Asp Thr Ala Ile Glu Arg Gly
                245                 250                 255

Val Ser Met Lys Asp Leu Ser Cys Ile Pro Val Ile Pro Gln Gly Ile
            260                 265                 270

Pro Ser Glu Leu Leu Glu Arg Arg Pro Asp Ile Arg Gln Ala Glu Tyr
        275                 280                 285

Thr Leu Lys Ala Thr Ser Ala Asn Ile Gly Val Ala Arg Ala Ala Trp
    290                 295                 300

Leu Pro Ser Ile Ser Leu Thr Gly Leu Phe Gly Ile Val Ser Pro His
305                 310                 315                 320

Leu Ser Asp Leu Leu Lys Asn Pro Leu Lys Thr Trp Ser Tyr Gly Glu
                325                 330                 335

Thr Gly Thr Val Pro Ile Leu Asp Phe Gly Gln Val Tyr Tyr Asn Val
            340                 345                 350

Glu Ala Ala Gln Ala Lys Glu Arg Glu Ala Leu Ala Asn Tyr Glu Lys
        355                 360                 365

Thr Val Gln Asn Ala Phe Lys Asp Ile His Asp Ala Leu Ile Arg Gln
    370                 375                 380

Tyr Glu Ser Lys Asn Ile Val Asn Ser Leu Glu Arg Met Val Lys Glu
385                 390                 395                 400

Leu Arg Ile Ala Val His Leu Ala Arg Thr Leu Tyr Asp Asn Gly Tyr
                405                 410                 415

Thr Ser Tyr Leu Asp Val Leu Asp Ala Glu Arg Ala Leu Phe Gln Ser
            420                 425                 430

Glu Leu Asp Leu Ala Ser Ala Trp Ser Asp Arg Leu Ser Ser Ile Val
        435                 440                 445

Gln Val Cys Leu Ala Leu Gly Gly Ser Trp Glu
    450                 455

<210> SEQ ID NO 4
<211> LENGTH: 796
<212> TYPE: PRT
<213> ORGANISM: Lawsonia intracellularis

<400> SEQUENCE: 4

Met Tyr Lys Phe Ile Ile Phe Tyr Ile Ile Cys Ile Tyr Glu Thr Ile
1               5                   10                  15

Ala Ile Tyr Leu Leu Leu Gly Ser Phe Ile Ser Tyr Phe Asn Arg Val
```

```
            20                  25                  30
Phe Leu Lys Lys Glu Val Lys Ile Leu Asp Thr Thr Lys Val Lys Lys
            35                  40                  45
Tyr Ala Arg Ile Gly Thr Phe Ile Phe Leu Tyr Val Ile Ile Ser Ser
        50                  55                  60
Gln Val Ser Leu Ser His Asn Ala Arg Ile Gly Tyr Glu Asp Lys Asn
65                  70                  75                  80
Ser Asp Arg Lys Ser Lys Leu Ile Leu His Asn Lys Leu Gln Val Asn
                85                  90                  95
Glu Phe Asp Glu Leu Arg Ser Asp Ile Val Val Thr Met Thr Pro Leu
                100                 105                 110
Asn Ile Tyr Thr Ser Thr Gln Glu Asn Lys Ile Thr Thr Ile Glu Ala
            115                 120                 125
Asn Leu Leu Arg Leu Glu Val Ile Gln Arg Thr Gln Pro Val Leu Leu
            130                 135                 140
Val Asp Val Glu Ser Ser Leu Arg Asp Ile Tyr Leu Leu Leu Asp Glu
145                 150                 155                 160
Ala Glu Gly Cys Asn Arg Glu Val Glu Arg Cys Leu Lys Ile Trp Glu
                165                 170                 175
Thr Ala Ser Glu His Thr Lys Val Leu His Arg Gln Thr Arg Glu Arg
                180                 185                 190
Leu Ser Asn Ala Val Ile Glu Cys Gln Pro Gly Leu Pro Thr Asn Asn
            195                 200                 205
Glu Gly Lys Val Val Ser Val Pro Glu Glu Ile Val Ala Ser Ile Glu
            210                 215                 220
Asn Lys Val Leu His Thr Ala Asn Gln Gln Arg Thr Ala Arg Lys Met
225                 230                 235                 240
Glu Val Ala Ile Ser Arg His Lys Asn Lys Asn Ile Phe Leu Gly Asn
                245                 250                 255
Lys Gln Lys Leu Leu Arg Tyr Arg Ile Glu Val Leu Lys Ala Arg Val
                260                 265                 270
Glu Gly Asn Pro Asp Pro Pro Ile Pro Ile Leu Thr Pro Gln Val Leu
            275                 280                 285
Glu Leu Pro Leu Leu Pro Asp Pro Pro Ser Pro Pro Leu Pro
            290                 295                 300
Gln Gln Thr Phe Gln Phe Pro Asp Phe Gly Asp Pro Leu Pro Glu Pro
305                 310                 315                 320
Leu Ser Pro Leu Gly Asp Asp Pro Pro Gln Asn Val Leu Asn Gln Glu
                325                 330                 335
Pro Gln Pro Gly Pro Ser Ser Glu Ile Val Ser Thr Leu Gln Pro Ser
                340                 345                 350
Pro Ser Val Glu Asp Leu Ser Ser Gly Val Thr Leu Glu Cys Gln
            355                 360                 365
Glu Glu Leu Ser Ser Ser Asp Glu Glu Ile Leu Asp Asp Glu Cys Leu
            370                 375                 380
Thr Ser Gly Asp Glu Ser Ser Thr Ser Asp Gly Glu Ser Gln Arg Ser
385                 390                 395                 400
Ser Pro Pro Thr Lys Arg Arg Lys Leu Thr His Thr Pro Pro Ser
                405                 410                 415
Asp Arg Gly Ser Pro Pro Gly Ser Ser Ser Met Leu Met Pro Tyr Tyr
                420                 425                 430
Thr Tyr Gly Gln Val Ser Ser Leu Gln Gly Leu Gln Ser Thr Leu Met
            435                 440                 445
```

Ser Leu Glu Asp Gln Leu Ala Thr Gln Leu Arg Leu Ser Ile Ile Arg
    450                 455                 460

Ser Ile Asn Val Leu Gly Val Cys Cys Lys Asp Asn Gln Leu Gln
465                 470                 475                 480

Pro His Thr Phe Gln Ser Lys Lys Gln Thr Lys Ile Lys Gly Gly Ile
                    485                 490                 495

Gly Arg Ser His Ser Thr Asp Asn Glu Ile Arg Pro Thr Ser Val Asn
                500                 505                 510

Asn Ser Leu Phe Phe Ser Gln Gln Trp His Val Ile Ala Ser Met Asp
        515                 520                 525

Ser Arg Ile Ser Asn Leu Glu Thr Thr Ile Ser Ser Arg Gln Ala Gly
530                 535                 540

Val Phe Thr Thr Pro Ile Asp Gly Leu Cys Leu Ser Leu Leu Tyr Ser
545                 550                 555                 560

Asn Asn Lys Lys Lys Thr Gln Asn Phe Tyr Gly Val Val Leu Asp Ser
                565                 570                 575

Val Asp Gly Ser Ala Lys Ala Gln Ile Glu Thr Asp Asn Ile Leu Ala
                580                 585                 590

Thr Val Thr Trp Asn Lys Glu His Gln Gly Phe Ser Gly His Leu Ala
            595                 600                 605

Gly Cys Tyr Gly Trp Gly Lys Ile Thr Asn Ile Arg Thr Ile His Phe
        610                 615                 620

Phe Asp Asn Glu Ser Val Ser Lys Gly Ile Ser Ser Ile His Met Ser
625                 630                 635                 640

Gly Gly Phe Ile Gln Leu Gly Tyr Asn Val Leu Leu Gly Lys Asn Tyr
                    645                 650                 655

Phe Leu Ile Pro Tyr Val Glu Tyr Met Arg Leu Ala Val Ala Trp Asp
                660                 665                 670

Pro Tyr Glu Glu His Thr Gly Leu Ile Pro Cys Lys Val Ser Gly His
            675                 680                 685

Lys Val His Val Cys Glu Lys Ser Ile Gly Leu Arg Asn Gln Trp Lys
        690                 695                 700

Ile Thr Asp Asn Ser Gln Leu Gln Phe Trp Gly Ser His Ile Phe Thr
705                 710                 715                 720

Asn His Asn Thr Gly Glu Ile Ala Ser Lys Pro Leu Ser Leu Ser Asp
                725                 730                 735

Tyr Arg Asn Lys Ile Ser Ile Pro Gly Tyr Lys Lys Gln Tyr Ile His
                740                 745                 750

Arg Glu Ala Gly Ile Ser Tyr Glu Ser Asn Val Met Asp Thr Leu Ser
            755                 760                 765

Met Glu Leu Tyr Ser Lys Leu Arg Val Thr Lys Ser Ile Lys Asp Val
        770                 775                 780

Thr Ser Tyr Thr Ser Phe Thr Ile Arg Tyr Val Tyr
785                 790                 795

<210> SEQ ID NO 5
<211> LENGTH: 152
<212> TYPE: PRT
<213> ORGANISM: Lawsonia intracellularis

<400> SEQUENCE: 5

Met Gln Arg Cys Gly Leu Tyr Ile Ile Cys Leu Val Leu Ser Ile Gly
1               5                   10                  15

Met Ile Ser Cys Ala Asn Phe Ser Ala Ser Ser Phe Gly Gly Lys Gln

```
            20                  25                  30

Ile Arg Ser Ala His Ile Val Glu Phe Gly Lys Val Val Ser Val Lys
        35                  40                  45

Pro Val Glu Leu Glu Gly Asn Thr Pro Ile Leu Gly Thr Ile Thr Gly
    50                  55                  60

Gly Ala Val Gly Gly Val Leu Gly Ser Leu Ile Gly Gly Gly Ser Gly
65                  70                  75                  80

Arg Ile Leu Ser Thr Val Val Gly Ala Gly Ala Gly Ala Val Ala Gly
                85                  90                  95

Asn Ile Ala Glu Arg Lys Ile Thr Thr Gln Gln Gly Leu Glu Ile Glu
            100                 105                 110

Val Lys Leu Asp Asn Gly Gln Ile Ile Ser Ile Val Gln Gly Ala Asp
        115                 120                 125

Gln Ser Phe Ser Pro Gly Glu Arg Val Arg Val Leu Arg Gly Ser Asp
    130                 135                 140

Gly Ser Ala Arg Val Ser Ser Ile
145                 150

<210> SEQ ID NO 6
<211> LENGTH: 1075
<212> TYPE: PRT
<213> ORGANISM: Lawsonia intracellularis

<400> SEQUENCE: 6

Met Arg Ser Phe Leu Ile Ser Ile Val Thr Leu Phe Leu Leu Gly Ile
1               5                   10                  15

Ile Val Phe Phe Gly Ile Thr Phe Tyr Phe Ile Lys Gln His Pro Gln
            20                  25                  30

Tyr Ile Thr Asn Lys Ile Leu Ser Thr Ile Ser Lys Gln Leu Lys Asp
        35                  40                  45

Thr Ser Ile Ser Ala Asn Ser Ile Gly Phe His Ile Val Pro Phe Pro
    50                  55                  60

Lys Leu Tyr Leu Thr Asn Val Ile Leu Gln Thr Gln Lys Gly Asp Thr
65                  70                  75                  80

Ile His Ile Lys Glu Cys Leu Ile Thr Pro Lys Ile Thr Asn Ile Leu
                85                  90                  95

Ser Gly Asn Ile Ser Ile Tyr Ser Ile Glu Val Ile Gln Pro Ile Ala
            100                 105                 110

Ser Ile Ile Leu Gln Asn Glu Gln Lys Lys Asn Ser Lys Thr Thr Gly
        115                 120                 125

Tyr Ala Ile Pro Lys Gln Val Ser His Leu Leu Gln Leu Ile Thr Asp
    130                 135                 140

Ser Lys Leu Phe Ile Glu Asn Gly Ser Ile Thr Phe Gln Asn Asn Asp
145                 150                 155                 160

Tyr Cys Phe Lys Ile Ile Gly Ile Asn Gly Lys Ile Gly Val Ser Lys
                165                 170                 175

Thr Leu Thr Ser Ser Leu Lys Leu Thr Ala Asp Glu Ile Ile Trp Glu
            180                 185                 190

Ile Met Asn Thr Val Ser Asn Asn Ser Ser Thr Ala Gln Lys Ser Ile
        195                 200                 205

Glu Lys Val Gln Leu His Ile Glu Asp Met Pro Tyr Lys Ile Asn Thr
    210                 215                 220

Ala Leu Leu His Asp Thr Ser Pro Leu Tyr Asp Leu Phe Thr Asn Thr
225                 230                 235                 240
```

-continued

```
Lys Lys Thr Thr Phe Lys Val Ser Gly Ala Ile Pro Thr Thr Asn Thr
            245                 250                 255

Ala Asn Asn Ile Thr Phe Asp Phe Thr Thr Lys Leu Glu Lys Asp Asn
        260                 265                 270

Ser Asp Lys Leu Thr Met His Gly Gln Leu His Ile Glu Gly Thr Leu
        275                 280                 285

Pro Asn Gly Asn Thr Ser Ile Pro Ile Leu Leu Ser Val Pro Phe Thr
        290                 295                 300

Thr Thr Ser Ser Glu Asp Met Thr His Phe Pro Leu Leu Ile Lys
305                 310                 315                 320

Asn Ser Lys Leu Leu Phe Asp Lys Thr His Ile Asp Leu His Gly Thr
                325                 330                 335

Ile Lys Asn Tyr Asp Thr Leu Ser Asn Leu Phe Phe Asp Gly Thr Met
                340                 345                 350

Asp Val Lys Asn Phe Ser Phe Pro Tyr Trp Phe Thr Phe Ala Arg Gln
                355                 360                 365

Leu Pro Asn Gly Ile Gln His Ala Leu Asn Gln Leu Ser Gly Glu Ile
        370                 375                 380

Lys Phe Thr Leu Ser Pro Gln Gln Val Asn Ala Gln Lys Ile Ile
385                 390                 395                 400

His Ser Leu Asp Thr Thr Phe Gln Gly Asn Gly Thr Val Asn Asn Phe
                405                 410                 415

Leu Ser Pro Thr Ile Thr Leu Ser Leu Ala Thr Lys Gln Phe Asn Leu
                420                 425                 430

Asn Thr Leu Leu Pro Glu Leu Lys Gly Lys Lys Ser Ser Gln Leu Ser
        435                 440                 445

Tyr Pro Lys Glu Thr Phe Leu Thr Ile Leu Ser Asn Leu His Asn Asn
450                 455                 460

Asn Asn Asn Asn Asn Ile Lys Lys Thr Ile Asn Tyr Asp Ile Thr Ile
465                 470                 475                 480

Gln Ala Asp His Val Thr Cys Trp Lys Phe Asp Gly Tyr Gln Phe Ile
                485                 490                 495

Cys Asn Ile Gln Pro Lys Pro Gln Gly Thr Gln Ile His Thr Asn Cys
            500                 505                 510

Lys Asn Phe Tyr Asp Gly Ser Leu Ser Ser Ser Leu Leu Leu Ser Asn
        515                 520                 525

Arg His Thr Ile Gln Leu Ala Ile Glu Asn Ile Gln Leu Ser Asp Ile
        530                 535                 540

Thr Asn Ile Ile Thr Lys Glu Tyr Glu Leu Lys Gly Lys Ala Ser Gly
545                 550                 555                 560

Thr Ser Arg Val Asn Gly His Gly Asp Thr Leu Ala Ser Phe Leu Ser
                565                 570                 575

Ser Leu Lys Gly Thr Ile Asp Leu Tyr Val Thr Asp Gly Leu Val Lys
                580                 585                 590

Lys Thr Ala Ser Glu Ala Ile Pro Phe Ser Met Leu His Leu Thr Cys
            595                 600                 605

Asp Ser Ile Gly Gln Pro Ser Lys Gly Asn Lys Ser Ser Thr Ile Pro
        610                 615                 620

Tyr Lys Gly Lys Trp Ser Ala Glu Ile Ser Ser Ala Arg Trp Asn Gly
625                 630                 635                 640

Ser Ile Thr Met Asp Gly Leu Ile Gln Phe Ser Thr Thr Asp Trp Leu
                645                 650                 655

Ser Ile Lys Ala Glu Asn Ile Pro Ser Lys Val Val Cys Ser Val Ser
```

-continued

```
            660                 665                 670
Gly Val Gln Ala Val Ala Tyr Gly Gly Ile Ser Phe Asp Ile Asp Asn
        675                 680                 685

Ser Phe Leu Ser Phe Ser Asn Phe Gln Gly Glu Ile His Pro Lys Thr
690                 695                 700

Ala Leu Ser Gly Thr Ile Lys Thr Ser Ser Thr Ser Asn Thr Arg
705                 710                 715                 720

Gln Trp Glu Gly Ser Leu Thr Val Met Thr Gln Asn Leu Arg Asn Leu
                725                 730                 735

Leu Ser Lys Leu Gly Tyr Glu Pro Lys Asn Ile Ser Pro Thr Met Leu
            740                 745                 750

Gln Tyr Cys Lys Leu Gln Gly Asp Ile Phe Ile Ser Pro Ala Thr Ile
        755                 760                 765

Arg Leu Thr Asn Ile Gln Gly Ile Leu Asp Asn Thr Leu Ile Lys Phe
    770                 775                 780

Ser Leu Asn Gly Leu Gln Thr Asn Pro Pro Ser Trp Thr Gly Asp Ile
785                 790                 795                 800

Gln Leu Ser Ser Leu Asn Leu Asp Lys Tyr Leu Leu Ser Ile Asn Gln
                805                 810                 815

Asn Lys Leu Lys Lys Ser Gln Glu Leu Trp Pro Ile Glu Leu Leu Asn
            820                 825                 830

Lys Val Asn Ile Gln Ser Thr Leu Thr Leu Ala Glu Leu Ile Tyr Arg
        835                 840                 845

Lys Val Pro Tyr Thr Asn Val Val Pro Ile Ser Leu Asn Gln Gly
    850                 855                 860

Thr Leu Ser Ile Thr Pro Ile Thr Ala Ser Leu Cys Asp Gly Lys Thr
865                 870                 875                 880

Glu Ala Ser Phe Lys Ala Cys Pro Leu Ser Thr Asn Gly Asn Ser Ala
                885                 890                 895

Gln Ile Asp Phe His Tyr Ile Ser Lys Gly Val Asp Met Ile Lys Leu
            900                 905                 910

Ser Lys Lys Arg Gln Gln Glu Tyr Leu Ile Ser Gly Leu Gly Thr Phe
        915                 920                 925

Val Ile Asn Ile Gln Ser Ile Ala Lys Ser Ser Ile Asp Phe Leu Lys
    930                 935                 940

Asn Leu Gln Gly Lys Trp Arg Ile Phe Ile Gln Asn Gly Tyr Phe Lys
945                 950                 955                 960

Arg Asn Thr Thr Thr Thr Gln Gln Asn Phe Ser Asn Ile Gly Ala Thr
                965                 970                 975

Gly Asn Ile Ile Asn Gly Ile Ile Thr Asn Asn Asn Phe Ala Ile Thr
            980                 985                 990

Gly Pro Gly Met Val Ile Thr Gly Ser Gly Lys Ile Asp Leu Pro Glu
        995                 1000                1005

Trp Asn Leu Asp Tyr Leu Ile Thr Ile Asp Met Glu Gly Phe Pro
    1010                1015                1020

Ile Ala Ile Pro Ile Lys Tyr Thr Gly Ser Ile Asp Asn Pro Lys
    1025                1030                1035

Arg Thr Ile Asn Ala Ala Lys Leu Ile Leu Ser Thr Ile Gly Ser
    1040                1045                1050

Leu Gly Arg Asp Thr Ile Gly Leu Ile Gln Asp Ile Phe Ser Ala
    1055                1060                1065

Pro Leu Lys Leu Leu Leu Pro
    1070                1075
```

<210> SEQ ID NO 7
<211> LENGTH: 249
<212> TYPE: PRT
<213> ORGANISM: Lawsonia intracellularis

<400> SEQUENCE: 7

Leu Lys Asn Ile Ile Asn Thr Ile Ile Phe Pro Lys Gln Arg Asn Lys
1 5 10 15

Lys Met Ser Gln Lys Phe Ser Met Leu Gln Leu Ile Leu Phe Phe Leu
20 25 30

Thr Phe Ile Phe Tyr Ser Tyr Ile Thr Asp Ser Tyr Ala Glu Ser Ile
35 40 45

Pro Ile Val Lys Glu Leu Gln Gln Ser Tyr Gln Ser Ile Lys Asn Phe
50 55 60

Ser Ala Thr Phe Thr Gln Glu Leu Thr His Gln Glu Ser Gly Ser Lys
65 70 75 80

Glu Thr Arg Ile Gly Lys Leu Phe Phe Lys Lys Pro Leu Leu Val Arg
85 90 95

Trp Glu Thr Asn Thr Pro His Glu Glu Leu Leu Leu Ile Asn Thr Asn
100 105 110

Ala Val Trp Asp Tyr Leu Pro Asp Glu Asn Leu Val Tyr Lys Tyr Ser
115 120 125

Thr Asp Ile Val Lys Asp Ser Thr Ser Ile Ile Gln Val Ile Thr Gly
130 135 140

Gln Val Arg Leu Asp Lys Asn Phe Ser Ile Ile Glu Asn Asn Asn Asn
145 150 155 160

Asn Asn Asn Glu Leu Ile Phe Leu Lys Leu Tyr Pro Lys Glu Pro Thr
165 170 175

Thr Gln Met Val Glu Ala Phe Leu Trp Ile Asn Lys Lys Ser Leu Leu
180 185 190

Ile His Lys Val Gln Ser Ile Asp Phe Tyr Gly Asn Thr Asn Thr Ile
195 200 205

Thr Phe Ile Asn Ile Thr Pro Asn Thr His Ile Asp Asn Asn Ile Phe
210 215 220

Gln Phe Thr Pro Pro Lys Asp Val Thr Ile Glu Asn Leu Gln Asp Ser
225 230 235 240

Ser Thr Pro Glu Arg Pro Leu Phe Asn
245

<210> SEQ ID NO 8
<211> LENGTH: 900
<212> TYPE: PRT
<213> ORGANISM: Lawsonia intracellularis

<400> SEQUENCE: 8

Met Thr Lys Val Gly Gly Ser Asn Pro Phe Ser Thr Leu Ala Ser Met
1 5 10 15

Val Gly Phe Ser Lys Ser Ser Ser Ser Ser Ser Ser Ser Lys Val Ala
20 25 30

Glu Leu Lys Ser Lys Phe Glu Ala Leu Gly Thr Leu Thr Lys Ala Ser
35 40 45

Pro Arg Pro Ala Asn Gly Thr Gln Asp Thr Asn Arg Leu Ser Asp Arg
50 55 60

Leu Phe Arg Gly His Tyr Thr Val Pro Ala Asn Thr Ala Ser Arg Val
65 70 75 80

```
Gly Gly His Leu Gln Arg Val Asp Asp Asn Lys Ser Ser Ser Ala
                85                  90                  95

Ala Asn Val Ala Lys Arg Ala Ala Ala His Ser Ser Phe Ala Ser Ser
            100                 105                 110

Asn Pro Gly Leu Gln Gly Ala Ser Gly Ser Ser Ser Gly Gly Thr Gly
            115                 120                 125

Gly Ser Ile Thr Asp Gln Val Lys Ser Arg Gly Ile Thr Ala Arg Asn
130                 135                 140

Phe Ser Asp Ser Asn Asn Asn Ser Ile Gly Ser Gly Ser Ser Ser Gly
145                 150                 155                 160

Ser Ile Leu Asp Gln Val Arg Ser Gln Gly Ile Thr Ala Arg Gly Ser
                165                 170                 175

Ser Ile Ser Ser Gly Asn Ala Ser Gly Thr Ser Asn Val Asn Asp Gly
            180                 185                 190

Thr Ser Ser Arg Asp Tyr Gly Ala Asn Val Arg Asn Thr Arg Glu Arg
            195                 200                 205

Phe Glu Ala Gly Pro Gly Gly Ala Gln Gly Glu Ser Pro Gly Val Lys
210                 215                 220

Asp Ala Lys Glu Ala Thr Lys Gly Val Ser Val Ser Asn Leu Arg Gly
225                 230                 235                 240

Ile Phe Glu Gly Arg Gly Gly Ala Asp Asn Asn Gln Val Gly Arg Ser
                245                 250                 255

Ser Gly Gly Val Ser Gly Ala Ser Gly Ser Gly Gly Ala Gln Gly Thr
            260                 265                 270

Gly Gly Thr Ser Gly Leu Gly Gly Ala Gln Gly Thr Leu Gly Ser Gly
            275                 280                 285

Gly Leu Asp Gly Gly Gly Val Ser Gly Ala Ala Gly Gly Thr Ser Gly
            290                 295                 300

Ala Ser Gly Ala Gly Gly Ala Arg Gly Thr Ala Asp Gly Ile Thr Ser
305                 310                 315                 320

Pro Gly Ala Arg Glu Ala Gln Glu Thr Ile Lys Asn Ala Gly Val Ser
                325                 330                 335

Val Arg Asp Leu Ala Gly Arg Phe Ser Gly Ala Gln Gly Thr Ser Gly
            340                 345                 350

Ala Ser Gly Ala Ala Gly Ala Ser Gly Ala Ser Gly Ala Gly Gly Ala
            355                 360                 365

Ala Gly Ala Ala Gly Gly Gly Leu Asp Arg Gly Gly Val Ser Gly
370                 375                 380

Ser Ala Gly Gly Thr Ser Gly Thr Ser Gly Ala Gly Gly Ala Arg Gly
385                 390                 395                 400

Thr Ala Asp Gly Ile Thr Ser Pro Gly Ala Arg Glu Ala Gln Glu Thr
                405                 410                 415

Ile Lys Asn Ala Gly Val Ser Val Arg Asp Leu Ala Gly Arg Phe Ser
            420                 425                 430

Gly Ala Gln Gly Thr Ser Gly Ala Ser Gly Ala Ser Gly Ala Ala Gly
            435                 440                 445

Val Ala Gly Met Pro Ala Gly Ser Gly Asp Val Asp Gly Leu Arg
450                 455                 460

Arg Gly Gly Glu Asp Thr Val Asp Gly Phe Gly Arg Asn Gln Gly Ser
465                 470                 475                 480

Gly Pro Ile Pro Ser Ser Ala Asp Phe Val Asp Gly Pro Ile Gly Gly
                485                 490                 495
```

```
Ile Gln Gly Ala Gly Gly Ala Ser Gly Ala Gly Ala
            500                 505                 510

Ser Gly Ala Ala Gly Ala Ser Gly Ala Ala Glu Pro Leu Pro Thr Asn
            515                 520                 525

Gly Thr Asp Gln Gln Ile Ala Glu Val Val Arg Asn Ala Glu Asn
        530                 535                 540

Gly His Phe Asp Gly Ile Asp Phe Ser Thr Gln Pro Gly Gly Val Glu
545                 550                 555                 560

Ser Asn Thr Gly Ser Ile Pro Gly Thr Asp Leu Ile Val Gln Arg Asp
                565                 570                 575

Ile Thr Pro Gly Glu Gln Gly Val Tyr Asn Asn Leu Ser Glu Met Gly
            580                 585                 590

Ser Trp Met Asp Ser Pro Asn Ala Ser Pro Thr Asn Ala Pro Glu Ser
            595                 600                 605

Leu Thr Asp Asp His Ser Val Leu Thr Thr Leu Leu Asn Asn Lys Glu
            610                 615                 620

Gly Leu Gln Asp Thr Val Pro Phe Pro Leu Ala Val Gly Glu Gly Thr
625                 630                 635                 640

Val Val Thr Lys Thr Leu Asp Pro Asp Ile Asp Thr Ser Lys Ile Lys
                645                 650                 655

Ile Pro Leu Glu Ile Val Phe Gly Ser Gly Ser Met Tyr Gly Ser Gly
            660                 665                 670

Ile Gly Gly Gly Ser Ser Thr Ile Ser Ser Ser Met Ser Asp Asp Gly
                675                 680                 685

Ser Ser Ser Ile Gly Ser Thr Thr Arg Lys Asn Arg Ala Gly Glu Ile
690                 695                 700

Ile Ser Arg Ile Ala Met Asn Gln Ser Pro Gly Ala Gly Ser Gly Gly
705                 710                 715                 720

Gln Thr Val Val Gly Gly Leu Gly Ser Gly Ser Ser Asn Ile Asn Ile
                725                 730                 735

Ser Gly Gly Arg Gly Gly Ile Val Tyr Gly Pro Met Pro Asn Val Asn
            740                 745                 750

Val Val Ala Gly Asp Gly Leu Asn Arg Leu Gln Leu Gly Ser Gly Ile
            755                 760                 765

Asn Pro Leu Ala Leu Leu Gln Glu Arg Met Val Asn Phe Ser Ala Ala
770                 775                 780

Gln Leu Glu His Leu His Gly Gln Leu Thr Gly Met Met Ala Met Met
785                 790                 795                 800

Glu Ala Met Pro Gly Val Ala Phe Glu Gly Ala Ser Val Gln Met Thr
            805                 810                 815

Leu Pro Glu Pro Gly Asp Thr Gln Thr Met Pro Ser Ile Arg Leu Ser
            820                 825                 830

Gly Phe Gly Glu Pro Arg Leu Arg Glu Asn Ile Gly Gln Pro Gly Gln
            835                 840                 845

Pro Pro Thr Gln Glu Ala Phe Asp Ala Leu Arg Asn Gly Pro Leu Asn
            850                 855                 860

Gly Val Ser Glu Leu Met Ser Gln Val Gln Glu Met Ile Thr Val Arg
865                 870                 875                 880

Ser Glu Gly Ser Ile Ser Leu Ser Arg Ser Ser Ser Leu Ser Asp Leu
            885                 890                 895

Ser Ser Glu Ile
            900
```

<210> SEQ ID NO 9
<211> LENGTH: 851
<212> TYPE: PRT
<213> ORGANISM: Lawsonia intracellularis

<400> SEQUENCE: 9

```
Met Ala Tyr Leu Ser Ile Ser Lys Asn Gln Cys Lys Ser Phe Leu Ile
1               5                   10                  15

Thr Leu Val Thr Ile Phe Ile Met Thr Ser Ile Pro Gln Leu Ala Glu
            20                  25                  30

Ala Val Glu His Phe Ala Asn Gly Val Pro Thr Val Val Gln Asp Val
        35                  40                  45

Asn Val Pro Ala Asp Ser Tyr Phe Gly Gly Ala Asp Ser Ala Val Gly
    50                  55                  60

Pro Asn Pro Ile Ala Ser Thr His Leu Thr Ile Ser Thr Thr Gln Gly
65                  70                  75                  80

Phe Gly Gln Asn Ala Leu Glu Phe Val Val Gly Gly Ser Leu Ala Asn
                85                  90                  95

Gly Asn Gly Asn Pro Ala Asn Ile Asn Gly Asp Ile Val Leu Ile Val
            100                 105                 110

Glu Asn Thr Asn Thr Gln Asn Ser Ile Ile Gly Gly Ser Met Ala Asn
        115                 120                 125

Ala Ala Pro Val Thr Ile Gly Gly Ser Ile Phe Met Thr Leu Arg Asn
    130                 135                 140

Val Thr Ala Val Asp Pro Ile Phe Gly Gly Ser Val Asp Val Arg Phe
145                 150                 155                 160

Phe Ala Gln Gln Gln Pro Asn Glu Asp Gln Leu Val Gly Gly Asp Ile
                165                 170                 175

Asn Ile Asn Leu Glu Asn Val Thr Thr Pro Glu Phe Tyr Gly Leu Gly
            180                 185                 190

Tyr Ala Asn Gly Val Ile Pro Val Asn Val Leu Asn Arg Asn Phe Leu
        195                 200                 205

Val Ala Val Gln Gly Asn Ile Thr Thr Asn Ile Ser Asn Ser Asn Ile
    210                 215                 220

Ala Thr Val Met Leu Gly Ser His Tyr Asp Thr Thr Met Ala Val Gly
225                 230                 235                 240

Gly Asn Gly Thr Ile Asn Val Asp Asn Ser Thr Ile Gly Tyr Leu Ser
                245                 250                 255

Ala Ser Asn Ser Ser Asp Phe Val Asn Pro Asp Leu Thr Asn Thr Val
            260                 265                 270

Thr Phe Asn Ile Gly Pro Asn Asn Arg Ile Ala Asn Ile Phe Ala Ser
        275                 280                 285

Asn Asn Gly Val Ile Pro His Phe Ile Val Asn Met Asp Gly Ser Gly
    290                 295                 300

Thr Glu Ile Gln Glu Leu Thr Leu Gly Asn Val Ile Arg Gly Gly Leu
305                 310                 315                 320

Val Leu Thr Ser Glu Leu Asn Leu Ser Gln Gly Thr Ile Asn Asn Leu
                325                 330                 335

Ile Thr Gly Asn Glu Tyr Tyr Asp Arg Ser Gly Leu Arg Thr Thr Val
            340                 345                 350

Asn Val Arg Gly Gly Thr Ile Gly Val Leu Thr Ser Gly Gly Ser Asp
        355                 360                 365

Tyr Ser Glu Leu Asn Phe Ile Pro Gly Glu Ile Ser Thr Ile Leu Ala
    370                 375                 380
```

```
Thr Asn Ser Ile Gly Asn Gln Asp Phe Ala Ser Leu Ser Gln Val Thr
385                 390                 395                 400

Ile His Gln Gly Ala Glu Thr Leu Trp Gly Met Arg Asp Glu Val Phe
            405                 410                 415

Glu Leu Gln Thr Asn Asn Leu Gln Leu Gly Gly Glu Leu Phe Ile Pro
        420                 425                 430

Ala Asp Gly Thr Gly Gly Val Ala Leu Ile Thr Asn His Ile Ile Ala
    435                 440                 445

Asn Ser Gly Val Ile Thr Pro Val Asn Met Ser Pro Glu Arg Met Thr
450                 455                 460

Pro Ile Ile Gly Phe Leu Glu Pro Thr Gly Glu Val Ala Gln Leu Thr
465                 470                 475                 480

Ile Tyr Gly Pro Leu Thr Val Asn Leu Ser His Ser Pro Glu Ile Leu
            485                 490                 495

Gly Lys Ile Ile Thr Gln Pro Ile Pro Ile Ala Val Thr Asn Ser Asp
            500                 505                 510

Val Phe Gly Thr Ser Lys Leu Phe Val Glu His Asn Thr Lys Gly Leu
        515                 520                 525

Ile Trp Ser Asp Ile Ile Phe Asn Pro Gln Asp Lys Thr Trp Tyr Leu
530                 535                 540

Thr Asn Phe Arg Gly Ser Glu Asp Phe Tyr Gly Leu Ser Ala Ala Arg
545                 550                 555                 560

Glu Ala Ser Asn Trp Leu Arg Gln Gln His Ile Trp Ser Leu Gln Arg
            565                 570                 575

Arg Ser Asn Lys Leu Leu Asp His Gly Val Asp Gly Leu Trp Met Asn
        580                 585                 590

Val Gln Gly Gly Tyr Glu Lys Leu Asp Ala Ala Ile Gly Asp Ala Lys
    595                 600                 605

Met Pro Trp Ile Met Ala Ser Leu Gly Tyr Asp Phe Met His Lys Leu
610                 615                 620

Ser Asp Phe Tyr Asn Leu Lys Ala Leu Tyr Gly Phe Gly Phe Gly Phe
625                 630                 635                 640

Ala Thr Gly Lys Asn Lys Trp Asn Thr Ile Asn Ser Thr Thr Asn Asp
            645                 650                 655

Ile Tyr Met Gly Leu Val Gly Ala Tyr Val Gly Leu Met His Glu Ala
        660                 665                 670

Thr Gly Leu Tyr Gly Thr Val Ser Gly Gln Phe Ala Thr Asn Arg Thr
    675                 680                 685

Lys Thr Lys Cys Thr Gly Phe Asp Glu Thr Tyr Asn Trp Lys Glu Asn
690                 695                 700

Val Pro Thr Glu Ala Ile Glu Ile Gly Trp Lys Trp Ser Ile Asp Glu
705                 710                 715                 720

Phe Lys Ile Asn Pro Arg Gly Gln Val Ile Phe Glu Gln Leu Ser Lys
            725                 730                 735

His His Phe Ser Leu Ser Gln Glu Gly Asp Thr Ala Ile Leu Asp Lys
        740                 745                 750

Glu Phe Leu Thr Thr Thr Val Ile Gly Ile Ser Gly Glu Tyr Asp Leu
    755                 760                 765

Asp Leu Arg Ser Lys Ile Ile Lys Leu Gln Ala Ser Val Asp Trp Ile
770                 775                 780

Lys Gly Ile Ser Gly Asp Phe Ala Ala Lys Ser Glu Val Leu Asn Met
785                 790                 795                 800

Lys Phe Lys Asp Lys Asn Asp Thr Ser Thr Phe Arg Gly Thr Leu Gly
```

```
                805                 810                 815

Ala Ser Ala Gln Leu Leu Glu Asn Phe Glu Val His Leu Asp Ile Phe
            820                 825                 830

Gly Asp Leu Gly Asn Asp Lys Gly Ile Gly Gly Gln Val Gly Ala Thr
        835                 840                 845

Tyr Arg Phe
    850

<210> SEQ ID NO 10
<211> LENGTH: 112
<212> TYPE: PRT
<213> ORGANISM: Lawsonia intracellularis

<400> SEQUENCE: 10

Met Ser Ala Val Val Asp Ser Met Thr Pro Phe Pro Cys Ser Glu His
1               5                   10                  15

Asp Glu Leu Pro Val Ile Asn Glu Ala Thr Ala Cys Cys Val Phe Asp
            20                  25                  30

Lys Val Glu Ser Tyr Ile Ser Leu Arg Asp Leu Lys Val Gly Gln His
        35                  40                  45

Ala Arg Val Val Arg Val Gln Ala Asp Gly Glu Leu Gly Arg Arg Ile
    50                  55                  60

Arg Asp Met Gly Leu Val Pro Gly Thr Glu Val Thr Ile Val Gly Arg
65                  70                  75                  80

Ala Pro Leu Lys Asp Pro Val Ala Leu Arg Leu Leu Gly Phe Thr Leu
                85                  90                  95

Ser Leu Arg Asn Ser Glu Ala Asp Tyr Val Met Val Ser Pro Ile Ser
            100                 105                 110

<210> SEQ ID NO 11
<211> LENGTH: 183
<212> TYPE: PRT
<213> ORGANISM: Lawsonia intracellularis

<400> SEQUENCE: 11

Met Lys Lys Leu Ile Leu Thr Phe Ala Leu Leu Leu Val Thr Asn Ile
1               5                   10                  15

Thr Thr Phe Ala Ser Glu Pro Phe Thr Leu Ser Ser Pro Gln Met Lys
            20                  25                  30

Asn Gly Thr Ile Ala Thr Asn Gln Val Tyr Asn Ser Phe Gly Cys Lys
        35                  40                  45

Gly Lys Asn Ile Ser Pro Ser Leu Glu Trp Lys Asn Pro Pro Glu Gly
    50                  55                  60

Thr Lys Ser Phe Ala Ile Thr Met Phe Asp Ile Asp Ala Pro Thr Gly
65                  70                  75                  80

Ser Gly Trp Trp His Trp Ile Val Tyr Asn Ile Pro Thr Ser Thr Ser
                85                  90                  95

Ser Leu Val Leu Gly Ala Gly Asn Asp Pro Lys Lys Leu Pro Lys Gly
            100                 105                 110

Ala Val Gln Ser Ile Asn Asp Phe Gly Phe Ile Gly Phe Gly Gly Pro
        115                 120                 125

Cys Pro Pro Val Gly Ala Lys Leu His His Tyr Ile Phe Thr Ile Tyr
    130                 135                 140

Ala Leu Asn Val Glu Thr Met Asp Leu Pro Ala Thr Thr Met Pro Ala
145                 150                 155                 160

Ala Ile Gly Phe Asn Ile His Met His Met Ile Asp Lys Ala Thr Phe
```

-continued

Thr Ala Thr Tyr Ser Arg Lys
            180

<210> SEQ ID NO 12
<211> LENGTH: 939
<212> TYPE: PRT
<213> ORGANISM: Lawsonia intracellularis

<400> SEQUENCE: 12

Met Tyr Asn Ile Ile Asn Lys His Gln Ile Ile Lys Ile Leu Leu Phe
1               5                   10                  15

Ser Leu Cys Val Phe Phe Phe Thr Leu Thr Glu Lys Gln Lys Ile Tyr
            20                  25                  30

Ala Ala Asp Val Phe Phe Glu Gly Arg Thr Glu Thr Leu Ile Asn Val
        35                  40                  45

Asn Lys Pro Phe Asp Ser Phe Phe Gly Gly Ser Asp Ser Thr Ile Gly
    50                  55                  60

Thr Leu Glu Thr Gly Pro Thr Asn Leu Thr Phe Thr Thr Val Gly Ala
65                  70                  75                  80

Phe Arg Asn Ser Val Phe Arg Ile Ile Gly Gly Gly Arg Ser Ser Phe
                85                  90                  95

Asn Asn Pro Asn Thr Val Lys Gly Asn Val Thr Leu Thr Val Tyr Asn
            100                 105                 110

Thr Asp Val Glu Arg Ile Ile Gly Ala Gly Ile Ser Asn Arg Gly Leu
        115                 120                 125

Val Thr Val Thr Gly Ser Val Asn Met Lys Leu Glu Asn Val Ser Val
    130                 135                 140

Thr Arg Gly Ile Tyr Gly Gly Val Tyr Thr Gln Asn Gly His Val Leu
145                 150                 155                 160

Gly Ser Ile Asn Met His Leu Lys Asn Val Gln Thr Pro Leu Leu Ile
                165                 170                 175

Gly Ser Gly Val Ser Asn Gly Pro Asn Arg Ile Thr Val Asn Gly Asp
            180                 185                 190

Ile Asn Ile Asp Val Glu Asp Ser Arg Ile Gln Tyr Val Asn Ile Thr
        195                 200                 205

Gly Glu Val Asp Ala Gly Ile Lys Gly Asn Ala Thr Leu Thr Val Lys
    210                 215                 220

Lys Ser Thr Val Glu Leu Ile Asn Ser Gly Arg Gly Asn Ile Leu Gly
225                 230                 235                 240

Asn Leu Lys Ile Ser Ile Ala Asp Ser Asn Ile Arg Gly Leu Ser Pro
                245                 250                 255

Val Asp Phe Gly Ser Ser Val Tyr Gly Asp Thr Ser Ile Asn Val Ile
            260                 265                 270

Asn Ser Gln Ile Asn Asp Ile Thr Leu Ile Pro Arg Ala Gly Gly Met
        275                 280                 285

Leu Val Gly Pro Val Thr Leu Asp Ile Thr Ser Thr Ile Gln Asn
    290                 295                 300

Ile Gln Cys Gly Pro Val Ser Gln Asn Asn Gln Leu Asn Thr Leu Asn
305                 310                 315                 320

Val Thr Val Asn Thr Ser Asn Ile Thr Asn Leu Asn Leu Gly Ser Val
                325                 330                 335

Glu Gly His Thr Ile Ser Thr Thr Ala Thr Val Thr Asp Ser Asn Ile
            340                 345                 350

-continued

```
Thr Asn Leu Asn Val Gly Thr Phe Asn Gly Leu Gly Val Thr Glu Asn
            355                 360                 365
Ala Ser Val Ile Ile Asn Ser Gly Asn Ile Thr Asn Leu Asn Val Gly
        370                 375                 380
Thr Asn Val Ile Ala Ala Ala Thr Thr Ile Asn Ser Ser Ala Thr Ile
385                 390                 395                 400
His Asp Gly Leu Ile Ala Asn Leu Thr Leu Gly Ser Gln Gly Asn Gly
                405                 410                 415
Arg Thr Met Ile Ala Thr Ala Asn Val Asn Gly Gly Thr Ile Gly Leu
            420                 425                 430
Leu Thr Met Gly Ser Glu Asn Phe Ile Pro Gly Thr Arg Pro Ile Thr
        435                 440                 445
Glu Leu Ala Ile Leu Asn Met Ser Gly Gly Leu Ile Glu Arg Ile Ile
    450                 455                 460
Val Gly Asn Ala Asn Ser Ser Thr Ile Asn Phe Thr Pro Gly Lys Arg
465                 470                 475                 480
Ser Ile Val Lys Thr Ile Asn Gly Pro Glu Leu Pro Tyr Leu Val Asn
                485                 490                 495
Ile Gln Lys Gly Ala Met Thr Gln Trp Gly Thr Lys Asn Met Pro Phe
            500                 505                 510
Leu Leu Asp Thr Arg Asn Leu Ile Leu Ser Gly Thr Leu Ile Thr Ser
        515                 520                 525
Asn Ile Gln Leu Ala Asp Leu Ser Ile Thr Asn Leu Phe Val Ala Asn
    530                 535                 540
Gly Gly Thr Leu Val Pro Arg Lys Leu Ile Pro Gly Asn Gln Pro Val
545                 550                 555                 560
Ile Gln Phe Leu Gly Gly Pro Gln Ser Leu Leu Val Ile His Gln Pro
                565                 570                 575
Leu Lys Val Asn Leu Ser Leu Ser Pro Lys Leu Ile Gly Ser Ser Met
            580                 585                 590
Val Pro Leu Ala Phe Val Ser Gln Ser Phe Ser Ser Pro Asp Leu Phe
        595                 600                 605
Val Lys Gln Thr Arg Ser Gly Leu Ile Trp Ser Asp Leu Glu Phe Asp
    610                 615                 620
Pro Thr Thr Ser Ile Trp Tyr Val Asn Asn Ile Gln Ala Ser Gln Asp
625                 630                 635                 640
Phe Tyr Ser Phe Ser Ile Ala Arg Glu Thr Thr Asn Trp Leu Arg Gln
                645                 650                 655
Gln His Ile Trp Thr Leu Gln Asn Arg Ser Ser Lys Leu Leu Asp Asn
            660                 665                 670
Glu His Tyr Gly Leu Trp Ile Asn Val Gln Gly Gly His Glu Ser Leu
        675                 680                 685
Asp Thr Ser Ile Gly Ser Lys Ala Lys Met Pro Trp Ile Met Ala Thr
    690                 695                 700
Ala Gly Tyr Asp Tyr Leu Gln Gln Leu Pro Arg Leu Asp Met Lys Ala
705                 710                 715                 720
Leu Tyr Gly Leu Ala Phe Gly Ala Ser Lys Gly Lys Ser Lys Trp Ser
                725                 730                 735
Ser Val Asn Ser Thr Lys Asn Asp Ala Glu Leu Gly Met Val Ser Gly
            740                 745                 750
Tyr Val Gly Leu Ile His Asn Lys Thr Gly Leu Tyr Ser Thr Leu Thr
        755                 760                 765
Leu Gln Leu Ala Ser Ser Lys Leu His Thr Asn Ser Thr Gly Phe Tyr
```

```
               770                 775                 780
Arg Asn Phe Lys Trp Thr Glu Thr Thr Pro Thr Glu Ala Leu Glu Leu
785                 790                 795                 800

Gly Trp Lys Tyr Thr Phe Asn Asn Gly Ile Lys Met Asn Pro Arg Gly
                805                 810                 815

Gln Leu Ile Phe Glu Gln Thr Ser Lys His His Phe Asp Leu Gly Ile
                820                 825                 830

Gln Asn Asp Lys Ala Ile Leu Asp Lys Ser Gln Leu Ile Thr Ser Ser
                835                 840                 845

Leu Gly Ile Thr Val Glu Tyr Lys Leu Pro Val Thr Thr Pro Ile Asn
850                 855                 860

Leu Tyr Ala Gly Ile Glu Arg Ile Lys Gly Gln Ser Gly Asn Phe Ala
865                 870                 875                 880

Ile Ser Ser Gln Ser Leu Gln Met Lys Phe Lys His Asp Asn Asp Thr
                885                 890                 895

Ser Val Val Arg Ala Thr Ile Gly Thr Asn Ile Leu Leu Gly Glu His
                900                 905                 910

Phe Asn Ile His Cys Asp Ile Phe Gly Asp Lys Gly Asn Asp Lys Gly
                915                 920                 925

Ile Gly Gly Gln Ala Gly Phe Thr Tyr Lys Phe
                930                 935

<210> SEQ ID NO 13
<211> LENGTH: 398
<212> TYPE: PRT
<213> ORGANISM: Lawsonia intracellularis

<400> SEQUENCE: 13

Glu Ile Val Met Ala Asn Val Ser Gly Ile Pro Ala Pro Arg Leu Leu
1               5                   10                  15

Ser Thr Thr Asn Gln Met Thr Asn Ala Ala Gly Asn Thr Asn Arg
                20                  25                  30

Ala Thr Gly Ser Met Asn Gly Arg Asn Leu Thr Gln Ile Lys Thr Pro
            35                  40                  45

Gln Ser Met Ile Asp Asn Ala Ser Glu Glu Leu Thr Thr Ser Leu Glu
        50                  55                  60

Ser Lys Ser Ser Asp Asp Phe Ala Ile Lys Asp Arg Lys Arg Gln Gly
65                  70                  75                  80

Lys Gly Ser Asp Ser Leu Leu Lys Met Val Gln Glu Tyr Thr Glu Leu
                85                  90                  95

Thr Asn Asp Asp Thr Arg Asn Ala Lys Arg Ala Met Leu Ser Gln Val
            100                 105                 110

Leu Arg Ala Ser Gln Ser Ser Gln Asp Val Leu Glu Lys Thr Leu Glu
        115                 120                 125

Gln Phe Ser Asn Lys Thr Asp Ala Trp Ala Ser Leu Ala Glu Ile Ala
130                 135                 140

Gln Glu Tyr Gly Ala Glu Ser Pro Gln Pro Thr Gly Leu Lys Ser Val
145                 150                 155                 160

Leu Asp Ala Met Glu Thr Leu Glu Asn Glu Phe Gly Asp Glu Ile Lys
                165                 170                 175

Ala Gly Leu Lys Gly Ala Leu Asn Ser Lys Glu Phe Thr Asp Ile Gly
            180                 185                 190

Ser Ala Ala Gln Leu Arg Asp Leu Tyr Thr Thr Thr Val Thr Ile Thr
        195                 200                 205
```

Ala Ala Pro Asp Ala Val Leu Ala Arg Leu Leu Glu Glu Tyr Glu Ser
210                 215                 220

Asp Asp Asp Leu Asp Arg Ala Ile Asp Phe Leu Leu Ser Thr Leu Gly
225                 230                 235                 240

Gly Glu Leu Glu Ser Ala Asp Pro Ser Met Asp Lys Val His Leu Gln
            245                 250                 255

Ser Val Met Gly Asp Ile Glu Lys Thr Gln Gln Leu His Ser Ser His
            260                 265                 270

Lys Gln Cys Thr Thr Ala Leu Ser Arg Trp Lys Glu Lys His Lys Gly
            275                 280                 285

Gly Gly Glu Asn Ser Thr Leu Thr Pro Leu Glu Met Met Arg Glu Leu
290                 295                 300

Ile Ala Leu Lys Asn Glu Asn Phe Ile Ser Pro Ser Ser Ile Asp Lys
305                 310                 315                 320

Ile Val Asp Gln Ala Asp Pro Gln Asp Ile Glu Lys Glu Val Leu Phe
                325                 330                 335

Leu Gln Glu Met Leu Ala Ala Val Arg Lys Phe Pro Ile Met Val Phe
            340                 345                 350

Asp Asn Val Glu Asn Arg Val Arg Val Met Gly Ala Val Gln Asp Ala
            355                 360                 365

Val Asp Asp Ala Val Arg Arg Glu Asp Glu Phe Leu Phe Gln Lys Glu
370                 375                 380

His Pro Asp Val Pro Leu Gln Pro Asp Glu Asn Asn Ile Gln
385                 390                 395

<210> SEQ ID NO 14
<211> LENGTH: 2322
<212> TYPE: DNA
<213> ORGANISM: Artificial Sequence
<220> FEATURE:
<223> OTHER INFORMATION: synthetic sequences

<400> SEQUENCE: 14
attatcaaca tctctgaatt tgcacaaccg acatcaacc agtctcagac caaatggaac       60
ctggaagccg acactctgac cactctgagc aataacacta ttattgaagc gaagggtaac      120
atcatcctga ccaaaggcca ggatgtgttt aaagctgact ttgcacgcta ctatcagaag      180
acgggctggc tgtttctgaa aggtcacgtt accgtgaaaa tggacgaaaa cgagatcaat      240
gcagacgaag cggaattcaa cctgaacacc aaaaccggct ggctgaacaa cggcaatatc      300
ttcattagct ctagccatgt gtacttcagc ggcgcgcgca tcactaaaca ctacggcgat      360
tactacactt ttaacaatgt taaggtgact acctgcgatg gtcctcatcc ggcctggtcc      420
atctctgcga agaagctat tgttgaagtt gatggttacg cgcagctgta tgacagcacc      480
tttaaaatca gaacattga tgttatgtac agcccgatct tcaccatccc ggcgaaacaa      540
actcgtcagt ccggtttcct gaatccgaat tatggtatct ctcaacgccg tggcatctat      600
tacacgcagc cgtacttcct gaacatcgat cagtcctctg acctgacttt ctacgcaggt      660
ctgatgacca aaatcggtcc tctgggcacg gtgcgttacc gctcccacaa atttacgaac      720
cagaagacct ggttcgccgc ttctggtatc acgacaaaaa acaacatcgt tacccccggt      780
aaagacccgg tttatccgtc tagccaactg gtgcgcaata atcaccagcg ctactgggtt      840
cgtggtatgg cagacggttt tatcggtaac tccacctggt gctatatttc taatctggat      900
tacgtgtctg atcaggacta tctgcgtgaa ttcgaccagg gtatcaccgg tttctctcac      960
agccgctccg agatgttcca gatgtttggc cgtgacatcc aggaagacga tcagtcccgc     1020

```
ctgaacgccc tgctgatccg taaagactgg cagcgtatcg gcgtagtggg taacatccgt    1080
tacgaacagg atccaactct gggtcacggc aaccacccga cttcccaaag cgagctgact    1140
cagcgcattc cgcagattga tatgttcctg taccagggta agctgtttca gccgctgagc    1200
ctggaaggcg cgatccacct gcagagcgcc tacatgtatc gtgcaaaagg taccaaaggc    1260
tggcgtaccg aactgtaccc gaaagttacc ctgccgatcg acctgaaata cggctctgta    1320
attacgacgg ttggtctgcg cgaaacttat taccagaccg gtatcaaatc ccacacctct    1380
ccggtagctc cgcacgttcc ggacaccaag actccgcgcc aaaccggtca gcaccgctct    1440
ctgttcaacc tgcagctgga atccagcacc caggcacacc gcatttggcg tctgaaagat    1500
aagaaaacca tcaacctgca cagccagtct attggcaaaa cttttgtac tgctctgaaa    1560 cacacgatcc agccacgtat ctgctactct ttcatcccgc gcgagggcca ggagaaaaac    1620
ccgttctata ctctgagcga tcgcatcctg ccgcagaacg atctgaccta ttccatcgta    1680
aacatcctga ctaagaaaaa tgtcaccatt tccgtcgaca caataacaa caataacgat    1740 aatagcgtta ctccgactct gattacctct tactacgacc tgctgtactg aacctgagc    1800 actggctatg acttcgaaga agaacgtcgt aagcagtacg tagaaaaata cccgaaacgc    1860
cctattaaag atatctactc cgaactggaa ctgtacattc tgtcctggct gacctactct    1920
ggcaaaacct tcatctctcc gtacaacggc aacatcaccc gtcacgatca aacatcatc    1980 ttcaagagcg atcgcttttc ctggaaaacc ggcctgtctt tccgtgacca gtattacaac    2040
taccgtgaac acctgcagta ccgtgatgaa aacaatatca tcatgagctc ccgtctgcgt    2100
ctgctgcaaa actctttctc tattcagctg ctgcctaatg tgagcgtaac cctggaggat    2160
tttcgcaacc tgcgtgaact gggcaccttc ggtaagacca actctcaact ggtggaagtt    2220
acgtatctgg ctcaatgcta ccgcattatt ggtcgttatc gctacgatgg ttacgaccgt    2280
agctacactg tcctgattga aatccctggt ctgtttgaat aa                      2322
```

<210> SEQ ID NO 15
<211> LENGTH: 414
<212> TYPE: DNA
<213> ORGANISM: Artificial Sequence
<220> FEATURE:
<223> OTHER INFORMATION: Synthetic sequence

<400> SEQUENCE: 15

```
aaaagcgtag atgtagaaca aagcctggca accgaatgta tcgcaccggc gccggcaatc     60
aacgcggcgg cagaaacgat cacggacggt atcatttact tcgacttcga taaatacgac    120
atcaagccgg aataccgtga catgctgcag aagaaagctg aactgctgaa ggaatacccg    180
tgcatccgtg ttcgcatcga aggcaactgt gatgcgcgcg gtactcagga atacaatctg    240
gcgctgggtg aacgtcgtgc gcgtgcggcc tatgaatacc tggttatgct gggtgtgaac    300
ccgagccagc tggaaatcat cagcttcggc aaagagcgcc cagctgttga gggtaccggt    360
ccggctgtgt gggcgaaaaa ccgtcgtgac gatttccgca tcatcgcaaa ataa          414
```

<210> SEQ ID NO 16
<211> LENGTH: 1326
<212> TYPE: DNA
<213> ORGANISM: Artificial Sequence
<220> FEATURE:
<223> OTHER INFORMATION: Synthetic sequence

<400> SEQUENCE: 16

```
ttcgctccag attacaaccg tccacacctg gaactgccgg aagtctgggt ttctagcccg      60
gaaactggcg tgccggcatc catgcagtgg tggaaacgtt ttaatgactc tacgctggac     120
atcctggtgg ccgaagccct gcagcacaac cgtgatctga tcgcggcggt tgcgcgtgta     180
gattacgcac aggctcagct gggtgttgcg cgctctgacc tgtttccgca ttttagcggt     240
aacgcgcagg cgactcctgt ttgggttgac cataaacgtg taactgatgg tcagagccct     300
tacagcgcga acttcagcgc tagctgggag attgatatct ggggtaaaat tcgtaacgct     360
aaagatgctg cgttcagcca actgatggca accgaagcag aaaaagaggg tgtgttcctg     420
tctatcgcag cacagactgc taacgcatat ttcctgctgc gctctctgga cctgcaatgc     480
tctatcgctg aacgcacggt aaaaactcgt gaagacgcac tgtctatcta ccgcgcag      540 tatcaaaagg gttttatcaa caaactggat ctgacgcgcg cgaaaaccga agttgagact     600
gctcgtaccg cgctgtacca gaaacgtatc gcacaggaga acgctgaaac cgcgctgtct     660
gtcctgctgg ccgcagccc gcgtctgatt atggatactg ctattgaacg cggcgtatcc     720
atgaaagatc tgagctgtat cccggttatc ccgcagggca ttccgtccga actgctggaa     780
cgtcgtcctg atatccgcca ggcagagtat accctgaaag caacctccgc gaacatcggt     840
gtggcgcgcg cggcgtggct gccgtctatt tctctgaccg gctgtttgg tatcgtttcc     900 ccgcacctgt ccgatctgct gaaaaatcct ctgaaaacct ggagctatgg tgaaaccggc     960
actgtaccaa tcctggactt cggtcaggtt tactataacg ttgaagcggc ccaggcgaag    1020
gaacgtgagg ctctggccaa ctacgagaaa accgttcaga acgccttcaa agacattcac    1080
gacgcgctga tccgtcagta tgaatccaaa aacatcgtca acagcctgga acgtatggtg    1140
aaggaactgc gtatcgccgt ccatctggct cgtactctgt acgacaacgg ctacacctct    1200
tacctggacg ttctggatgc cgaacgcgcg ctgttccaga gcgagctgga tctggcgagc    1260
gcgtggagcg atcgtctgtc tagcatcgtt caggtttgcc tggcgctggg tggctcctgg    1320
gaataa                                                              1326
```

<210> SEQ ID NO 17
<211> LENGTH: 2286
<212> TYPE: DNA
<213> ORGANISM: Artificial Sequence
<220> FEATURE:
<223> OTHER INFORMATION: Synthetic sequence

<400> SEQUENCE: 17

```
aaaaaggaag ttaaaatcct ggacaccact aaagtaaaaa agtatgcgcg tatcggcacg      60
tttatctttc tgtacgtaat catcagctcc caggtgtctc tgtctcacaa cgcccgtatc     120
ggctatgaag acaaaaacag cgaccgcaag agcaagctga tcctgcataa caaactgcag     180
gtcaacgaat tcgacgaact gcgcagcgac atcgttgtga ctatgacgcc tctgaacatc     240
tacacctcca cccaggaaaa caaaatcacc accatcgaag cgaatctgct gcgtctggaa     300
gtcattcaac gtactcagcc ggtgctgctg gttgatgttg aatcttctct gcgtgatatc     360
tatctgctgc tggacgaagc ggaaggttgc aatcgcgaag tggagcgctg tctgaaaatc     420
tgggaaaccg cgtccgaaca cactaaggta ctgcaccgtc agactcgtga gcgtctgagc     480
aatgccgtta tcgaatgtca gccgggtctg cctaccaaca atgaaggtaa agtagtctct     540
gttccggagg aaatcgtcgc gtctatcgag aacaaagttc tgcacacggc gaaccagcag     600
cgtacggcac gtaaaatgga agtggccatt tcccgtcaca aaaacaagaa tatctttctg     660
ggtaacaaac aaaagctgct gcgctatcgc attgaagttc tgaaagctcg tgtggaaggc     720
```

```
aacccggatc cgccgattcc gattctgacc ccgcaggttc tggaactgcc gctgctgccg    780
gatccaccgc catctccgcc gcctctgccg cagcaaacct tccagttccc ggacttcggc    840
gacccactgc cggaaccact gagcccgctg ggcgatgatc caccgcagaa cgtactgaac    900
caggaaccgc agccaggtcc gtcttccgaa atcgtctcca ctctgcagcc atctccgtct    960
gttgaggatc tgagctcctc cggcgtcact ctggagtgcc aggaggaact gtcttccagc   1020
gatgaagaga tcctggatga cgagtgcctg acctccggcg acgaatcttc tacttccgat   1080
ggtgaaagcc aacgttccag cccgccgacc aaacgccgca agctgaccca cactcctcca   1140
ccatctgacc gtggttcccc gccaggctct tcttctatgc tgatgccgta ctatacctac   1200
ggtcaggtgt cttctctgca gggtctgcag tctactctga tgtctctgga agaccagctg   1260
gctactcagc tgcgcctgag cattatccgt tctattaacg tcctgggtgt ttgctgcaaa   1320
gacgacaacc agctgcagcc gcacaccttc caatccaaga acaaaccaa atcaagggt     1380 ggtatcggtc gttcccactc taccgacaac gaaattcgtc cgacgtccgt taacaatagc   1440
ctgttcttta gccagcagtg gcatgtgatc gcttctatgg acagccgtat ctctaacctg   1500
gaaactacta tctcctcccg ccaagcaggt gttttcacca ctccgattga tggcctgtgc   1560
ctgtctctgc tgtactccaa caacaagaaa aaaacgcaga atttctacgg cgttgttctg   1620
gactccgtcg atggcagcgc aaaagcccag attgaaaccg acaatatcct ggcgacggta   1680
acttggaaca agaacacca gggtttcagc ggccacctgg ccggctgcta cggctggggt    1740
aaaatcacca catccgcac catccacttc tttgataacg agagcgtttc taaaggtatc    1800
agcagcatcc atatgtccgg cggcttcatc cagctgggtt acaacgtcct gctgggcaaa   1860
aactactttc tgatcccgta tgtggaatac atgcgtctgg cagtggcatg ggatccgtac   1920
gaagaacaca ctggtctgat ccgtgtaaa gtttctggcc acaaagttca cgtttgcgag    1980
aaaagcatcg gcctgcgcaa ccaatggaaa atcactgaca attcccagct gcagttctgg   2040
ggtagccata ttttcaccaa ccataacacc ggcgaaatcg cctccaaacc gctgtccctg   2100
agcgattacc gcaacaaaat ctctatcccg ggctacaaaa agcagtacat ccaccgcgag   2160
gcgggcattt cctatgagtc taacgttatg gatactctgt ccatggaact gtattctaag   2220
ctgcgtgtga ctaaatccat taaagatgtg acgagctaca cctcttttac catccgttat   2280
gtgtac                                                              2286
```

<210> SEQ ID NO 18
<211> LENGTH: 396
<212> TYPE: DNA
<213> ORGANISM: Artificial Sequence
<220> FEATURE:
<223> OTHER INFORMATION: Synthetic sequence

<400> SEQUENCE: 18

```
ttaattaata gaattcacgg taaacagatc cgtagcgcac acatcgttga atttggtaaa     60
gttgtttctg ttaaaccggt tgaactggaa ggtaacaccc cgatcctggg taccatcacc    120
ggtggtgcgg ttggtggcgt gctgggttct ctgattggcg gtggttccgg tcgtattctg    180
tctactgttg ttggtgcagg tgctggcgcc gtcgcgggca acatcgctga acgtaaaatc    240
accactcagc agggtctgga gatcgaagtt aaactggaca atggccagat catcagcatc    300
gttcaaggtg cggatcagag cttctcccg ggtgaacgtg ttcgcgttct gcgtggttcc     360
gacggcagcg cacgcgtcag ctctatctga ggatcc                              396
```

<210> SEQ ID NO 19
<211> LENGTH: 3189
<212> TYPE: DNA
<213> ORGANISM: Artificial Sequence
<220> FEATURE:
<223> OTHER INFORMATION: Synthetic sequence

<400> SEQUENCE: 19

```
ttaattaata gaattcacat cacgttctac ttcatcaaac agcacccgca gtatatcacc        60
aacaaaattc tgtccaccat ctctaaacag ctgaaggaca cctctatctc tgcgaacagc       120
atcggcttcc acatcgtacc gttccctaaa ctgtatctga ccaacgtaat cctgcagacc       180
cagaaaggcg ataccatcca catcaaagaa tgcctgatca ctccgaaaat cacgaacatt       240
ctgtccggta acatcagcat ctactccatc gaggttattc agccaattgc atccattatc       300
ctgcagaacg agcagaaaaa gaactctaaa acgactggtt atgccattcc aaaacaggtg       360
agccacctgc tgcagctgat caccgatagc aaactgttta tcgagaacgg cagcatcacc       420
tttcagaaca acgactactg ctttaaaatc attggtatca acggcaaaat tggtgttagc       480
aaaactctga cgtcttctct gaaactgact gcagacgaaa tcatttggga gatcatgaac       540
accgtatcca caactccag caccgcgcag aaatctattg aaaaagtgca actgcacatc       600
gaagacatgc catacaaaat caacaccgcc ctgctgcacg acacgagccc gctgtacgat       660
ctgtttacta ataccaagaa gaccaccttc aaggtgtccg cgctatccc gaccaccaac       720
accgcaaaca acattacctt tgactttacc accaaactgg aaaaagataa ctccgacaag       780
ctgaccatgc acggtcagct gcacattgag ggtactctgc cgaacggcaa cacctccatc       840
ccgatcctgc tgtccgttcc gtttaccact actagctccg aagacatgac gcatttccct       900
ccgctgctga tcaaaaacag caagctgctg tttgataaaa cccacatcga tctgcacggc       960
accattaaaa actatgatac cctgtccaac ctgttttcg acggtaccat ggatgtgaaa      1020
aacttctctt ttccgtattg gtttaccttc gcccgtcagc tgccgaatgg cattcagcat      1080
gcgctgaacc agctgtccgg cgaaattaaa ttcactctgt ccccgcagca gtaaacgca      1140
cagaaaatca tcattcacag cctggacact acttttcagg gtaacggcac cgttaacaac      1200
ttcctgtccc ctactattac tctgagcctg gctaccaaac agttcaacct gaacaccctg      1260
ctgccagaac tgaaaggtaa aaagtccagc cagctgtctt accctaagga aacttttcctg     1320
accatcctga gcaacctgca caacaacaat aacaacaaca cattaagaa acgatcaac        1380
tacgatatca ccatccaggc ggaccatgtg acttgttgga gttgacgg ctatcagttc        1440
atttgtaaca ttcagccgaa accgcagggc acgcagatcc ataccaactg taaaaacttc      1500
tacgatggct ccctgtcttc ctcccctgctg ctgagcaatc gtcacaccat ccagctggcc     1560
attgagaaca ttcagctgtc tgatatcact aacattatca ctaaagagta cgagctgaaa     1620
ggcaaagcct ccggcacttc ccgtgtcaac ggtcacggtg atactctggc tagctttctg     1680
agctctctga aaggcaccat cgacctgtac gtaaccgacg gcctggtcaa gaaaccgcg       1740
tctgaagcca tcccgttctc tatgctgcac ctgacttgtg attctatcgg ccagccgagc     1800
aagggtaaca agagctccac cattccatac aaaggtaaat ggtctgcgga aatttcttct     1860
gctcgctgga acgttccat cactatggac ggcctgattc agttctccac caccgattgg     1920
ctgagcatca aagcagaaaa cattccgagc aaagtggtct gcagcgttag cggtgttcag     1980
gcggtcgcgt atgcggcat ctcttttgat atcgataaca gcttcctgag cttcagcaac      2040
ttccaaggcg aaattcaccc gaaaaccgcc ctgagcggta ccatcaagac cagctcctcc     2100
```

```
acctctaaca cccgtcaatg ggaaggttcc ctgactgtca tgacccagaa cctgcgcaac    2160
ctgctgtcca aactgggtta tgaaccgaaa aatatcagcc caaccatgct gcagtattgc    2220
aagctgcaag gtgacatttt catttcccct gctactattc gcctgactaa catccagggt    2280
atcctggaca cacccctgat taagttttcc ctgaacggtc tgcagactaa cccaccgagc    2340
tggaccggcg catccagct gtcctccctg aacctggaca aatatctgct gtctattaac    2400
caaaacaaac tgaaaaagtc ccaggaactg tggcctattg aactgctgaa caaagttaac    2460
attcagtcta ctctgaccct ggcggagctg atctatcgca aagtgccgta caccaacgtg    2520
gtagtgccta tctctctgaa tcagggcacc ctgtctatca ccccgatcac cgccagcctg    2580
tgcgacggta aaccgaagc gtccttcaaa gcttgcccac tgtctactaa cggcaactct    2640
gcccaaatcg acttccacta tatttccaag ggcgtcgata tgatcaagct gtctaagaaa    2700
cgtcagcagg agtacctgat ctctggcctg ggcaccttcg taatcaacat ccagagcatc    2760
gcaaaatcct ctattgactt cctgaaaaat ctgcagggta aatggcgcat ttttattcag    2820
aacggttact ttaaacgcaa cactacgacc actcagcaga acttttctaa catcggtgcg    2880
accggcaata tcattaacgg cattatcacc aataacaact cgcgatcac tggtccgggt    2940 atggttatca ccggtagcgg caagatcgac ctgccagaat ggaatctgga ttacctgatt    3000
actatcgaca tggaaggttt tccaattgcg atcccgatca aatatactgg tagcatcgat    3060
aatccaaaac gcaccatcaa tgcggctaaa ctgattctgt ctaccatcgg ttctctgggt    3120
cgcgatacca ttggtctgat tcaggacatt ttctctgctc cgctgaaact gctgctgccg    3180
tgaggatcc                                                           3189

<210> SEQ ID NO 20
<211> LENGTH: 639
<212> TYPE: DNA
<213> ORGANISM: Artificial Sequence
<220> FEATURE:
<223> OTHER INFORMATION: Synthetic sequence

<400> SEQUENCE: 20
ttaattaata gaattcacga aagcatcccg attgtaaaag aactgcagca aagctaccag      60
tctatcaaaa acttcagcgc gaccttcacc caagagctga ctcaccagga gagcggttct     120
aaagagactc gtatcggcaa actgtttttc aagaaaccgc tgctggttcg ttgggaaacc     180
aacaccccac acgaagaact gctgctgatc aacaccaacg ccgtgtggga ctacctgcca     240
gatgaaaacc tggtctacaa atactctact gatatcgtta agacagcac gagcattatt     300 caagtgatca ccggtcaggt tcgtctggac aaaaacttta gcatcattga aacaataac     360 aacaacaata acgaactgat ctttctgaaa ctgtacccga agaaccgac cacccagatg     420 gtcgaggcct tcctgtggat caacaaaaag agcctgctga tccacaaagt tcagagcatc     480
gatttctacg gtaacactaa caccatcacc tttatcaaca tcaccctaa cacccacatt     540 gataataaca tcttccagtt taccccgccg aaggacgtta ctattgaaaa cctgcaggat     600
agctctactc cggagcgcc actgttcaat taaggatcc                             639

<210> SEQ ID NO 21
<211> LENGTH: 2472
<212> TYPE: DNA
<213> ORGANISM: Artificial Sequence
<220> FEATURE:
<223> OTHER INFORMATION: Synthetic sequence
```

<400> SEQUENCE: 21

```
ttaattaata gaattcacgt agaacacttc gcaaatggcg taccgactgt agttcaagat      60
gtaaacgtgc cggccgattc ttatttcggt ggcgctgatt ctgctgtggg cccgaacccg     120
attgcgtcta cgcacctgac catctctact actcagggct tcggtcagaa cgccctggag     180
ttcgtagtag gtggttctct ggcaaacggt aatggcaacc cagcaaacat caacggtgat     240
attgtactga tcgttgaaaa cacgaacact cagaacagca tcattggtgg ttccatggca     300
aatgcagcgc cggttaccat tggtggtagc atcttcatga cgctgcgtaa cgttaccgct     360
gttgatccga tcttcggtgg ctctgttgat gtccgcttct tcgcacagca gcagccgaac     420
gaggaccagc tggtgggtgg cgatatcaac attaacctgg agaacgtcac tactccggag     480
ttctacggtc tgggttatgc gaatggcgta atcccggtta atgttctgaa tcgtaacttt     540
ctggtggcgg ttcagggtaa catcaccacc aatatctcta acagcaacat cgcaaccgtt     600
atgctgggct cccactacga cactaccatg gcagtaggtg gtaacggcac tatcaacgtg     660
gacaacagca ccattggtta cctgagcgcg tctaattctt ctgacttcgt taatccggac     720
ctgactaaca cggttacctt caacatcggc ccgaacaacc gtattgcaaa catctttgca     780
agcaacaacg gcgtgattcc tcatttcatt gttaacatgg acggttccgg cacggaaatc     840
caggagctga ccctgggtaa cgtaattcgt ggtggtctgg ttctgacgtc cgaactgaac     900
ctgtcccagg gtaccatcaa caacctgatc accggcaacg agtactatga tcgttccggt     960
ctgcgtacta ccgtaaacgt gcgtggtggt accatcggcg tgctgacgtc cggcggtagc    1020
gattattccg agctgaactt catcccaggc gaaatcagca ccattctggc tactaatagc    1080
attggtaacc aagatttcgc atccctgagc caggtaacta ccaccaaggg cgccgaaacc    1140
ctgtggggta tgcgtgatga agtgttcgag ctgcagacta caacctgca gctgggtggc     1200
gaactgttca ttccggcaga tggtaccggt ggtgtagccc tgatcaccaa ccatatcatt    1260
gcaaacagcg gtgtaatcac gccggtgaac atgtccccgg agcgcatgac gccgatcatc    1320
ggtttcctgg agcctaccgg cgaagttgct cagctgacca tctacggtcc tctgaccgta    1380
aacctgtccc actctcctga tcctgggc aagatcatca cgcagccgat cccgatcgct    1440
gtgactaatt ctgatgtgtt cggcacttcc aaactgtttg tggagcacaa taccaagggt    1500
ctgatttggt ctgatatcat ctttaatccg caggacaaga cctggtacct gaccaacttc    1560
cgtggctctg aagatttcta cggcctgtct gccgctcgtg aagcctctaa ctggctgcgt    1620
caacaacaca tctggtccct gcaacgtcgt tctaacaaac tgctggatca cggtgtggac    1680
ggtctgtgga tgaacgtgca aggtggttat gaaaagctgg atgctgctat tggtgatgcc    1740
aagatgccgt ggattatggc ctccctgggc tatgacttca tgcacaaact gagcgacttc    1800
tataatctga aggcgctgta cggtttcggc ttcggtttcg ctaccggcaa gaacaaatgg    1860
aacactatca actctaccac taatgacatt tacatgggtc tggtcggtgc gtacgttggt    1920
ctgatgcatg aagccacggg cctgtatggt accgtgagcg gtcagttcgc gacgaaccgc    1980
accaaaacca atgcactggg cttcgacgaa acctacaatt ggaaagaaaa cgttccgact    2040
gaagccattg aaatcggttg gaaatggtcc attgatgagt ttaaaattaa ccctcgcggt    2100
caggtaatct ttgaacagct gagcaaacat catttttccc tgtctcagga aggtgatact    2160
gcgatcctgg ataaggagtt cctgacgacc actgttatcg gtatttccgg cgaatatgac    2220
ctggacctgc gctccaaaat cattaaactg caggccagcg ttgactggat taaaggcatc    2280
tctggtgatt tcgcagctaa aagcgaagtt ctgaacatga aattcaaaga caaaaacgat    2340
```

```
acttctacct tccgtggcac tctgggtgct agcgcccagc tgctggagaa ctttgaagtt    2400
cacctggata tcttcggtga tctgggtaac gacaaaggta ttggcggcca ggtgggtgct    2460
acctaccgct tc                                                         2472
```

<210> SEQ ID NO 22
<211> LENGTH: 2628
<212> TYPE: DNA
<213> ORGANISM: Artificial Sequence
<220> FEATURE:
<223> OTHER INFORMATION: Synthetic sequence

<400> SEQUENCE: 22

```
tctagcagct ctaaggttgc agaactgaaa tctaaattcg aagcgctggg tacgctgacc      60
aaggcttccc cacgtccggc gaacggtacc caggacacca tcgcctgtc cgaccgcctg     120 ttccgtggcc attatactgt ccctgcaaac accgcaagcc gtgttggcgg tcatctgcag    180
cgcgtcgatg ataacaaatc ctcttctagc gctgcgaacg tagcaaaacg tgctgctgct    240
cactcctctt ttgcgtctag caacccgggt ctgcaaggcg cgtctggctc ttctagcggt    300
ggtaccggcg gtagcattac cgaccaggtg aaaagccgtg gcatcactgc tcgtaatttc    360
tctgactcca acaacaactc catcggcagc ggctctagct ccggctctat cctggaccag    420
gtccgtagcc agggtattac cgcacgtggc tccagcatct cttctggcaa cgcttccggc    480
acctccaacg ttaacgatgg caccagctcc cgtgattacg gtgcgaacgt acgtaacacc    540
cgtgaacgtt ttgaagcagg tccggccggt gctcagggtg aaagcccggg tgttaaagac    600 gctaagaag ccaccaaagg tgtaagcgtc tccaacctgc gtggtatctt tgaaggtcgt     660
ggtggcgcgg ataataacca agttggtcgt tcttctggcg gcgtctccgg cgcatccggc    720
tctggcggcg cccagggcac cggtggtacc tccggtctgg gcggtgctca gggcaccctg    780
ggttctggtg gcctggacgg tggcggtgta agcggtgccg cgggcggtac ttccggcgcc    840
agcggcgctg gcggtgcgcg tggcaccgct gatggcatca cttctccggg tgcacgtgaa    900
gcgcaggaaa ccatcaaaaa cgccggtgta tccgttcgtg atctggcagg ccgttttcct    960
ggtgcgcagg tactagcgg tgcttctggt gctgccggcg cctccggtgc atctggtgcg    1020
ggtggtgcgg caggtgcagc tggccggtggt ggtctggacc cggtggcgt ttctggcagc    1080 gctggcggta ccagcggcac cagcggtgcc ggtggcgcgc gtggtaccgc cgacggtatc    1140
acttccccgg gtgctcgtga agcacaggaa accattaaaa acgctggtgt ttccgttcgt    1200
gacctggccg tcgtttcag cggcgctcaa ggtacttctg gtgcatctgg cgcgtccggt    1260
gcggcaggcg tggcaggcat gccggcgggc tccggcgacg tggtagacgg tctgcgtcgc    1320
ggtggcgaag acaccgttga cggtttcggt cgtaaccaag gttccggccc tatcccatct    1380
tccgccgact tgttgacgg cccgatcggt ggtattcagg gcgcgggtgg cgcttctggt    1440
gcagcgggtg ctgcgggtgc ttccggtgct gctggcgcaa gcggtgcggc ggaaccgctg    1500
ccgacgaacg gtaccgacca gcaaatcgcc gaggtggttg ttcgtaacgc ggagaacggc    1560
cacttcgatg gcatcgactt ctccacgcag ccgggtggcg ttgaatctaa cactggttct    1620
atcccaggca ccgatctgat tgtacagcgt gacatcaccc cgggtgaaca gggtgtatat    1680
aacaacctgt ctgaaatggg ttcctggatg gacagcccaa acgcttcccc gaccaacgca    1740
ccagaatctc tgaccgatga ccactctgtt ctgaccaccc tgctgaacaa caaggaaggt    1800
ctgcaggata cggttccgtt cccgctggca gtaggtgaag gcacggtcgt gactaaaacc    1860
```

```
ctggatccgg atattgatac ctccaaaatc aaaattccac tggagattgt attcggttct    1920
ggctctatgt acggttccgg tatcggtggt ggctctagca ccatctcctc ttctatgtct    1980
gatgacggtt cctcttctat tggttctacc acccgtaaaa accgcgctgg cgaaattatc    2040
agccgcatcg ccatgaacca gagcccaggc gcgggttctg cgggtcaaac tgtggtgggc    2100
ggcctgggta gcggctcttc taacattaat atctctggcg gtcgtggtgg tattgtttac    2160
ggtccaatgc ctaacgttaa cgtggtggca ggtgacggcc tgaaccgcct gcaactgggc    2220
agcggcatca acccgctggc gctgctgcag gaacgtatgg tgaacttcag cgcggcacag    2280
ctggaacatc tgcatggcca gctgactggt atgatggcaa tgatggaggc aatgccgggc    2340
gtggctttcg agggtgcttc cgtacagatg accctgcctg aacctggtga tacccaaacc    2400
atgccgtcca ttcgtctgtc cggtttcggt gaaccgcgcc tgcgtgaaaa catcggccag    2460
ccgggccaac cgcctactca ggaagcgttc gacgcactgc gtaacggccc gctgaacggt    2520
gtgtctgaac tgatgagcca agttcaggaa atgatcacgg tacgctctga aggctctatc    2580
tccctgtctc gctccagcag cctgtctgac ctgtcctctg aaatctaa                2628
```

<210> SEQ ID NO 23
<211> LENGTH: 516
<212> TYPE: DNA
<213> ORGANISM: Artificial Sequence
<220> FEATURE:
<223> OTHER INFORMATION: Synthetic sequencs

<400> SEQUENCE: 23

```
ttaattaata gaattcactc tgaaccgttt actctgtcta gccctcaaat gaaaaatggc      60
actatcgcaa ccaaccaggt ttacaacagc tttggctgta agggcaagaa catctctccg     120
tctctggaat ggaaaaaccc accggaaggc acgaaaagct cgccatcac catgttcgat     180 attgatgccc cgacgggcag cggctggtgg cattggatcg tttataacat tccgacttct     240
accagctctc tggtcctggg cgcaggcaac gacccgaaaa agctgccgaa aggcgctgtt     300
caatctatta acgatttcgg cttcatcggc ttcggtggcc cgtgtcctcc ggtcggcgcg     360
aaactgcacc actatatctt cactatctac gctctgaacg tggaaactat ggatctgccg     420
gcaacgacta tgccagctgc tattggtttt aacatccaca tgcatatgat tgataaagct     480
actttcaccg cgacctatag ccgcaagtaa ggatcc                                516
```

<210> SEQ ID NO 24
<211> LENGTH: 363
<212> TYPE: DNA
<213> ORGANISM: Artificial Sequence
<220> FEATURE:
<223> OTHER INFORMATION: Synthetic sequence

<400> SEQUENCE: 24

```
ttaattaata gaattcacat gtctgccgtt gttgattcta tgactccttt tccgtgctct      60
gaacacgatg agctgcctgt tattaacgaa gccaccgcat gctgtgtttt tgacaaggtt     120
gagagctaca tttccctgcg cgacctgaag gtgggccagc atgcccgtgt ggttcgtgtg     180
caagcggacg cgaactgggt cgccgtatt cgtgacatgg gtctggtccc gggcaccgaa     240
gtaactatcg taggccgcgc gccactgaaa gatccggttg ccctgcgtct gctgggtttt     300
actctgagcc tgcgtaactc tgaagctgat tacgttatgg tgtctccgat ttcttaagga     360
tcc                                                                   363
```

<210> SEQ ID NO 25
<211> LENGTH: 2739
<212> TYPE: DNA
<213> ORGANISM: Artificial Sequence
<220> FEATURE:
<223> OTHER INFORMATION: Synthetic sequence

<400> SEQUENCE: 25

| | | | | | |
|---|---|---|---|---|---|
| aaacaaaaga | tctacgcggc | ggatgtattc | tttgaaggtc | gtaccgaaac | cctgatcaac | 60 |
| gtgaacaagc | cgttcgactc | tttctttggc | ggtagcgatt | ctaccattgg | caccctggaa | 120 |
| accggcccga | ctaacctgac | tttcaccacc | gttggcgcct | ttcgtaactc | cgtattccgt | 180 |
| atcatcggcg | gtggtcgttc | cagcttcaac | aacccgaaca | ctgtgaaagg | taacgtgacc | 240 |
| ctgactgttt | acaacaccga | cgttgaacgt | atcatcggtg | ctggcatctc | caaccgtggt | 300 |
| ctggtgaccg | tgaccggttc | cgttaacatg | aaactggaga | acgtgtccgt | cacgcgtggt | 360 |
| atctacggtg | gcgtttacac | ccagaacggt | cacgtgctgg | gttctatcaa | catgcacctg | 420 |
| aaaaacgtgc | agaccccgct | gctgatcggt | tctggcgtat | ctaacggccc | gaaccgtatt | 480 |
| accgtaaacg | gcgacattaa | cattgacgtc | gaggatagcc | gtatccagta | cgtgaacatc | 540 |
| accggcgagg | tagatgcagg | cattaaaggt | aacgcaaccc | tgaccgttaa | aaagagcacc | 600 |
| gtggaactga | tcaacagcgg | tcgcggcaac | atcctgggta | atctgaaaat | ctctatcgca | 660 |
| gacagcaaca | ttcgtggcct | gtctccggtc | gacttcggca | gctccgtata | cggtgacacg | 720 |
| agcatcaacg | ttattaactc | ccagatcaac | gacatcaccc | tgattccgcg | cgcaggcggc | 780 |
| atgctggttg | gcccggtcac | tctggacatt | acctcttcca | cgattcagaa | cattcagtgt | 840 |
| ggcccggtgt | cccagaacaa | ccagctgaat | actctgaatg | tgaccgtaaa | cacgtccaat | 900 |
| atcaccaacc | tgaacctggg | ctctgtagaa | ggccatacca | tcagcaccac | cgcgaccgta | 960 |
| acggattcca | acatcaccaa | tctgaacgtc | ggcaccttca | acggcctggg | tgttaccgag | 1020 |
| aatgcatctg | tcattattaa | cagcggtaac | attactaatc | tgaacgtagg | cactaacgtt | 1080 |
| attgcggctg | cgactacgat | caattcttcc | gctaccatcc | acgacggcct | gatcgcaaac | 1140 |
| ctgactctgg | gcagccaggg | taacggtcgt | actatgatcg | ctaccgctaa | cgtcaacggt | 1200 |
| ggcaccattg | gtctgctgac | catgggttct | gaaaacttca | ttccgggtac | ccgtccgatc | 1260 |
| accgaactgg | cgatcctgaa | catgagcggt | ggtctgatcg | aacgtatcat | tgtgggtaac | 1320 |
| gctaattctt | ctactattaa | cttcacgcca | ggtaaacgtt | ccatcgtaaa | aaccatcaat | 1380 |
| ggcccggaac | tgccgtacct | ggttaatatc | cagaaaggcg | cgatgactca | atggggcacc | 1440 |
| aaaaacatgc | cgttcctgct | ggacacccgt | aacctgattc | tgtccggtac | tctgatcact | 1500 |
| agcaacatcc | agctggcaga | cctgagcatt | accaatctgt | tgtggctaa | tggtggcacc | 1560 |
| ctggttcctc | gcaaactgat | tccgggtaac | cagccggtta | ttcagttcct | gggtggcccg | 1620 |
| cagtctctgc | tggtgatcca | tcagccgctg | aaagtaaacc | tgagcctgtc | tccaaagctg | 1680 |
| atcggctcca | gcatggtccc | tctggcgttc | gtatcccagt | cttttcagctc | tccagatctg | 1740 |
| tttgtgaaac | agacccgctc | cggcctgatt | tggtccgatc | tggaatttga | cccaacgact | 1800 |
| agcatctggt | acgttaacaa | cattcaggcg | tcccaggatt | tctatagctt | cagcattgcg | 1860 |
| cgtgaaacca | ccaactggct | gcgtcaacag | catatttgga | ccctgcagaa | ccgttcctcc | 1920 |
| aaactgctgg | acaacgaaca | ctacggcctg | tggattaacg | tacaaggcgg | ccacgagtct | 1980 |
| ctggacactt | ccatcggtag | caaggcaaaa | atgccatgga | tcatggctac | cgcgggttat | 2040 |
| gattatctgc | agcaactgcc | gcgtctggac | atgaaagcac | tgtacggcct | ggcatttggt | 2100 |

-continued gcctctaaag gtaaaagcaa gtggtcttcc gtaaatagca ctaagaacga tgcggaactg 2160
ggcatggttt ctggttacgt cggtctgatc cacaacaaaa ctggcctgta tagcactctg 2220
actctgcagc tggcttcttc taaactgcat accaatagca cgggttttta tcgtaacttt 2280
aaatggacgg aaaccactcc aactgaggcg ctggagctgg gttggaaata cacctttaac 2340
aatggcatca aaatgaaccc tcgtggtcag ctgattttcg aacagactag caaacaccac 2400
ttcgacctgg gtatccagaa cgacaaagcg atcctggaca aaagccagct gatcaccagc 2460
tccctgggta ttacggttga gtacaaactg ccggtcacca cgcctatcaa cctgtacgca 2520
ggtatcgagc gtattaaagg ccaatccggc aactttgcga tttccagcca gtccctgcag 2580
atgaagttca agcatgataa cgacaccagc gtggtccgtg ctaccatcgg tacgaacatt 2640
ctgctgggcg agcacttcaa catccactgc gatatcttcg gtgacaaagg caatgacaag 2700
ggtatcggcg gtcaggctgg tttcacctac aaattctaa 2739

<210> SEQ ID NO 26
<211> LENGTH: 1140
<212> TYPE: DNA
<213> ORGANISM: Artificial Sequence
<220> FEATURE:
<223> OTHER INFORMATION: Synthetic sequence

<400> SEQUENCE: 26
ttaattaata gaattcacgg taacactaat cgtgctactg gctctatgaa tggtcgtaat 60
ctgacccaga tcaaaacgcc gcagagcatg atcgacaacg cgtctgagga actgaccacc 120
tctctggaaa gcaaatcttc cgacgacttc gcgattaagg atcgtaaacg tcagggcaag 180
ggctccgaca gcctgctgaa aatggttcag gaatatactg agctgacgaa tgatgacacc 240
cgtaacgcga aacgtgcgat gctgtctcaa gtgctgcgtg ctagccagtc tagccaggac 300
gtgctggaga aaaccctgga gcagttctct aacaaaactg acgcctgggc gtctctggcc 360
gaaatcgcac aagaatacgg cgcggaatct ccgcagccga ctggtctgaa aagcgtactg 420
gacgccatgg aaacgctgga aaacgagttc ggcgacgaga tcaaagcagg tctgaagggc 480
gccctgaact ccaaagagtt cactgatatc ggtagcgctg ctcagctgcg tgacctgtac 540
actactaccg tcaccattac cgctgcacct gatgcagtac tggcccgcct gctggaagaa 600
tatgaatccg atgacgacct ggaccgcgcg atcgatttcc tgctgtctac tctgggtggc 660
gaactggaaa gcgcagatcc gagcatggat aaagtccacc tgcaatctgt gatgggtgat 720
atcgagaaaa ctcaacagct gcacagctcc cacaagcagt gcactactgc tctgagccgt 780
tggaaggaaa aacacaaggg cggtggtgag aactctactc tgaccccgct ggaaatgatg 840
cgcgagctga tcgcactgaa aaacgaaaac ttcatttctc cttcctccat cgacaaaatt 900
gtggaccagg cagacccgca ggacatcgag aaagaagttc tgttcctgca agaaatgctg 960
gctgccgtgc gtaaatttcc gattatggta ttcgataacg ttgaaaaccg cgttcgtgta 1020
atgggtgccg ttcaggatgc ggtggacgat gccgtacgtc gtgaagatga gttcctgttc 1080
cagaaagagc atccagatgt gccgctgcag ccggatgaaa acaacatcca gtaaggatcc 1140

<210> SEQ ID NO 27
<211> LENGTH: 2421
<212> TYPE: DNA
<213> ORGANISM: Lawsonia intracellularis

<400> SEQUENCE: 27
ttgtataatc ttttttacc atttattcta actaacctta tatattatat aattattcca 60

```
tccttattta tagcattttt tcctctacaa gctttatcta ttataaacat atccgaattt      120
gcacaaccag atattaacca atctcaaact aaatggaacc ttgaagctga tacgttaact      180
acactatcaa ataatactat tattgaagct aaaggaaaca ttatccttac aaaaggacag      240
gatgtattta aagctgactt tgcaaggtat tatcaaaaaa caggttggct tttccttaaa      300
ggtcatgtca ctgtaaagat ggatgaaaat gaaatcaatg ctgacgaagc agaatttaat      360
ttgaatacta aaacaggctg gcttaataat gggaacatat ttatctcttc atcacatgtt      420
tacttttctg gtgcacgtat taccaaacat tacggagatt attatacttt taataatgtc      480
aaagttacta catgtgacgg acctcatcca gcatggtcaa tatcagctaa agaggcaata      540
gtagaagttg atggatatgc acaattatat gattctacct ttaaaattaa aaacatagat      600
gtaatgtata gccctatttt tacaatacct gcaaaacaaa caagacaatc aggtttttta      660
aatcctaatt atggaatcag tcagcgacgt ggaatttatt atactcaacc atactttta      720 aatattgatc aaagcagcga tctaacattt tatgctggac tgatgacaaa aataggtcca      780
ttaggaactg taagatatcg ttcacacaaa tttacaaatc aaaaaacatg gtttgctgct      840
agtggcattc atgataaaaa taatattgtc acaccaggga aagatcctgt ctatccatca      900
agccaacttg tacgtaataa ccatcaacgt tattgggttc gtggaatggc tgatggtttt      960
attggaaact caacttggtg ctatatatct aatttagact atgtatcaga ccaagattat     1020
cttagagaat ttgatcaagg tataacaggc ttttcacact cccgtagtga aatgtttcaa     1080
atgtttggca gagatatcca agaagatgac caatctcgat taaatgcttt acttattaga     1140
aaagattggc agcgtatagg ggtagtagga aatattagat atgaacaaga tccaacatta     1200
ggacatggga atcatcctac tagtcaaagt gagttaacgc aacgaattcc acaaattgac     1260
atgtttcttt accaaggaaa actatttcaa cctctttcat tagagggtgc cattcattta     1320
cagtctgctt atatgtatcg tgctaaaggc actaaaggtt ggagaacaga actttatcca     1380
aaagttacat taccaatcga tctcaaatat ggatctgtta taacaactgt tgggctacgt     1440
gaaacttact atcaaacagg tataaaatca cacacaagtc ctgtagcacc acatgtccct     1500
gatactaaaa caccacgtca aacaggtcag catcgttcac tttttaactt acaactagaa     1560
agtagtacac aagctcaccg aatatggcga ctaaaggata aaaaactat taatcttcat     1620 tctcaaagta taggaaaaac cttttgtaca gcactcaagc atacaatcca accacgtata     1680
tgctatagct ttatacctag agaaggccaa gaaaaaaatc cattttatac actatcagat     1740
aggatccttc cccaaaatga ccttacttat tcaatagtaa atattctcac aaaaaagaat     1800
gttactatta gtgtagataa taataataat aataatgata atagtgttac accaacactt     1860
attacttcct actatgatct tctctactgg aacttatcaa caggatatga ttttgaagaa     1920
gaacgccgaa acaatatgt agaaaaatat ccaaagcgcc ctataaaaga catctattct     1980
gaactagaac tttatatact atcttggtta acttattcag gtaagacatt tatttctcca     2040
tataacggta atattactag acatgatcat aatatcatat tcaaatcaga cagattttct     2100
tggaaaacag gccttagctt tcgtgatcaa tactataatt accgtgagca tcttcaatat     2160
cgagatgaaa ataatattat tatgtctagt aggttacgct tacttcaaaa ctctttttct     2220
atacagctat taccaaatgt atctgttacg ttagaagatt tccgaaacct acgagaactt     2280 ggaactttg gtaaaacaaa ctctcaacta gttgaagtta catatttagc acaatgttat     2340
cgtattattg gtagataccg atatgacggc tatgatcgta gctatacagt attaatagaa     2400
```
atacctggat tatttgaata a 2421

<210> SEQ ID NO 28
<211> LENGTH: 489
<212> TYPE: DNA
<213> ORGANISM: Lawsonia intracellularis

<400> SEQUENCE: 28
atggaagtat ttagacgtta tggcatagtt ctggttctgt tagtagtatt aagtgcaggt 60
tttggttgtt gtaaaaagag tgttgatgta gaacaatctt tagcaacgga gtgtattgct 120
ccagcaccag caattaatgc agctgcagaa actataactg atgggattat ttattttgat 180
tttgataaat atgatattaa acctgaatat cgtgatatgt tgcagaagaa agctgaactt 240
ttaaaagaat atccttgtat tcgtgtccgt atagaaggta attgtgacgc tcgtggtact 300
caagagtata atttagcact tggagagcgt cgtgcacgtg cagcatatga atatttagtc 360
atgcttggag taaatccatc tcagcttgag ataataagtt ttgggaaaga gcgtccagct 420
gttgaaggaa cagggccagc tgtatgggca aaaaatcgtc gtgatgattt tcgtattatt 480
gccaagtaa 489

<210> SEQ ID NO 29
<211> LENGTH: 1380
<212> TYPE: DNA
<213> ORGANISM: Lawsonia intracellularis

<400> SEQUENCE: 29
atgaaaagat tgttactctg tattataaca tgtgttattg tatcaagttg ctcttttgct 60
ccagattaca atcgaccaca tttagagtta cctgaggtat gggttagttc accagagaca 120
ggagttcctg cttctatgca gtggtggaaa cgctttaatg attctacact tgatatttta 180
gtagcagaag ctttgcagca taatagagac ttaattgcag ctgtggccag agtagattat 240
gcacaagctc agttaggagt tgctcgatca gatttgtttc cacatttttc aggaaatgct 300
caagcaacac ctgtatgggt agatcataag agggttacag atggacaatc tccatatagc 360
gcaaactttt cagcaagttg ggaaattgat atttggggaa agatacggaa tgccaaagat 420
gctgcatttt ctcaattaat ggctacagaa gcagaaaaag agggtgtttt tctttctatt 480
gctgcccaaa cagcaaatgc ttattttttg ttgaggagcc ttgacttaca atgttctatt 540
gcagagagga cagtaaaaac acgtgaagat gcattaagta tctatactgc acaatatcaa 600
aaaggattta ttaacaaatt agatttaact cgagcaaaaa cagaagttga gacagcacgt 660
acagcacttt atcaaaaacg tattgcacaa gagaatgctg aaacagcttt atctgttttg 720
ttaggccgtt ctccacggtt aattatggac acagcaattg agcgtggggt atctatgaaa 780
gatttatctt gtattcctgt tattcctcaa ggtattcctt cagagctttt agaaagacgt 840
cctgatatac gtcaagctga atatacgtta aaagctacta gtgcaaatat tggtgtggca 900
agagcagctt ggttaccatc tatttcatta acaggattat ttggtattgt aagcccacat 960
ttaagtgatt tattaaaaaa tcctttaaaa acatggagtt atggggaaac tggaactgtg 1020
cctattttag attttggtca ggtatactat aatgtggaag cagcccaggc aaaagaacgt 1080
gaagcattag ctaactatga aaaaacagta caaaatgctt ttaaagatat tcatgatgct 1140
cttatacggc aatatgaatc aaagaatata gttaattcac ttgaacgaat ggtgaaagag 1200
ttacgtatag ctgtacatct tgcacgtact ctttacgata atggttatac atcttatctt 1260
gatgtgttag atgcagaacg tgctcttttt caaagtgaac tagatcttgc tagtgcttgg 1320

```
agtgatcgcc tatcttctat tgtacaagtt tgtttagcat taggaggcag ttgggaataa    1380
```

<210> SEQ ID NO 30
<211> LENGTH: 2391
<212> TYPE: DNA
<213> ORGANISM: Lawsonia intracellularis

<400> SEQUENCE: 30

```
atgtataaat ttattatatt ttatattata tgtatatatg aaacaatagc catatattta      60
ctcttaggta gttttatatc ctattttaat agagtctttc ttaaaaaaga agtaaaaata     120
ttagatacta ctaaagtaaa aaagtatgct agaataggaa catttatttt tttgtatgta     180
ataataagtt ctcaagtatc gttatctcat aatgctcgta taggctatga agataaaaat     240
agtgatagga agagtaaact gattttacat aacaaattac aagtaaatga gtttgatgag     300
cttcgttcag atattgtagt tacaatgaca ccattaaata tatatacttc tactcaggaa     360
aataaaatta caactataga agccaacctt ttaagattag aggtgataca gcgaacacaa     420
cctgtgcttt tagtagatgt cgaaagcagt cttcgtgaca tatatcttct actggacgaa     480
gctgaagggt gtaatagaga agtagaaaga tgtcttaaaa tatgggaaac agctagtgaa     540
catacaaaag tactgcatcg tcagactagg gagcgtttat ctaatgcagt aatagagtgt     600
caaccagggt tacctactaa taatgagggt aaagtagtaa gtgtaccaga agaaattgtg     660
gcttccattg aaaataaggt gttacataca gcaaatcaac aaagaactgc acgaaaaatg     720
gaagtagcta tcacgacaa taaaaataaa aatattttct tggggaataa acaaaaacta     780
cttaggtatc gaattgaagt actgaaagcg cgtgtagaag gtaatcctga tcctcctata     840
cctatactta caccacaagt gcttgaatta ccacttttac ctgatccacc accatcacca     900
ccaccattgc cacagcagac ttttcaattc ccagattttg gagatcctct tccggaacca     960
ttgtctcctt taggagatga tcctccccaa aatgtactaa atcaagagcc tcagccagga    1020
ccatcttctg agattgtctc aactttacag ccttcacctt cagtagagga tctatctagt    1080
tcaggagtga ctttagaatg tcaagaagag cttttctagca gtgatgagga gatattagat    1140
gatgagtgtt taacctctgg cgatgaatct tcaacatcag atggtgagtc tcaaaggtca    1200
tcaccgccaa caaaacgtag gaagctaact catactccac caccttctga tagaggctct    1260
cctccaggga gttcttctat gcttatgcca tattacacat atggacaagt cagttctctt    1320
caaggattac aaagtacgtt aatgagttta gaggatcagt tagcaacaca attacgacta    1380
tctattatta gatccattaa tgttttaggt gtttgttgta aggacgacaa tcagttacaa    1440
cctcatactt ttcaaagtaa aaaacagact aaaattaaag gaggaatagg aagaagtcac    1500
tcaacagata atgaaatacg tccaacttct gtgaataatt cattatttt ttcgcagcaa    1560
tggcatgtta ttgcatctat ggatagtcgt atatctaatt tagagactac tatttcttca    1620
agacaagcag gggttttac aacacctatc gatggactct gtttatcttt attgtatagt    1680
aataacaaaa agaaaactca aaatttctat ggagttgtac tagactcagt agatggttct    1740
gcaaaagctc agatagaaac agataacatt ttagcaacag tgacatggaa taaagaacat    1800
caaggttttt caggtcattt agcaggttgt tatgggtggg ggaaaataac aaatattcgt    1860
acaatacatt ttttgataa cgaaagtgtt tctaaaggta tttcaagtat acatatgagt    1920
ggtggattta ttcagctagg atataacgtt ttactaggaa aaaattattt tcttattcca    1980
tatgttgaat atatgagatt agcagtagca tgggatccat atgaagaaca tacaggtctt    2040
```

-continued

```
attccttgta aagtgagtgg acataaagtt catgtttgtg agaaaagtat aggtttgcgt   2100
aatcaatgga aaattacaga taattcccag ctacagtttt ggggttctca tatttttaca   2160
aatcataata caggtgaaat agcttctaaa ccacttagtt tatctgacta taggaataaa   2220
atatctattc ctggttataa gaagcaatat atccataggg aggcagggat ttcttatgag   2280
tcaaatgtaa tggatacatt atctatggag ctttatagta agttaagggt aactaaaagc   2340
ataaaagatg ttactagtta tacaagtttt acaataagat acgtttatta a            2391
```

<210> SEQ ID NO 31
<211> LENGTH: 459
<212> TYPE: DNA
<213> ORGANISM: Lawsonia intracellularis

<400> SEQUENCE: 31

```
atgcagcgtt gtggtcttta tatcatttgt ttagtgttat ctataggtat gataagttgt     60
gcaaatttta gtgcttcttc ttttggaggg aagcaaattc gtagtgcaca tattgttgaa    120
tttggaaaag tcgtttctgt aaaacctgtt gaactagaag gaaatacacc aattctaggt    180
actattactg gtggagctgt tggtggtgtt cttggtagtt taatcggtgg aggatcagga    240
agaatattat caactgttgt tggtgctgga gcaggggctg ttgctggaaa cattgctgaa    300
agaaaaatta caacgcaaca aggtctcgaa atagaagtga aacttgataa tggtcaaatt    360
atttctatag ttcaaggtgc tgatcaatct tttagtcctg gcgaacgtgt tcgagtacta    420
cgtggaagtg atggttcggc tcgagtatct tcaatatag                           459
```

<210> SEQ ID NO 32
<211> LENGTH: 3228
<212> TYPE: DNA
<213> ORGANISM: Lawsonia intracellularis

<400> SEQUENCE: 32

```
atgagatctt ttctcattag tatagttact ctctttctat taggaattat agtatttttt     60
ggtattacat tctactttat caaacaacat ccacaatata ttacaaataa aatactttct    120
actatttcaa aacaattaaa ggatacttct atttctgcta attctattgg gtttcatatt    180
gtaccttttc ctaagcttta cttaacaaat gttatacttc aaacacaaaa aggtgataca    240
attcatatta aagaatgctt gattactcca aaaatcacca acatattatc aggaaacatt    300
tctatatatt ctattgaggt aatccaacca atagcctcca ttattcttca aaatgaacaa    360
aaaaaaaata gtaaaaccac aggatatgct ataccaaaac aagtttcgca tcttctccaa    420
ttaattacag atagtaaact ttttattgaa aatggtagta ttacctttca aaataatgac    480
tattgtttta agataatagg tattaatggt aaaattggtg tttctaagac acttacaagc    540
tcattaaagc tcactgcaga tgaaataatc tgggaaataa tgaatactgt aagtaataat    600
tctagcactg cacaaaaaag tattgaaaaa gtacagctcc acatagagga tatgccgtat    660
aaaataaata cagcattact tcatgatact tctcctttat acgatttatt tacaaatact    720
aaaaaaacta catttaaggt ttcaggggct atacctacaa ccaatacagc taataacatt    780
acattcgact tcacgacaaa actagaaaaa gataactctg ataaacttac aatgcatggg    840
cagttacata ttgaaggaac actccctaat ggtaatacat ccattcctat actattatct    900
gttccgttta caacaacatc ttctgaggac atgacacact ttcctccact gctgataaaa    960
aactcaaaac tactttttga taaaactcat atagatcttc atggaacaat aaaaaattat   1020
gatacactat caaatctctt ttttgatgga acaatggatg taaaaaattt tagttttccc   1080
```

```
tattggttta cttttgcaag gcaactacca aatggtattc aacatgctct aatcaatta      1140 tctggagaaa taaaatttac attatctcct caacaagtta atgcccaaaa aataatcatt      1200
cattctttag atactacatt tcaagggaat ggaactgtca ataattttt atccccaacg      1260 attacattat cccttgccac aaaacagttc aaccttaata cacttcttcc agaactaaag      1320
ggtaaaaaat cttcacaact atcctatcct aaagaaacgt ttttaactat cttaagtaat      1380
ctccataata ataataataa taataatata aaaaaaacaa tcaactatga cattactatt      1440
caggctgatc atgtaacatg ttggaaattt gatggatatc agtttatatg taacatacaa      1500
cctaaacctc agggtactca gattcatact aactgtaaaa atttttatga tggcagttta      1560
tcttcctcac ttttactatc taataggcac acaatacaat tagctataga aatatattcaa      1620 ctgtctgata taacaaatat tattacaaaa gaatatgaac taaaaggtaa agcttctggc      1680
acaagtcgtg ttaatggaca tggtgatact ttagcatcat ttctttcaag tctaaaaggt      1740
acaattgatt tatatgtaac tgatggatta gtaaaaaaaa cagcgtctga agctattcct      1800
ttttctatgc ttcatctaac atgtgacagt attggtcaac catcaaaggg aaataaatcc      1860
tctacaattc catataaagg gaagtggagt gcagagatat catcagcaag atggaatggc      1920
tcaattacaa tggatgggtt aatacaattt tcaaccactg actggctttc tattaaagca      1980 gaaacatac catcaaaagt tgtatgttct gtatctggcg tacaagctgt ggcttatgga      2040
ggatatcatt ttgacataga taatagttttt cttagcttct ctaattttca aggtgaaata      2100
catcctaaaa cagccctatc tggaacaatc aaaactagtt ctagtacaag taacacaaga      2160
caatgggagg ttctctcac tgtcatgaca caaaatctta gaatttatt aagtaaactt      2220 ggttatgaac caaaaaatat ttctccaact atgttgcaat attgtaaatt gcaaggagat      2280
atctttattt ctcctgcaac aattcgcctt acaaatatac agggaatatt agataataca      2340
ctgattaaat tttctctcaa tggattacag acaaaccctc caagttggac aggagatatc      2400
caactaagtt cattaaactt agataaatat ttactatcaa ttaaccaaaa taaactgaaa      2460
aaatcacagg aactctggcc gatagaattg ctgaataaag taaatattca atctacactg      2520
actctagctg agcttatcta tagaaaagtt ccatatacta atgtagtagt acccattagt      2580
cttaatcaag gaacattatc tatcactcca attacagcat cactatgtga tggaaaaaca      2640
gaagcaagct ttaaggcttg ccctctttca actaatggca atagtgcaca gatagatttt      2700
cattatattt caaaaggtgt ggatatgatt aaactaagta aaaaacgtca acaagaatat      2760
cttatttcag gccttggtac atttgttatt aatatacagt caatagcaaa atcatctata      2820
gatttcctta aaaatcttca agggaaatgg cgtattttta tccagaatgg ctatttcaaa      2880
agaaacacca ctactactca acaaaatttt agtaacattg gtgcaacagg aaatattata      2940
aatggtatta ttacaaataa taattttgca ataacagggc ctggaatggt aataacaggg      3000
agtggaaaaa ttgatcttcc tgaatggaat cttgactacc tcatcactat agatatggaa      3060
ggatttccta tagctatccc cataaaatat acaggaagta tagataaccc aaaaagaaca      3120
attaatgcgg ccaagttaat tcttagtact ataggttctc ttgggagaga tactatagga      3180
ttaatacaag atatttttc agctccactg aagttacttc ttccctaa                   3228
```

<210> SEQ ID NO 33
<211> LENGTH: 750
<212> TYPE: DNA
<213> ORGANISM: Lawsonia intracellularis

<400> SEQUENCE: 33

```
ttgaagaata ttataaatac tataattttt cctaagcaaa ggaacaaaaa aatgtcacaa     60
aaattttcta tgctacaact aatattattt tttttaactt ttatatttta ttcatatata    120
acagatagtt atgcagagtc tataccaata gtaaaagaat tacagcaatc atatcaatcc    180
attaaaaact tttctgcaac atttactcaa gaacttactc atcaagaaag tgggtccaaa    240
gaaacacgta ttgggaaact cttttttaaa aaaccacttc ttgtcagatg ggaaacaaac    300
acacctcatg aagaacttct tcttattaat accaatgctg tatgggatta tcttcctgat    360
gaaaaccttg tttataagta ctctacagat attgtaaaag attccacatc tattattcag    420
gttattactg gacaagtacg acttgataaa aacttctcaa ttattgaaaa taataataat    480
aataataatg agctaatctt ccttaaatta tacccaaaag aaccaacgac tcaaatggtt    540
gaggcatttt tatggattaa taaaaaaagt ttactcattc acaaagtaca atcaattgat    600
ttttatggaa atacaaatac tattactttt attaatatta cacccaatac tcatattgat    660
aataacatat ttcaatttac tccacctaaa gatgttacta tagaaaattt acaagattca    720
tctacaccag aacgaccact atttaattag                                     750
```

<210> SEQ ID NO 34
<211> LENGTH: 2466
<212> TYPE: DNA
<213> ORGANISM: Lawsonia intracellularis

<400> SEQUENCE: 34

```
atggcatacc tatctatttc aaaaaatcaa tgtaagtctt ttttaataac tctagtaact     60
atatttataa tgacatcaat accacaacta gctgaggctg ttgaacactt tgctaatggt    120
gtccccacag tagtacaaga tgttaatgtc ccagctgact catactttgg tggtgctgac    180
tcagctgtag gtccaaaccc aatagcttct actcacctta caatttctac aactcaaggg    240
tttggacaaa atgcactaga atttgttgtg ggtggtagcc ttgcaaatgg taatggaaat    300
ccagccaaca taaatggaga tatagtcctt attgttgaaa atacaaatac tcagaatagt    360
attattggtg gtagtatggc aaatgctgcc cctgtaacta ttggtggctc tatttttatg    420
actcttagaa atgttactgc agtagatcca atttttggtg gctctgtaga tgtacgcttt    480
ttcgcccaac agcaacctaa tgaggatcaa cttgtaggtg gagatattaa tataaatcta    540
gagaatgtaa caactccaga gttttatggt ctaggctacg caaatggtgt aatacctgtt    600
aacgtcctca atagaaattt tttggtagct gttcagggaa atataactac aaatatttct    660
aattctaaca ttgcaaccgt tatgttaggt tcacactatg atacaactat ggctgtagga    720
ggtaatggaa caataaatgt tgataattca acaattggtt atctttcagc tagcaatagt    780
agcgactttg ttaaccctga cttaacaaac actgttactt ttaatattgg tcccaacaac    840
agaatagcaa atatttttgc aagcaataat ggtgttatcc cacattttat tgtaaatatg    900
gatggatctg gaacagaaat acaagagtta acacttggta atgtaattcg aggtggcctt    960
gtacttactt cagagctaaa tctatctcaa ggaacaataa ataatttaat cactggtaat   1020
gaatattacg atagatcagg attaagaact actgtaaatg ttagaggagg tacaattggc   1080
gtattgactt caggaggttc tgactattca gaattaaact tcattcctgg agaaatatcc   1140
actatattag caacaaattc aataggtaac caagattttg catctctttc tcaagttaca   1200
atacaccaag gtgctgaaac tctttgggga atgagagatg aagtatttga acttcaaact   1260
aacaatctac agttaggtgg tgaactattt attcctgctg atggaactgg aggagtagcc   1320
```

| | |
|---|---:|
| ctaatcacaa atcatattat tgcaaattca ggtgtgataa ctccggtaaa tatgtctcca | 1380 |
| gaaaggatga cccctatcat tggattttta gaacctactg gtgaggtagc acagttaaca | 1440 |
| atatatggac cacttacagt taaccttagc cattctccag aaattcttgg gaaaattatt | 1500 |
| acacaaccta tccctattgc agttactaat agtgatgttt ttggtacttc taaactattt | 1560 |
| gtggaacata acacaaaagg actaatttgg agtgatatca ttttaatcc tcaagataaa | 1620 |
| acatggtatc taactaactt tagaggttct gaagacttct acggactttc agcagcacgg | 1680 |
| gaagcatcta attggttaag acaacaacat atctggagcc tacaacgtcg ctctaataaa | 1740 |
| ttattagatc atggtgtaga tgggttatgg atgaatgttc aaggtggtta tgaaaagctt | 1800 |
| gatgcagcaa ttggtgatgc taagatgcct tggattatgg caagcttagg atatgatttt | 1860 |
| atgcataagt taagtgattt ttataactta aaagcacttt atggattcgg atttggattt | 1920 |
| gctacaggta aaaataaatg gaataccata aactcaacta ctaatgatat ctacatgggg | 1980 |
| ctggttggtg cctatgttgg ccttatgcat gaagccacag gcctttatgg tacagtatcc | 2040 |
| ggacagtttg caactaaccg tacaaaaaca aaatgtacag gctttgatga aacctataac | 2100 |
| gaaatggagc attgatgagt ttaaaataaa cccacgtgga caagttatt ttgaacaatt | 2160 |
| atctaaacat cactttagtc aaccgttata ggtatctctg gagaatatga tttagattta | 2220 |
| agaagtaaaa taataaagct tcaagctagt gttgactgga ttaaaggcat ctctggtgac | 2280 |
| tttgcagcta atccgaagt tcttaatatg aagtttaaag ataaaaatga tactagtaca | 2340 |
| tttagaggaa cactgggtgc tagtgcacaa cttctagaaa actttgaagt tcaccttgat | 2400 |
| attttttggtg atcttggcaa tgataaaggt attggtggac aggtaggagc tacttataga | 2460 |
| ttctaa | 2466 |

<210> SEQ ID NO 35
<211> LENGTH: 2703
<212> TYPE: DNA
<213> ORGANISM: Lawsonia intracellularis

<400> SEQUENCE: 35

| | |
|---|---:|
| atgactaaag ttggtggtag taatccttt tcaacacttg catcaatggt tggctttagc | 60 |
| aaatcttctt ccagctcatc ttcaagtaag gtagctgaat taaaaagtaa atttgaagca | 120 |
| cttgggacac taacaaaagc aagtcctcgt cctgcaaatg gcactcagga tactaatcga | 180 |
| ttaagtgata gactatttag aggacactat acagttcctg ctaatacagc ttcaagagta | 240 |
| ggtggtcatc ttcagcgggt tgatgacaat aaaagtagca gttcagcagc taatgttgca | 300 |
| aaaagagctg cagcacattc ttcttttgca agttcaaacc caggactcca aggagctagc | 360 |
| ggttcttctt ctggaggaac aggcggaagt ataacgatc aagttaaaag taggggaatt | 420 |
| actgcaagga attttcgga ttctaataat aattctatag gatcagggtc aagcagtgga | 480 |
| agtatattag atcaggttag aagtcaaggt attactgcca gaggatcatc tatttcttct | 540 |
| ggtaatgcat caggtactag caatgttaat gatggaacaa gttcaagaga ttatggagct | 600 |
| aatgtccgta atactcgtga agatttgaa gctggtcctg gaggtgctca aggagagtct | 660 |
| cctggagtaa aagatgctaa agaagctact aaaggagtta gtgtttctaa tttaaggagga | 720 |
| atatttgaag gaagaggtgg tgcagataat aatcaagtag gtagaagctc tggtggagtt | 780 |
| tcaggagcat caggatcagg aggagctcaa gggacaggag gaacatcggg attaggtgga | 840 |
| gcacaaggta cattaggaag tggaggtctt gatggaggag gagtttcagg tgctgctggt | 900 |

```
ggaacttcag gcgcctcagg agccggagga gcaagaggta ctgctgatgg aataacgtct    960
cctggagcaa gagaagcaca agaaactatt aaaaatgctg gtgttagtgt aagagattta   1020
gctggaagat ttagtggagc tcaaggtaca agtggagctt caggagcagc gggagcttca   1080
ggagcctcag gagccggagg agcagctggt gcggcaggag gtggaggtct tgatagagga   1140
ggagtttcag gttctgctgg tggaacttca ggcacctcag gagccggagg agcaagaggt   1200
actgctgatg gaataacatc tcctggagca agagaagcac aagaaactat aaaaatgct   1260
ggtgttagtg taagagattt agctggaaga tttagtggag ctcaaggtac aagtggagct   1320
tcaggagctt caggagcagc tggtgtggca ggaatgccag caggtagtgg agatgttgtt   1380
gatggactaa gaagaggagg agaagatact gtcgatggat ttggaagaaa tcagggtagt   1440
ggtcctatcc ctagttctgc agattttgta gatggtccta taggcggtat acaaggagct   1500
ggaggagctt caggagcagc gggagcagct ggtgcttcag gagcagcggg agcttcagga   1560
gcagcagagc cacttcctac taatggtaca gatcagcaga tagctgaagt cgttgtaaga   1620
aatgcagaaa atggtcattt tgatggtatt gatttctcga cacagcctgg tggtgtagaa   1680
tcaaatacag gtagtatccc tggaacagat cttattgtcc aacgagacat cactcctgga   1740
gaacaaggag tgtataataa tctcagtgag atgggatcat ggatggatag ccctaatgct   1800
agtcctacaa atgcaccaga gtctcttaca gatgatcata gtgttttgac tacactactt   1860
aataataaag aaggcctaca agatactgtt ccttttcctc ttgctgtggg tgaaggcact   1920
gttgttacta aaactcttga tccagacatt gatacaagta agattaaaat cccacttgaa   1980
attgttttg gttctggaag tatgtatggt tctggtattg gaggaggtag tagtacaatt   2040
agctcctcaa tgtctgatga tggaagttct agcataggat caactacacg taaaaataga   2100
gcaggtgaaa taataagtag aattgcaatg aatcaatcac ctggcgctgg tagcgggggt   2160
caaactgtag ttggtggtct tggttctggt agtagtaata tcaatataag tggtggacgt   2220
ggtggtattg tttatggacc aatgcctaat gtgaatgtag tagctggaga tggccttaat   2280
agactacagc ttggtagtgg aataaatcca ttagcacttc ttcaggaaag aatggttaat   2340
tttctgctg ctcaactaga gcatttacat ggccaactta caggtatgat ggctatgatg   2400
gaagctatgc ctggcgtagc atttgaaggt gcaagtgtcc aaatgacatt acctgaacca   2460
ggtgatacac agactatgcc tagtataagg ctatcaggtt ttggagagcc aaggttgcgg   2520
gaaaatatag gacagccagg gcaacctcca acacaagaag catttgatgc attaaggaat   2580
ggtccactaa atggagtaag cgagttaatg agccaagttc aagaaatgat aactgtaagg   2640
agtgaaggaa gtatttcact aagcagaagt agtagtttat cagatttaag ttcagaaata   2700
taa                                                                 2703

<210> SEQ ID NO 36
<211> LENGTH: 552
<212> TYPE: DNA
<213> ORGANISM: Lawsonia intracellularis

<400> SEQUENCE: 36
atgaaaaaac tgattctaac tttttgcttta ttattagtaa caaatataac tactttttgct     60
tctgagcctt ttactctatc aagcccacaa atgaaaaatg gaactattgc aactaatcaa    120
gtttataata gttttggatg caaaggaaaa aatatttctc caagtctaga gtggaaaaat    180
cctcctgaag gaactaaaag ctttgctata actatgtttg atatagatgc accaacaggt    240
agtggatggt ggcattggat agtttataac attcctacat ccacttcctc attagtacta    300
```

```
ggagcaggaa atgatcctaa aaaacttccc aaaggtgcag ttcaatcaat aaatgacttt      360
ggttttattg gatttggagg accttgtcct ccagttggtg caaaacttca tcactatatt      420
tttactatct atgctctcaa tgtagagaca atggatttac cagcaacaac tatgcctgca      480
gctattggat tcaatattca tatgcatatg attgacaaag ctactttac tgctacttat       540 tctcgtaagt aa                                                          552
```

<210> SEQ ID NO 37
<211> LENGTH: 339
<212> TYPE: DNA
<213> ORGANISM: Lawsonia intracellularis

<400> SEQUENCE: 37

```
atgtctgcag ttgttgatag tatgacacca tttccttgtt cagaacatga tgagcttcca       60
gttataaatg aagcaacagc atgctgtgtc tttgataagg tagagagtta tatttcattg      120
cgtgatttaa agtaggaca acatgctcgt gttgtacgtg tgcaagcaga tggagagcta       180
ggaagacgta tccgtgatat gggtcttgtc ccagggacag aggtaactat tgttgggagg      240
gcacctctta aagatccagt tgcattaagg ttactaggtt ttactcttag tcttagaaat      300
agtgaagcag actatgtgat ggtatcacct atttcataa                             339
```

<210> SEQ ID NO 38
<211> LENGTH: 1197
<212> TYPE: DNA
<213> ORGANISM: Lawsonia intracellularis

<400> SEQUENCE: 38

```
gagatagtta tggctaatgt tagtggaatc cctgcaccac gattactttc cacaacaaat       60
caaatgacca atgcagctgc tggtaatact aatagagcta ccggtagtat gaacggtcgt      120
aatctcacac aaataaaaac acctcagtcc atgattgata atgcttcaga agaattaaca      180
acttctcttg aatctaaaag cagtgacgac tttgcaatta aagatcgtaa aagacaaggg      240
aaaggatctg attctctatt aaaaatggtt caagaatata cagagctgac gaatgatgat      300
acccgtaatg ctaaaagagc tatgttatcc caggtattac gtgcaagtca agttcacaa      360 gatgtactcg aaaaaacatt agaacaattt tctaataaaa cagatgcttg gcttctctt      420 gcagaaattg cacaagaata tggtgcagaa tctccacagc aacaggatt aaaatctgta      480 ttagatgcta tggagacatt agaaaatgag tttggtgatg aaattaaagc aggactaaaa      540
ggagctctaa attcaaaaga atttactgat ataggcagtg cagcacagtt aagagatctt      600
tatacaacaa cagtaactat aacagctgca cctgatgcag tgttagcaag acttcttgaa      660
gaatatgaga gtgatgatga tctggataga gccattgatt ccttctatc tacacttggt      720 ggagagcttg aatcagctga tccaagtatg gataaagtac atcttcaaag tgtaatgggt      780
gatattgaaa aaacacaaca acttcatagc tctcataaac aatgtactac agcccttagc      840
aggtggaaag agaaacataa aggtggggg gaaaatagta cactaactcc tttagaaatg      900
atgcgtgaac taattgcact aaaaaatgaa aatttattt ctccttcctc tatagataaa       960
attgttgatc aagctgatcc ccaagatatt gaaaagaag tccttttttt acaagagatg      1020
ttagctgctg taagaaaatt tccattatg gtatttgata atgtcgaaaa tcgtgtaaga      1080
gttatgggtg ctgtacaaga tgctgttgac gatgctgtaa gagagaaga tgaattcctc      1140 tttcaaaaag aacatcctga tgtaccacta caaccagatg aaaataatat acaataa       1197
```

<210> SEQ ID NO 39
<211> LENGTH: 2820
<212> TYPE: DNA
<213> ORGANISM: Lawsonia intracellularis

<400> SEQUENCE: 39

```
atgtataata taattaataa gcatcaaatc ataaaaattt tattattttc cttatgtgtt      60
ttctttttta cacttacaga aaaacaaaaa atttatgctg cagacgtctt ttttgagggc     120
agaaccgaaa ccttaatcaa tgtaaacaaa ccatttgatt cttttttttgg aggttctgac    180 tctacaatag gaaccccttga aacaggacct actaatctta ccttcacaac agtaggagcc    240
ttccgcaatt ctgttttcag aattattggt ggtggtaggt ctagttttaa caacccaaat    300
acagttaaag gcaatgttac tctaactgtt tataatactg atgtagaaag aataattggt    360
gcaggtatca gcaatagagg acttgtaacc gttactggct cagtaaatat gaagctagaa    420
aatgtttctg ttactagagg aatttatggt ggtgtctata ctcaaaatgg acatgtacta    480
ggctctatca acatgcattt gaaaaacgtc caaactccac tattaatagg ttctggagta    540
agcaatggac ctaatcgtat tactgtaaat ggagacataa acattgatgt tgaagactct    600
aggattcaat atgtaaacat tacaggagaa gtagatgcag gatataaaag aaatgctact    660
ctaactgtaa aaaatctac tgttgagctt ataaactctg gtagaggtaa tatcttaggt    720
aatctcaaaa tatctatagc agattcaaat ataaggggggt tatcaccagt agactttggt    780
tcttcagtat atgggacac atctataaat gtaattaatt ctcagattaa tgatattact    840
cttataccaa gggctggtgg aatgcttgta ggtcctgtta ccctagatat cacaagcagt    900
actatacaaa atatacaatg tgggcctgtc agtcaaaata atcaacttaa cacactaaat    960
gtaactgtta atactagtaa cattactaac ttaaaccttg gtagtgtcga aggtcataca   1020
atatcaacta cagcaactgt tactgatagt aatattacta accttaatgt cggaaccttc   1080
aatggacttg gagtaactga gaatgcctct gtaatcatta tagtggcaa tattactaac   1140 cttaatgtcg gaactaatgt aatagctgca gccacaacta ttaattcctc tgcgaccata   1200
cacgacggac ttattgcaaa ccttaccttga ggctcacaag gtaatggtcg tactatgata   1260
gctacagcaa atgttaatgg tggaactatt ggattattaa ctatgggttc agaaaacttc   1320
ataccaggca agaccaat tactgaatta gcaatactaa acatgtctgg tggattaatt   1380
gaaagaatta tcgtaggtaa tgccaactct tcaaccataa actttactcc tgggaagaga   1440
tcaattgtaa aaacaataaa tggtccagaa cttccatatt tagttaacat acaaaaaggt   1500
gctatgacac aatggggcac taaaaatatg cccttttttat tggatacaag aaatttaatc   1560
ttgtccggaa ctctgattac ctcaaatatt caactagctg atttatctat aaccaatcta   1620
tttgttgcta atggcggtac actagtacct agaaaattaa tacctgggaa ccaacctgtt   1680
atacagtttc ttggaggtcc tcaatcactc ttagttatcc atcaaccatt aaaagtaaat   1740
ttaagcttat caccaaaact tattggaagt agcatggtgc cacttgcttt tgtctctcaa   1800 tcttttttcat caccagatct ttttgttaaa caaactagaa gtggtctcat ttggagtgat   1860
cttgagtttg atccaacaac atctatttgg tatgttaata atatccaagc atctcaagat   1920
ttttactctt tctctattgc tcgtgagact actaactggc taagacaaca acatatatgg   1980
actctacaaa accgttcaag taaactttta gacaacgaac attatggact atggataaat   2040
gttcaaggtg gacatgaaag tcttgatact tctattggta gcaaagcaaa aatgccatgg   2100
ataatggcaa cagcaggata tgactatctt caacaactac caaggttaga tatgaaagcc   2160
```

-continued

```
ctttatggtc ttgcttttgg tgcttctaaa ggtaaaagta aatggtctag cgtcaactct    2220
acaaaaaatg atgctgagct aggtatggtt agtggttatg taggtcttat ccataacaaa    2280
actgggctct atagtacatt gaccttacaa cttgcgtcta gtaaattaca tactaattct    2340
acagggttct atagaaattt aaatggaca gaaacaactc caacagaagc acttgaactt    2400
ggatggaaat acactttcaa caacggtatt aaaatgaatc ctcgtggaca acttatttt    2460 gaacaaacat ctaaacacca ttttgattta ggaattcaaa atgataaggc tatattagat    2520
aaaagccagt taataacaag ttctcttggt attaccgttg aatataagct accagttacc    2580
acacctatta atctttatgc tggtattgaa aggataaaag gtcagtctgg aaactttgca    2640
attagttccc agagccttca aatgaagttc aagcatgaca atgatacaag tgtagttaga    2700
gcaacaatag gtacaaatat attattggga gaacatttta atattcactg tgatatattt    2760
ggagataaag gaaatgataa aggcattggt gggcaagcag gatttacata caaattttaa    2820
```

```
<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
aaccttagat ctattatcaa catctctgaa                                      30

<210> SEQ ID NO 41
<211> LENGTH: 33
<212> TYPE: DNA
<213> ORGANISM: Artificial Sequence
<220> FEATURE:
<223> OTHER INFORMATION: Primer

<400> SEQUENCE: 41
aaccttaagc ttttattcaa acagaccagg gat                                  33

<210> SEQ ID NO 42
<211> LENGTH: 30
<212> TYPE: DNA
<213> ORGANISM: Artificial Sequence
<220> FEATURE:
<223> OTHER INFORMATION: Primer

<400> SEQUENCE: 42
aaccttggat ccaaaagcgt agatgtagaa                                      30

<210> SEQ ID NO 43
<211> LENGTH: 30
<212> TYPE: DNA
<213> ORGANISM: Artificial Sequence
<220> FEATURE:
<223> OTHER INFORMATION: Primer

<400> SEQUENCE: 43
aaccttaagc tttttttgcga tgatgcggaa                                     30

<210> SEQ ID NO 44
<211> LENGTH: 30
<212> TYPE: DNA
<213> ORGANISM: Artificial Sequence
<220> FEATURE:
<223> OTHER INFORMATION: Primer
```

<400> SEQUENCE: 44
aaccttggat ccaaaagcgt agatgtagaa         30

<210> SEQ ID NO 45
<211> LENGTH: 33
<212> TYPE: DNA
<213> ORGANISM: Artificial Sequence
<220> FEATURE:
<223> OTHER INFORMATION: Primer

<400> SEQUENCE: 45
aaccttaagc ttttattttg cgatgatgcg gaa         33

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
aaactaggat ccttcgctcc agattacaac         30

<210> SEQ ID NO 47
<211> LENGTH: 33
<212> TYPE: DNA
<213> ORGANISM: Artificial Sequence
<220> FEATURE:
<223> OTHER INFORMATION: Primer

<400> SEQUENCE: 47
aaccaaaagc ttttattccc aggagccacc cag         33

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
aaccttagat ctaaaaagga agttaaaatc         30

<210> SEQ ID NO 49
<211> LENGTH: 33
<212> TYPE: DNA
<213> ORGANISM: Artificial Sequence
<220> FEATURE:
<223> OTHER INFORMATION: Primer

<400> SEQUENCE: 49
aaccttaagc ttttagtaca cataacggat ggt         33

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
aaccttagat ctggtaaaca gatccgtagc         30

<210> SEQ ID NO 51
<211> LENGTH: 33

<212> TYPE: DNA
<213> ORGANISM: Artificial Sequence
<220> FEATURE:
<223> OTHER INFORMATION: Primer

<400> SEQUENCE: 51
aaccttaagc tttcagatag agctgacgcg tgc                                33

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
aaccttagat ctatcacgtt ctacttcatc                                    30

<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53
aacctttcta gacggcagca gcagtttcag cgg                                33

<210> SEQ ID NO 54
<211> LENGTH: 30
<212> TYPE: DNA
<213> ORGANISM: Artificial Sequence
<220> FEATURE:
<223> OTHER INFORMATION: Primer

<400> SEQUENCE: 54
aaccttagat ctgaaagcat cccgattgta                                    30

<210> SEQ ID NO 55
<211> LENGTH: 33
<212> TYPE: DNA
<213> ORGANISM: Artificial Sequence
<220> FEATURE:
<223> OTHER INFORMATION: Primer

<400> SEQUENCE: 55
aaccttaagc ttttaattga acagtgggcg ctc                                33

<210> SEQ ID NO 56
<211> LENGTH: 30
<212> TYPE: DNA
<213> ORGANISM: Artificial Sequence
<220> FEATURE:
<223> OTHER INFORMATION: Primer

<400> SEQUENCE: 56
aaccttagat cttctagcag ctctaaggtt                                    30

<210> SEQ ID NO 57
<211> LENGTH: 34
<212> TYPE: DNA
<213> ORGANISM: Artificial Sequence
<220> FEATURE:
<223> OTHER INFORMATION: Primer

<400> SEQUENCE: 57

```
aaccttaagc ttagatttca gaggacaggt caga                              34
```

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58

```
aaccttagat ctgtagaaca cttcgcaaat                                   30
```

<210> SEQ ID NO 59
<211> LENGTH: 33
<212> TYPE: DNA
<213> ORGANISM: Artificial Sequence
<220> FEATURE:
<223> OTHER INFORMATION: Primer

<400> SEQUENCE: 59

```
aaccttaagc tttcagaagc ggtaggtagc acc                               33
```

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60

```
aaccttagat ctatgtctgc cgttgttgat                                   30
```

<210> SEQ ID NO 61
<211> LENGTH: 33
<212> TYPE: DNA
<213> ORGANISM: Artificial Sequence
<220> FEATURE:
<223> OTHER INFORMATION: Primer

<400> SEQUENCE: 61

```
aaccttaagc ttttaagaaa tcggagacac cat                               33
```

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62

```
aaccttggat ccaaacaaaa gatctacgcg                                   30
```

<210> SEQ ID NO 63
<211> LENGTH: 33
<212> TYPE: DNA
<213> ORGANISM: Artificial Sequence
<220> FEATURE:
<223> OTHER INFORMATION: Primer

<400> SEQUENCE: 63

```
aaccttaagc ttttagaatt tgtaggtgaa acc                               33
```

<210> SEQ ID NO 64
<211> LENGTH: 33
<212> TYPE: DNA
<213> ORGANISM: Artificial Sequence

```
<220> FEATURE:
<223> OTHER INFORMATION: Primer

<400> SEQUENCE: 64
aaccttagat ctggtaacac taatcgtgct act                              33

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
aaccttaagc ttctggatgt tgttttcatc                                  30

<210> SEQ ID NO 66
<211> LENGTH: 60
<212> TYPE: DNA
<213> ORGANISM: Artificial Sequence
<220> FEATURE:
<223> OTHER INFORMATION: Primer

<400> SEQUENCE: 66
aattcatcat catcatcatc atagcagcgg catcgaaggc cgcggccgct taattaatag    60

<210> SEQ ID NO 67
<211> LENGTH: 60
<212> TYPE: DNA
<213> ORGANISM: Artificial Sequence
<220> FEATURE:
<223> OTHER INFORMATION: Primer

<400> SEQUENCE: 67
aattctatta attaagcggc cgcggccttc gatgccgctg ctatgatgat gatgatgatg    60
```

LAWSONIA INTRACELLULARIS VACCINES

CROSS-REFERENCE TO RELATED APPLICATIONS

This application is a national stage entry under 35 U.S.C. §371 of PCT/US2009/061429 filed on Oct. 21, 2009, which claims priority to U.S. Application No. 61/107,858 filed on Oct. 23, 2008, the contents of which are hereby incorporated by reference in their entireties.

FIELD OF THE INVENTION

This invention relates to immunogenic compositions for immunization against *Lawsonia intracellularis*. Methods of protein expression, purification and use in preparation of immunogenic compositions are provided.

BACKGROUND OF THE INVENTION

Porcine proliferative enteropathy (PPE or PE), also referred to as Ileitis, is one of the most economically burdensome diseases of the swine industry. The disease has been reported to affect 12% to 50% of pigs on farms world-wide (Diseases of Swine, 7th Edition, 560-569 (1992)). Although the economic impact of PPE is felt largely by the swine industry, the disease has also been shown to affect multiple mammalian species, including monkey, rabbit, hamster, horse, ostrich, fox, ferret, rat and emu (Diseases of Swine, 7th Edition, 560-569 (1992)). In animals exhibiting proliferative hemorrhagic enteropathy (PHE), the acute form of PPE, the death rate is as high as 50 percent, and pregnant animals infected often abort within the first 6 days (Diseases of Swine, 7th Edition, 560-569 (1992)). The causative agent for PPE was first determined and isolated by Lawson et al. (*Journal of Clinical Microbiology* 31(5):1136, (May 1993)). The bacteria isolated by Lawson et al. were obligate, intracellular, gram-negative curved rods which tolerated oxygen only at reduced pressure from atmospheric tension and grew in vivo only in enterocytes. Lawson et al. isolated two strains of the bacteria and deposited them as NCTC 12656 and NCTC 12657.

Further phylogenetic characterization and naming of these bacteria was performed by McOrist et al. (*International Journal of Systematic Bacteriology*, 45(4):820-825, (October 1995)). The causative agent of PPE was determined to be the obligate intracellular bacterium, originally found by Lawson et al., now designated *Lawsonia intracellularis* (LI). This organism is a gram-negative, flagellated bacterium that infects immature epithelial cells of the intestinal crypts, called enterocytes.

In the early stages of infection, the bacterium associates with the cell membrane and quickly enters the crypt epithelial cells via an entry vacuole (McOrist, S., et al., *The Canadian Journal of Veterinary Research*, 70(2):155-159, (April 2006)). This vacuole rapidly breaks down and the bacteria flourish and multiply freely in the cell cytoplasm. One of the distinguishing features of this disease is the uncontrollable proliferation of crypt epithelial cells which results in thickening of the mucosal lining of the small, and sometimes the large, intestine. In pigs, infection with LI causes diarrhea, stunted growth and in some cases sudden death.

Proliferative enteropathies are a group of diseases with widely differing appearances and symptoms, one member of which is PPE (Diseases of Swine, 7th Edition, 560-569 (1992)). Several different forms of PPE (acute, chronic, necrotic and subclinical) can also be distinguished; however they all have the common underlying pathogenic cause being *Lawsonia intracellularis*. The disease initially develops as a progressive proliferation of the immature intestinal epithelial cells which are infected by *Lawsonia intracellularis*. This form of the disease is characterized by the presence of bloody or blood-tinged diarrhea, blood clots and sudden death. Porcine intestinal adenomatosis (PIA) is considered the chronic and most common form of the disease, which is seen in growing pigs (nursery to late finishing stage). Proliferative hemorrhagic enteropathy (PHE) is considered the acute form of the diseases, affecting the terminal ileum and colon of adult pigs (4-12 months of age). PHE develops from PIA and is distinguished by severe bleeding into the lumen of the intestine from the pre-existing PIA lesions. This form of the disease is observed in the terminal ileum and upper part of the proximal colon and is characterized by extensive thickening of the mucosal lining of the affected areas with little or no inflammation in the mucosal surface. Necrotic enteritis is another form of the disease, which is characterized by severe thickening of the ileum along with presence of yellowish necrotic lesions in the ileum. Another form of the disease that has been described in pigs with *Lawsonia* infections is a subclinical disease producing carrier animals without overt signs of disease.

Growth of *Lawsonia intracellularis* in cell culture requires an environment that contains an unusual gas mixture (oxygen, carbon dioxide, nitrogen and hydrogen). In addition, the bacteria do not display observable cytopathic effects in the host cells. These factors underscore the importance of researching unconventional technologies in order to develop efficacious vaccines to protect against the disease caused by *Lawsonia*, but which do not require the cultivation of the bacteria. One such approach involves the application of recombinant DNA technology to develop a subunit vaccine. Previous studies have utilized ARTEMIS and TB-parse to annotate the fully sequenced *Lawsonia* genome (US2006/0024696).

Despite these advances, development of subunit vaccines has been hampered by the lack of information on the identity of protective antigens that can be used as the basis for a vaccine. The present invention addresses these and other needs.

The references cited herein are intended to be viewed as references only and are not intended for any other purpose. No inference should be made that the information provided and references cited are prior art merely because they are in this document.

BRIEF SUMMARY OF THE INVENTION

The present invention is directed toward polypeptides and polynucleotides useful as subunit vaccines for protection against *Lawsonia intracellularis* without the need for in vitro culture. The present invention provides for compositions comprising one or more polypeptides of invention (e.g., SEQ ID NOs: 1-13). These compositions can also be immunogenic compositions, which further comprise a pharmaceutically acceptable adjuvant. The present invention also provides the immunogenic compositions that further contain one or more antigenic components of the following microorganisms: *Mycoplasma Hyopneumoniae, Erysipelas* spp, *salmonella, H. parasuis, clostridium* spp, *streptoccous suis, brachyspira* spp, *bordetella, pasteurella, E. coli*, coronavirus, parvovirus, PRRS, Circovirus, and SIV. In other embodiments, the present invention provides for compositions comprising one or more polynucleotides which encode the polypeptides of the invention (e.g., SEQ ID NOs: 27-39). These compositions can also be immunogenic compositions, which further comprise a pharmaceutically acceptable adjuvant. In addition, the present invention provides immunogenic compositions comprising inactivated *Lawsonia* (bacterin) and an appropriate adjuvant.

The present invention further provides methods of inducing a protective immune response against *Lawsonia* in an animal, wherein the method comprises administering the composition comprising the bacterin, polypeptides or polynucleotides of the present invention to the animal. In a specific embodiment the animal is a pig. The route of administration is not critical to the invention. Methods of administration useful in the invention include scarification, intramuscular injection, subcutaneous injection, intraperitoneal, intranasal administration or oral administration. The present invention further provides methods for specific detection of antibodies reactive with *Lawsonia* in a biological sample obtained from an animal. The detection method of the present invention comprises the steps of contacting the biological sample with a *Lawsonia* antigen of the present invention and detecting antigen-antibody binding between the *Lawsonia* antigen and an antibody in the biological sample. In a specific embodiment, the biological sample is from blood. The present invention also provides a kit containing one or more *Lawsonia* antigens of the invention, as well as an instruction pamphlet for inducing a protective immune response against *Lawsonia* in pigs.

DETAILED DESCRIPTION

Definitions of the Invention

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic chemistry described below, are those well known and commonly employed in the art. Standard techniques, or modifications thereof, are used for chemical syntheses and chemical analyses.

One of skill will recognize that the *Lawsonia* polypeptides of the invention can be varied without loss of immunogenicity. Thus polypeptides of the invention include polymorphic variants, alleles, and mutants that: (1) have an amino acid sequence that has greater than about 80% amino acid sequence identity, 85%, 90%, specifically 91%, 92%, 93%, 94%, 95%, 96%, 97%, 98% or 99% or greater amino acid sequence identity, specifically over a region of at least about 25, 50, 100, 200, 500, 1000, or more amino acids, to the polypeptides exemplified here. Such variants will specifically bind to antibodies, e.g., polyclonal antibodies, raised against an immunogen comprising an amino acid sequence exemplified here. Another means to identify variants of the invention is that the DNA encoding them specifically hybridize under stringent hybridization conditions to the nucleic acid sequences shown here or have a nucleic acid sequence that has greater than about 90%, specifically greater than about 91%, 92%, 93%, 94%, 95%, 96%, 97%, 98%, 99%, or higher nucleotide sequence identity to the exemplified sequences.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more specifically less than about 0.01, and most specifically less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture of (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, more specifically the hybridization is 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The use of singular terms for convenience is in no way intended to be so limiting. Thus, for example, reference to a composition comprising "a polypeptide" includes reference to one or more of such polypeptides. In addition, reference to an "antibody" includes a reference to a plurality of antibodies. Furthermore, reference to an "organism" includes a reference to a plurality of organisms.

The use of the term "amplification primer" or "PCR primer" refers to oligonucleotides comprising either natural or synthetic nucleotides that can serve as the basis for amplification of a specific nucleic acid sequence. They include both polymerase chain reaction (PCR) primers and ligase chain reaction primers.

The term "antibody" refers to a polypeptide substantially encoded by an immunoglobulin gene or genes, that is capable of interacting with and binding to a specified protein or antigen contained in a composition comprising, but not limited to, one or more proteins and/or antigens.

The term "adjuvant" is defined as one or more substances that cause stimulation of the immune system. In the context of the present application, adjuvant is used to enhance or stimulate an immunogenic response to one or more immunogenic composition antigens/isolates.

The term pig or swine includes all domesticated porcine species, unless otherwise indicated.

Methods of Generating Synthetic Genes

The present invention provides novel *Lawsonia* proteins with immunogenic properties. Any of the presently available bioinformatics applications can be employed to determine putative proteins. A further step of a bioinformatics screen using a computer program whose algorithm can be used to predict the cellular location of the putative *Lawsonia* protein sequences was used. While any bioinformatics program that predicts location and/or function of putative proteins can be employed, PSORT is conveniently used for this purpose. Such programs are useful to obtain information regarding which of the thousands of putative *Lawsonia* proteins are located on the cell surface, and therefore potentially useful in vaccines. The proteins of the present invention are listed as SEQ ID NOs: 1-13. The nucleic acids encoding these proteins are presented in SEQ ID NOs: 14-39.

The invention further provides the next step of synthesizing the putative genes. Genes can be synthesized via standard methodologies. Once obtained, the sequences are then inserted into expression vectors using standard methods known to those of ordinary skill in the art. It will be appreciated that codon usage can be optimized to obtain optimal protein expression in the desired host cell, e.g., *E. coli*.

Methods of Amplification

Once desired sequences are identified, PCR amplification can be used to prepare polynucleotide sequences of interest. PCR amplification can be performed using standard methods by anyone of basic skill in the art. Many methods of PCR amplification can be performed and any of these can be used for the present invention.

Methods of Cloning of *Lawsonia* Genes

*Lawsonia* genes can be cloned using standard recombinant DNA technology methods by anyone of basic skill in the art. Many vectors would suffice for the methods of the present invention. The exact vector used is not critical to the invention. Typically, the expression vector is selected and designed to provide efficient protein expression in the desired host cell, e.g., *E. coli*.

Expression and Purification of Proteins

The present invention provides a method for the expression and purification of novel *Lawsonia* polypeptides. Well known methodologies for protein expression and purification of proteins can be used in the present invention.

The proteins of the invention can be expressed in a variety of host cells, including *E. coli*, other bacterial hosts, yeast and insect cells. The host cells can be microorganisms, such as, for example, yeast cells, bacterial cells, or filamentous fungal cells. Examples of suitable host cells include, for example, *Pseudomonas* sp., *Escherichia* sp. (e.g., *E. coli*), *Bacillus*, among many others. Suitable yeast cells can be of any of several genera, including, for example, *Saccharomyces* (e.g., *S. cerevisiae*), and *Candida*. Suitable insect cells can be of several varieties, including, for example, Sf9 and Hi-5 cells.

After obtaining the synthetic genes encoding the polypeptides of the present invention, these synthetic genes can be cloned into expression vectors designed for expression in the desired host cell. Cloning of DNA sequences into expression vectors is a common and well know method to those skilled in the art. Any number of specific methods and vectors can be employed. The vector need only contain the polynucleotide sequence encoding the polypeptides of the present invention and the elements necessary for expression in the desired host cell, e.g., *E. coli*. Other specific vectors that can be used for the invention include baculovirus vectors capable of containing the polynucleotide sequence encoding the polypeptides of the present invention and the elements necessary for expression in the desired insect cell type, e.g. Sf9 or Hi-5.

A construct that includes a polynucleotide of interest operably linked to gene expression control signals that, when placed in an appropriate host cell, drive expression of the polynucleotide is termed an "expression cassette." Expression cassettes that encode the proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement, being replicated as the cell undergoes DNA replication.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media. Often, the vector will have one selectable marker that is functional in, e.g., *E. coli*, or other cells in which the vector is replicated prior to being introduced into the host cell. A number of selectable markers are known to those of skill in the art.

Expression of the protein can be induced by selecting vectors that comprise inducible promoters. For example, an IPTG inducible vector (pMAL-c2X and pET-23a(+)) can be employed, transformed into the *E. coli*, and expression induced by IPTG. These methods are well known and have been shown to be highly useful for protein expression.

In some embodiments, the polynucleotide sequences encoding the polypeptides of the present invention are optimized for codon usage in the desired host in order to optimize protein expression. For example, the original *Lawsonia* genomic polynucleotide sequences are listed as SEQ ID NOs: 27-39; the *E. coli* codon optimized variants of these nucleic acid sequences are listed as SEQ ID NOs: 14-26.

Methods of Detection and Purification of Expressed Proteins

The proteins of the invention can be purified according to standard procedures in the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol.* 182*: Guide to Protein Purification*., Academic Press, Inc. N.Y. (1990)). Substantially pure compositions of at least about 70% to 90% homogeneity are envisioned, and more specifically 98% to 99% or are envisioned.

To facilitate purification, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the proteins of the invention, and corresponding detection systems are known to those of skill in the art, and several are commercially available (e.g., "FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468,374, filed May 5, 2003, herein incorporated by reference in its entirety.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the proteins of the invention without diminishing their immunogenic activity. Some modifications may be made to facilitate the cloning or expression. Such modifications are well known to those of skill in the art and include, for example, the addition of codons at either terminus of the polynucleotide to provide, for example, a methionine added at the amino terminus to provide an initiation site, or additional amino acids (e.g., poly His) placed on either terminus to create conveniently located restriction enzyme sites or termination codons or purification sequences.

Vaccine Composition and Use:

Protein immunogens of the present invention may be expressed, concentrated and purified from expression hosts such as *E. coli* using various methods known to one of skill in the art. Purified protein immunogens can be formulated into vaccines containing an immunologically effective amount of one or more of the proteins of the invention and an appropriate pharmaceutical carrier. Thus, proteins of the invention can be administered individually or in combination either in a single composition or multiple compositions. The formulated vaccines may be combined with a pharmaceutically acceptable adjuvant. The formulated vaccines may be an aqueous solution, a suspension or an emulsion. An immunologically effective amount of each immunogen in the vaccines of the present invention is determinable by methods known in the art without undue experimentation. In a specific embodiment of the invention, the general quantity of each immunogen will be between 5 µg and 500 µg of purified protein. In a specific embodiment of the present invention, the amount will be between 10 µg and 250 µg. In an even more specific embodiment of invention the amount will be between 50 µg and 200 µg of each protein.

The adjuvant can be any pharmaceutically acceptable adjuvant. In a some embodiments the adjuvant is aluminum hydroxide. In others the adjuvant is aluminum phosphate. In yet another embodiment the adjuvant is Emunade®. Emunade® is an adjuvant consisting of a combination of oil, water and aluminum hydroxide. In yet another embodiment the adjuvant is Quil A. In yet another embodiment the adjuvant is Quil A plus cholesterol.

In some embodiments, ISCOM is used as an adjuvant. ISCOM is an acronym for Immune Stimulating Complex and the technology was described by Morein et al. (Nature 308: 457-460 (1984)). ISCOMs are formed as follows. The polypeptides are solubilized using standard methods, such as with a non-ionic detergent (e.g., Mega-9, Triton X-100, Octylglucoside, Digitonin, Nonidet P-40, $C_{12}E_8$, Lubrol, Tween-80). A lipid mixture is added to assist ISCOM formation. The lipid mixture can include a phosphatidyl choline and a synthetic cholesterol. In some embodiments, the mixture is first treated with non-ionic detergent at room temperature with stirring, then the lipid mixture (equal parts phosphatidyl choline and cholesterol, for example) is added and stirring continued. Quil A (a purified glycoside of saponin) is added to polypeptide composition and stirring is continued. Then the non-ionic detergent is removed (for example, by diafiltration with ammonium acetate). The matrix of the ISCOM is formed by Quil A. The morphology of an ISCOM particle, as viewed by electron microscopy, shows a typical cage like structure of approximately 35 nm in size. The ISCOM formation stage can be refined by the use of tangential flow diafiltration. ISCOMs present purified antigens in a multimeric form based on the ability of Quil A to spontaneously form micelles at a critical concentration and by a hydrophobic/hydrophilic link that entrap the purified antigens. Formation of ISCOMs can be verified by electron microscopy to verify that the typical cage-like structures have been formed. The Quil A can be added to give a final concentration of about 0.01 to 0.1%. In some embodiments, the final concentration is about 0.05%.

The composition containing the proteins of the invention and an adjuvant can be administered through one of the following standard methods: scarification, intramuscular injection, subcutaneous injection, intraperitoneal, intranasal administration or oral administration. In a specified embodiment, the compositions containing one or more of the polypeptides of the present invention is administered by intramuscular injection. In a typical embodiment of the invention, the polypeptides are administered at dosages between 10 µg and 1000 µg. In another embodiment the polypeptides are administered at dosages between 10 µg and 500 µg. In yet another embodiment the polypeptides are administered at dosages between 100 µg and 250 µg.

After administration of the composition containing one or more of the polypeptides of the present invention, the efficacy of administration of the compositions in eliciting a protective immune response can be examined.

A further embodiment of the present invention provides for compositions containing the polynucleotides of the present invention. The present invention provides recombinant viral vectors comprising a foreign DNA sequence inserted into the viral vector genome. Viral vectors contemplated by the present invention consist of, but are not limited to, adenoviral vectors, swinepox viruses, PRRS viral vectors and pseudorabis viral vectors. In another embodiment, the present invention provides bacterial vectors comprising a foreign DNA sequence inserted into the bacterial vector genome. Bacterial vectors contemplated by the present invention include, but are not limited to, *Salmonella cholerasuis* vectors, *Salmonella typhimurium* vectors, *E. coli* vectors, and *Lactobacillus* vectors. The polynucleotides of the present invention, listed as SEQ ID NOs:27-39, can be recombinantly inserted into viral and or bacterial vectors through standard procedures well known to one of skill in the art. In another specific embodiment, the recombinant viral vectors are capable of replication in the animal to which the recombinant vector is administered. In a specific embodiment, the vectors are one of those listed above; however, this is not an exhaustive list, and the use of any vector capable of expression in an animal is contemplated by the invention.

This invention further provides foreign DNA sequences from *Lawsonia*, as listed in SEQ ID NOs:27-39, or foreign RNA derived from these sequences which encodes a polypeptide. In a specific embodiment, the polynucleotides of the invention are recombinantly inserted into an open reading frame (ORF) of the viral or bacterial vector. For purposes of the invention, an ORF is defined as a segment of DNA in the recombinant vector that contains the codons that can be transcribed into RNA, and that can further be translated into an amino acid sequence or polypeptide; the ORF does not contain a termination codon. The recombinant vectors of the present also contain promoters. For purposes of the invention, a promoter is defined as a specific DNA sequence on the recombinant DNA vector to which the RNA polymerase binds and at which transcription of the foreign and/or recombinantly inserted DNA sequences begins. In a specific embodiment the polynucleotide sequence is under the control of a promoter.

In one embodiment, the *Lawsonia* polypeptide translated from the RNA transcribed from the recombinant vector is an immunogenically active antigen in the animal in which it is expressed. In a more specific embodiment, this polypeptide is able to induce antibody production in said animal. In a even more specific embodiment of the present invention said animal is a pig.

The invention further provides for a recombinant adenovirus vector capable of replication and which contains a foreign DNA polynucleotide, as listed in SEQ ID NOs:27-39, that encodes an antigenic polypeptide that is from *Lawsonia*. The invention further provides for a recombinant adenovirus vector capable of replication which contains a foreign DNA polynucleotide that encodes an antigenic polypeptide, listed as SEQ ID NOs:1-13, that is from *Lawsonia*.

The invention further provides for a recombinant swinepox virus vector capable of replication and which contains a foreign DNA polynucleotide, as listed in SEQ ID NOs:27-39, that encodes an antigenic polypeptide that is from *Lawsonia*. The invention further provides for a recombinant swinepox virus vector capable of replication which contains a foreign DNA polynucleotide that encodes an antigenic polypeptide, listed as SEQ ID NOs:1-13, that is from *Lawsonia*.

The invention further provides for a recombinant PRRS virus vector capable of replication and which contains a foreign DNA polynucleotide, as listed in SEQ ID NOs:27-39, that encodes an antigenic polypeptide that is from *Lawsonia*. The invention further provides for a recombinant PRRS virus vector capable of replication which contains a foreign DNA polynucleotide that encodes an antigenic polypeptide, listed as SEQ ID NOs:1-13, that is from *Lawsonia*.

The invention further provides for a recombinant pseudorabies virus vector capable of replication and which contains a foreign DNA polynucleotide, as listed in SEQ ID NOs:27-39, that encodes an antigenic polypeptide that is from *Lawsonia*. The invention further provides for a recombinant pseudorabies virus vector capable of replication which contains a foreign DNA polynucleotide that encodes an antigenic polypeptide, listed as SEQ ID NOs:1-13, that is from *Lawsonia*.

The invention further provides for a recombinant *Salmonella cholerasuis* vector which contains a foreign DNA polynucleotide, as listed in SEQ ID NOs:27-39, that encodes an antigenic polypeptide that is from *Lawsonia*. The invention further provides for a recombinant *Salmonella cholerasuis* vector which contains a foreign DNA polynucleotide that encodes an antigenic polypeptide, listed as SEQ ID NOs:1-13, that is from *Lawsonia*.

The invention further provides for a recombinant *Salmonella typhimurium* vector which contains a foreign DNA polynucleotide, as listed in SEQ ID NOs:27-39, that encodes an antigenic polypeptide that is from *Lawsonia*. The invention further provides for a recombinant *Salmonella typhimurium* vector which contains a foreign DNA polynucleotide that encodes an antigenic polypeptide, listed as SEQ ID NOs:1-13, that is from *Lawsonia*.

The invention further provides for a recombinant *E. coli* vector which contains a foreign DNA polynucleotide, as listed in SEQ ID NOs:27-39 that encodes an antigenic polypeptide that is from *Lawsonia*. In some embodiments, SEQ ID NOs:14-26, which are optimized for expression in *E. coli*, are used. The invention further provides for a recombinant *E. coli* vector which contains a foreign DNA polynucleotide that encodes an antigenic polypeptide, listed as SEQ ID NOs:1-13, that is from *Lawsonia*.

The invention further provides for a recombinant *Lactobacillus* vector which contains a foreign DNA polynucleotide, as listed in SEQ ID NOs:27-39, that encodes an antigenic polypeptide that is from *Lawsonia*. The invention further provides for a recombinant *Lactobacillus* vector which contains a foreign DNA polynucleotide that encodes an antigenic polypeptide, listed as SEQ ID NOs:1-13, that is from *Lawsonia*.

The polynucleotide containing vector immunogens can be formulated into vaccines containing an immunologically effective amount of one or more of the polynucleotide vectors of the invention and an appropriate pharmaceutical carrier. Thus, polynucleotides of the invention can be administered individually or in combination either in a single composition or multiple compositions. The formulated vaccines may be combined with a pharmaceutically acceptable adjuvant. The formulated vaccines may be an aqueous solution, a suspension or an emulsion. An immunologically effective amount of each immunogen in the vaccines of the present invention is determinable by methods known in the art without undue experimentation. The polynucleotide immunogens of the present invention can be administered as viral or bacterial particles. In a specific embodiment the viral or bacterial particles containing the polynucleotide sequences of the present invention can be administered at a concentration of $10^4$ to $10^9$ particles per dose. In a more specific embodiment the viral or bacterial particles containing the polynucleotide sequences of the present invention can be administered at a concentration of $10^5$ to $10^8$ particles per dose. In an even more specific embodiment, the viral or bacterial particles containing the polynucleotide sequences of the present invention can be administered at a concentration of $10^6$ to $10^7$ particles per dose.

The immunogenic compositions of the invention may also comprise nucleic acids encoding the immunogenic polypeptides in the absence of a viral or bacterial vector. See, e.g., Wolff et. al. (1990) Science 247:1465-1468; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

In another embodiment of the invention, the general quantity of each polynucleotide immunogen will be between 1 μg and 1000 μg of each polynucleotide per dose. In a specific embodiment of the present invention, the amount will be between 10 μg and 500 μg of each polynucleotide per dose. In an even more specific embodiment of invention the amount will be between 25 μg and 250 μg of each polynucleotide per dose.

One convenient measure of efficacy is based on significant ($p<0.05$) reduction in prevalence and severity of macroscopic and microscopic lesions in the ileum of vaccinated versus control animals. For example, a significant reduction in ileum lesions scores between vaccinated animals and control animals (t-test, $p<0.05$) is one useful measure of efficacy. Furthermore, a significant reduction in the colonization of vaccinated animals versus control as determined by immunohistochemical staining of affected ileal tissues can also be detected. Methods for carrying out such assays are well known.

The present invention also encompasses combination vaccines comprising immunogens of the present invention and at least one antigenic component of other pathogens including, but not limited to, *Mycoplasma Hyopneumoniae*, *Erysipelas* spp, *salmonella*, *H. parasuis*, *clostridium* spp, *streptoccous suis*, *brachyspira* spp, *bordetella*, *pasteurella*, *E. coli*, coronavirus, parvovirus, PRRS, Circovirus, and SIV.

Vaccines of the present invention may be administered to animals using a variety of methods including, but not limited to: scarification, intramuscular, subcutaneous, intranasal, intraperitoneal, or oral methods.

In another embodiment of the invention, the immunogenic compositions can encompass inactivated bacteria, termed "bacterin." The method of inactivation is not critical to the invention. Inactivation can occur after contaminating or interfering material is removed. Inactivation can include the use of known inactivating agents. Such inactivating agents include, but are not limited to: UV irradiation, formaldehyde, glutaraldehyde, binary ethyleneimine (BEI), and beta-propiolactone. In some embodiments BEI is used because it is known to destroy the viral nucleic acid without damaging the viral proteins. In addition, BEI is not affected by protein content and temperature. Inactivating agents are used at a concentration high enough to inactivate every bacterium in the solution. For example, BEI can be used at a final concentration of between about 0.5 mM and 10 mM. The pH and temperature can be chosen to ensure the resulting inactivated bacteria are still immunogenic. Inactivation can proceed with an appropriate amount of agitation to ensure that the agent contacts all the bacterial particles in the solution.

After inactivation, the inactivating agents can be removed using methods including, but not limited to, inactivation of the inactivating agent, precipitation of the inactivating agent, filtration of the inactivating agent, and chromatography, or a mixture of these methods. For example, BEI can be inactivated by the addition of sodium thiosulfate. Residual BEI can also be separated from the bacteria using size exclusion methods.

Detection of Serological Response

Methods of identifying whether the immunogenic composition induces a serological response are also well known in the art. For example, one can inject a test animal with the immunogenic composition/vaccine and identify antiviral antibodies in the blood serum. Methods of identifying whether the immunogenic composition is protective are well known in the art and include immunization of a test animal with the immunogenic composition, followed by inoculation with a disease-causing virus and identification of the presence or absence of symptoms of the disease.

The polypeptides and polynucleotides of the invention can also be used in diagnostic applications for the detection of *Lawsonia* in a biological sample. The presence of parasites can be detected using several well recognized specific binding assays based on immunological results. For instance, labeled monoclonal antibodies to polypeptides of the invention can be used to detect *Lawsonia* in a biological sample. Alternatively, labelled polypeptides of the invention can be used to detect the presence of antibodies to *Lawsonia* antigens in a biological sample. The sample can blood, urine, intestinal mucosa or any other bodily fluid likely to contain antibodies.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with 3H, 125I, 35S, 14C, or 32P labelled compounds or the like. Non radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

The presence of antibodies to *Lawsonia* can be carried out using well known techniques such as Western blots, ELISA, and the like. The polypeptides of the invention can thus also be used to detect *Lawsonia* infection in an animal using these techniques.

EXAMPLES

The following examples are offered to illustrate, but not to limit the claimed invention.

Example 1

Methods of Generating Synthetic Genes

The present invention provides methods for predicting protein sequences based on genomic DNA. The present invention further provides methods for predicting antigenic utility of the aforementioned predicted proteins. Prior to the methods encompassed by the present invention, the complete DNA sequence of the *Lawsonia intracellularis* chromosome and plasmids has been determined and deposited electronically in Genbank. In order to identify possible protective antigens, bioinformatics methods were applied to the published *Lawsonia* genomic and plasmid DNA sequences.

Kapur et al. previously reported the use of bioinformatics approaches to obtain putative or hypothetical open reading frames in order to predict *Lawsonia* protein sequences (US2006/0024696). The present invention provides further methods of verification of the hypothetical proteins found. The program PSORT was used to determine the cellular locations of the putative or hypothetical *Lawsonia* proteins. The PSORT program functions by recognizing the localization signal in proteins, and provides information as to whether a given protein may be found intracellularly (i.e. within the cell cytoplasm), in the cytoplasmic membrane, in the outer membrane or in multiple locations. Therefore, the previous methodology was combined with PSORT to obtain sequences that would be potentially immunogenic.

Based on the putative amino acid sequences obtained from the bioinformatics methodologies, the 13 candidate genes were analyzed using the software, Signal P 3.0, from the Center for Biological Analysis CBS. The software allows identification of the probable location of signal sequence cleavage points. Putative mature *Lawsonia* protein sequences, lacking the proposed putative signal sequence, were provided to DNA 2.0, Inc. (Menlo Park, Calif., USA). The DNA encoding each gene was then synthesized, optimizing codon usage for expression in *E. coli*. These synthetic *Lawsonia* genes were then cloned into Invitrogen Gateway Entry Vector, pDONR221. All synthetic gene constructs were sequenced on both strands, to ensure accuracy.

Example 2

Methods of PCR Amplification

Using the aforementioned methods, 13 putative proteins sequences were selected for further analysis. The DNA encoding the 13 amino acid sequences was isolated and amplified by the polymerase chain reaction methodology. Two PCR reactions were employed for amplification of the DNA encoding the 13 putative protein sequences.

PCR amplification reactions were performed using KOD Hot Start DNA Polymerase (Novagen), in 50 µL reaction mixtures which contained 100 ng template DNA (synthetic gene sequences listed as SEQ ID NOs:14-26), 15 µM of each primer, 0.2 mM each of dATP, dGTP, dCTP, and dTTP, and 1 mM MgSO$_4$ by 35 cycles of heating and cooling. All primers used for amplification of the genes are contained in the sequence listing as SEQ ID NOs:40-65.

PCR amplifications were performed using Accu-Primer GC Rich DNA Polymerase (Invitrogen) in 50 µL reaction mixtures which contained 200-500 ng template DNA (synthetic gene sequences listed as SEQ ID NOs:14-26), 10 μM of each primer, 0.2 mM each of dATP, dGTP, dCTP, and dTTP, and 1.5 mM MgSO$_4$ by 30 cycles of heating and cooling. All primers used for amplification of the genes are contained in the sequence listing as SEQ ID NOs:40-65.

Example 3

Cloning of *Lawsonia* Genes

For cloning into pUEX2-M3, an isolated PacI/BamHI fragment from plasmid pDONR-G07501, was digested with EcoRI, and the resulting EcoRI/BamHI fragment purified from a 2.0% agarose gel using QIAquick spin columns (QIAGEN, Valencia, Calif.). The purified DNA fragment containing the synthetic *Lawsonia* gene Law 0460-PEBP (SEQ ID NO:23), was then inserted into EcoRI/BamHI sites of the pUEX2-M3 plasmid. An N-terminal His-tag, generated by annealing two complimentary synthetic oligomers together, was added to this plasmid at the EcoRI site. The sequence listing contains the sequences of the two DNA oligomers used to create the His-tag adaptor as SEQ ID NOs: 66-67.

For cloning into either pET-23a(+) or pMAL-c2X plasmid vectors, the synthetic *Lawsonia* gene PCR products were first purified from 1.0-2.0% agarose gels by use of a QIAEX II Gel Extraction Kit or QIAquick spin columns (QIAGEN, Valencia, Calif.), then digested either with BglII or BamHI and HindIII, and inserted into BamHI/HindIII sites of either plasmid vector (Table 1). The one exception to this was with Law 0050-AsmA (SEQ ID NO:19), which contained an internal HindIII site, so PCR products were digested with BglII and XbaI, and inserted into BamHI/XbaI sites in the plasmid vectors.

This process produced 13 expression plasmids. These plasmids were confirmed by DNA sequencing. The recombinant proteins expressed by pET-23a(+) and pUEX2-M3/H is are His-tag proteins with a six histidine residues at the C-terminus or N-terminus, respectively. The recombinant proteins expressed by pMAL-c2X have a maltose binding protein (MBP) tag at the N terminus.

Example 4

Expression and Purification of Proteins

Competent cells of *E. coli* strain BL21(DE3)/pLysS were purchased from Novagen (San Diego, Calif., USA). Competent *E. coli* strains DH5α and TOP 10 were purchased from Invitrogen. Synthetic *Lawsonia* genes were cloned into Invitrogen's GATEWAY entry plasmid, pDONR221, and grown in Invitrogen's *E. coli* strain OmniMAX 2 T1 Phage-Resistant (T1). Expression Plasmids pMAL-c2X and pET-23a(+) were purchased from New England Biolabs and Novagen, respectively. Expression plasmid pUEX2-M3 was obtained from Biostar Inc. (Saskatoon, Saskatchewan, Canada).

Luria Bertani (LB) broth was prepared according to standard procedures. LB plates were prepared from imMedia Amp (or Kan) Agar (Invitrogen, Carlsbad, Calif., USA). Carbenicillin Disodium Salt, Kanamycin Sulfate, and Isopropyl-β-D-thioglactopyranoside (IPTG) were purchased from Thermo Fisher Scientific Inc. (Pittsburgh, Pa., USA). All restriction endonucleases, and DNA ligase were purchase from New England Biolabs (Ipswich, Mass., USA).

The expression plasmids derived from pMAL-c2X were transformed into *E. coli* TOP 10 strain. Cells were grown overnight in LB medium at 37° C. Flasks containing LB medium which contained 100 g/mL carbenicillin were inoculated with a ¹/₄₀ volume of the overnight culture and incubated at 37° C. until the absorbance at 600 nm reached 0.6 to 0.8. IPTG was added to a final concentration of 0.25 mM, and incubation was continued for 2-4 hr at 30 C. Two to three liters of cells for each protein were harvested by centrifugation at 7000×g for 10 min and resuspended in 250-300 mL buffered saline solution. The cells were disrupted by APV Homogenizer. The samples were centrifuged at 12,000×g for 10 min to separate soluble and insoluble fractions. Then, Amylose Resin (NEB, Ipswich, Mass.) equilibrated with a buffered saline solution, were added to the soluble fraction. After the solution were mixed for 1-20 hours at 4° C., the resin was loaded in a column and washed with 20 column volumes of buffered saline. The recombinant protein was eluted from the column by use of buffered saline with 10 mM maltose.

The expression plasmids derived from pET-23a(+) were transformed into *E. coli* BL21(DE3)pLysS strain. Cells were grown overnight in LB medium at 37° C. Flasks containing LB medium which contained 100 g/mL carbenicillin were inoculated with a ¹/₄₀ volume of the overnight culture and incubated at 37° C. until the absorbance at 600 nm reached 0.6 to 0.8. IPTG was added to a final concentration of 0.25 mM, and incubation was continued for 2-4 hr at 30° C. The pUEX2-M3/His-G07501 plasmid, transformed into DH5α *E. coli* strain was grown in a similar manner, and then induced at 42° C. for 2-3 hours. Two to three liters of cells for each protein were harvested by centrifugation at 7000×g for 10 min and resuspended in 250-300 mL Lysis buffer (50 mM phosphate buffer, pH 8.0, 300 mM NaCl, 10 mM imidazole). The cells were disrupted by APV Homogenizer. The samples were centrifuged at 12,000×g for 10 min to separate soluble and insoluble fractions. Then, Ni-NTA Superflow agarose beads (QIAGEN) equilibrated with Lysis buffer were added to the soluble fraction. After the solution were mixed for 1-20 h at 4° C., the resin was loaded in a column and washed with 20 column volumes of Wash buffer (50 mM phosphate buffer, pH 8.0, 300 mM NaCl, 20 mM imidazole). The recombinant protein was eluted from the column by use of Elution buffer (50 mM phosphate buffer, pH 8.0, 300 mM NaCl, 250 mM imidazole).

The 13 *Lawsonia* genes of the present invention were successfully expressed in *E. coli* strain TOP10, BL21(DE3) pLysS or DH5α. Nine of the recombinant proteins were expressed as soluble protein (Table 1). Two of the expressed recombinant proteins, Law 0033-OstA (SEQ ID NO:1) and Law C046-SLH (SEQ ID NO:4) are partially soluble, and two, Law 005-AsmA (SEQ ID NO:6) and Law 0043-PtfH (SEQ ID NO:8), are insoluble. The protein size and type of purification tag are listed in Table 1. Western analysis showed that 5 of the 13 proteins reacted with the swine anti-*Lawsonia* sera. Based on the western blot analysis, the 5 proteins that interacted with swine anti-*Lawsonia* sera were Law 0691-PAL (SEQ ID NO:2), Law 0995-OPRM (SEQ ID NO:3), Law 0147-SlyB (SEQ ID NO:5), Law 1082-FeoA (SEQ ID NO:10), and Law 0460-PEBP (SEQ ID NO:11).

TABLE 1

Recombinant *Lawsonia Intracellularis* Proteins

| Recombinant Protein | Tag | Size (kDa) | Soluble(s) or Insoluble (I) |
|---|---|---|---|
| Law 0033-OstA (SEQ ID NO: 1) | MBP | 130 | partially S |
| Law 0691-PAL (SEQ ID NO: 2) | MBP | 57 | S |
| Law0995-OPRM (SEQ ID NO: 3) | MBP | 80 | S |
| Law C046-SLH (SEQ ID NO: 4) | MBP | 130 | partially S |
| Law 00147-SlyB (SEQ ID NO: 5) | MBP | 55 | S |
| Law 0050-AsmA (SEQ ID NO: 6) | MBP | 160 | I |
| Law 0065-LoIA (SEQ ID NO: 7) | MBP | 67 | S |
| Law 0043-PtfH (SEQ ID NO: 8) | MBP | 128 | I |
| Law 0649-OmpB (SEQ ID NO: 9) | MBP | 131 | S |
| Law 1082-FeoA (SEQ ID NO: 10) | MBP | 55 | S |
| Law 0460-PEBP (SEQ ID NO: 11) | His | 20 | S |
| Law B004-Fluf (SEQ ID NO: 12) | MBP | 100 | S |
| Law 1153-OmpA (SEQ ID NO: 13) | His | 44 | S |

Example 5

Methods of Detection of Expressed Proteins

The recombinant proteins that were boiled for 10 minutes with NuPAGE LDS Sample Buffer (Invitrogen) in the presence of β-mercaptoethanol were subjected to SDS-polyacrylamide gel electrophoresis (PAGE) using 4% to 12% NuPAGE Bis-Tris gel (Invitrogen) at 200 Volts for 35 minutes. The gels were stained with SimplyBlue™ Safe Stain (Invitrogen) or transferred to 0.2 pore size nitrocellulose membranes (Invitrogen) and reacted with swine anti-*Lawsonia* sera, rabbit anti-maltose binding protein sera plus a phosphatase labeled goat anti-rabbit sera, peroxidase labeled mouse anti-His sera, or phosphatase labeled mouse anti-His (C-term) sera.

Mouse monoclonal anti-His(C term) antibody was obtained from Invitrogen. Peroxidase labeled mouse monoclonal anti-His antibody was obtained from Roche Applied Science (Indianapolis, Ind., USA). Rabbit anti-maltose binding protein antibody was obtained from New England Biolabs. Phosphatase labeled goat anti-rabbit sera was obtained from Kirkegaard & Perry Laboratories, Inc. (Gaithersburg, Md., USA). Swine anti-*Lawsonia* sera was prepared in house by standard methods available to one of skill in the art.

Example 6

Vaccine Composition and Use

Protein immunogens of the present invention were expressed, concentrated and purified from expression hosts such as *E. coli* using various methods known in the art. Purified protein immunogens can be formulated into vaccines containing an immunologically effective amount of each immunogen and an appropriate pharmaceutical carrier. The formulated vaccines may be combined with an adjuvant. The formulated vaccines may be an aqueous solution, a suspension or an emulsion. An immunologically effective amount of each immunogen in the vaccines of the present invention is determinable by methods known in the art without undue experimentation. In a specific embodiment of the invention, the general quantity of each immunogen will be between 5 μg and 500 μg of purified protein. In a specified embodiment of the present invention, the amount will be between 10 μg and 250 μg. In an even more specified embodiment of invention the amount will be between 50 μg and 200 μg of each protein.

The present invention also encompasses combination vaccines comprising immunogens of the present invention and at least one antigenic component of other pathogens including, but not limited to, *Mycoplasma Hyopneumoniae*, *Erysipelas* spp, *salmonella*, *H. parasuis*, *clostridium* spp, *streptoccous suis*, *brachyspira* spp, *Bordetella*, *pasteurella*, *E. coli*, coronavirus, parvovirus, PRRS, Circovirus, and SIV.

Vaccines of the present invention may be administered to animals using a variety of methods including, but not limited to scarification, intramuscular, subcutaneous, intranasal, intraperitoneal, or oral methods.

Example 7

Results of Vaccination Studies

A study was conducted in pigs to test whether a killed vaccine based on virulent *Lawsonia* micro-organisms could provide protection against the disease caused by *Lawsonia*. In this study, *Lawsonia* organisms used for preparation of the bacteria were grown in a mouse fibroblast (McCoy's) cell line in T-175 cm$^2$ flasks using the method established in the art (e.g. Lawson et al, Gebhart et al.). Bacteria were harvested form infected McCoy cells as described in the art and live bacteria were inactivated by addition of Binary Ethyleneimine (BEI) and then formulated in the Emunade® adjuvant. The inactivated bacteria was tested at two dose levels; $1 \times 10^8$ and $5 \times 10^8$ bacteria per dose. The primary measure of efficacy was based on significant ($p<0.05$) reduction in prevalence and severity of macroscopic and microscopic lesions in the ileum of vaccinated versus control animals. The study schedule and activities are shown in Table 2. The results of this study are shown in Table 3. The data presented in Table 3 show that there was a significant reduction in ileum lesions scores between vaccinated animals and placebo control (t-test, $p<0.05$). Furthermore, there was a significant reduction in the colonization of vaccinated animals versus placebo control as determined by immunohistochemical staining of affected ileal tissues. These data demonstrate that vaccination of pigs with a bacterin based on killed or inactivated *Lawsonia intracellularis* results in significant protection against the disease caused by this bacteria.

TABLE 2

Treatment groups and vaccination/challenge activities

| Treatment Group | No. of Animals | Vaccine Identification | Dose/Route | Vaccination (Study Day) | Serum Collection Days | Days |
| --- | --- | --- | --- | --- | --- | --- |
| A | 15 | B06-237-01A | 2 ml/IM | 0, 21 | 0, 21, 42, 63 | 63 |
| B | 15 | B06-237-01B | 2 ml/IM | 0, 21 | 0, 21, 42, 63 | 63 |
| C | 15 | B06-237-01C | 2 ml/IM | 0, 21 | 0, 21, 42, 63 | 63 |

TABLE 3

Impact of vaccination with low passage *Lawsonia* on crypt epithelium colonization and Ileal lesions

| Treatment | Ileum lesion score | IHC score | % animals +ve IHC |
| --- | --- | --- | --- |
| Vax- $5 \times 10^8$ | 0.33 ± 0.15 | 1.1 ± 0.31 | 54 |
| Vax- $1 \times 10^8$ | 0.36 ± 0.14 | 1.56 ± 0.25 | 91 |
| Placebo | 1.0 ± 0.19 | 2.53 ± 0.18 | 100 |

SEQUENCES

SEQ ID NO: 1
Name: Law 0033-OstA
Length: 806
Type: Amino Acid Sequence
Organism: Lawsonia intracellularis
LYNLFLPFILTNLIYYIIIPSLFIAFFPLQALSIINISEFAQPDINQSQTKWNLEADTLTTLSNNTIIEAKGNII
LTKGQDVFKADFARYYQKTGWLFLKGHVTVKMDENEINADEAEFNLNTKTGWLNNGNIFISSSHVYFSGARITKH
YGDYYTFNNVKVTTCDGPHPAWSISAKEAIVEVDGYAQLYDSTFKIKNIDVMYSPIFTIPAKQTRQSGFLNPNYG
ISQRRGIYYTQPYFLNIDQSSDLTFYAGLMTKIGPLGTVRYRSHKFTNQKTWFAASGIHDKNNIVTPGKDPVYPS
SQLVRNNHQRYWVRGMADGFIGNSTWCYISNLDYVSDQDYLREFDQGITGFSHSRSEMFQMFGRDIQEDDQSRLN
ALLIRKDWQRIGVVGNIRYEQDPTLGHGNHPTSQSELTQRIPQIDMFLYQGKLFQPLSLEGAIHLQSAYMYRAKG
TKGWRTELYPKVTLPIDLKYGSVITTVGLRETYYQTGIKSHTSPVAPHVPDTKTPRQTGQHRSLFNLQLESSTQA
HRIWRLKDKKTINLHSQSIGKTFCTALKHTIQPRICYSFIPREGQEKNPFYTLSDRILPQNDLTYSIVNILTKKN
VTISVDNNNNNNDNSVTPTLITSYYDLLYWNLSTGYDFEEERRKQYVEKYPKRPIKDIYSELELYILSWLTYSGK
TFISPYNGNITRHDHNIIFKSDRFSWKTGLSFRDQYYNYREHLQYRDENNIIMSSRLRLLQNSFSIQLLPNVSVT
LEDFRNLRELGTFGKTNSQLVEVTYLAQCYRIIGRYRYDGYDRSYTVLIEIPGLFE SEQ ID NO: 2
Name: Law 0691-PAL
Length: 162
Type: Amino Acid Sequence
Organism: Lawsonia intracellularis
MEVFRRYGIVLVLLVVLSAGFGCCKKSVDVEQSLATECIAPAPAINAAAETITDGIIYFDFDKYDIKPEYRDMLQ
KKAELLKEYPCIRVRIEGNCDARGTQEYNLALGERRARAAYEYLVMLGVNPSQLEIISFGKERPAVEGTGPAVWA
KNRRDDFRIIAK SEQ ID NO: 3
Name: Law 0995-OPRM
Length: 459
Type: Amino Acid Sequence
Organism: Lawsonia intracellularis
MKRLLLCIITCVIVSSCSFAPDYNRPHLELPEVWVSSPETGVPASMQWWKRFNDSTLDILVAEALQHNRDLIAAV
ARVDYAQAQLGVARSDLFPHFSGNAQATPVWVDHKRVTDGQSPYSANFSASWEIDIWGKIRNAKDAAFSQLMATE
AEKEGVFLSIAAQTANAYFLLRSLDLQCSIAERTVKTREDALSIYTAQYQKGFINKLDLTRAKTEVETARTALYQ
KRIAQENAETALSVLLGRSPRLIMDTAIERGVSMKDLSCIPVIPQGIPSELLERRPDIRQAEYILKATSANIGVA
RAAWLPSISLTGLFGIVSPHLSDLLKNPLKTWSYGETGTVPILDFGQVYYNVEAAQAKEREALANYEKTVQNAFK
DIHDALIRQYESKNIVNSLERMVKELRIAVHLARTLYDNGYTSYLDVLDAERALFQSELDLASAWSDRLSSIVQV
CLALGGSWE SEQ ID NO: 4
Name: Law C046-SLH
Length: 796
Type: Amino Acid Sequence
Organism: Lawsonia intracellularis
MYKFIIFYIICIYETIAIYLLLGSFISYFNRVFLKKEVKILDTTKVKKYARIGTFIFLYVIISSQVSLSHNARIG
YEDKNSDRKSKLILHNKLQVNEFDELRSDIVVTMTPLNIYTSTQENKITTIEANLLRLEVIQRTQPVLLVDVESS
LRDIYLLLDEAEGCNREVERCLKIWETASEHTKVLHRQTRERLSNAVIECQPGLPTNNEGKVVSVPEEIVASIEN
KVLHTANQQRTARKMEVAISRHKNKNIFLGNKQKLLRYRIEVLKARVEGNPDPPIPILTPQVLELPLLPDPPPSP
PPLPQQTFQFPDFGDPLPEPLSPLGDDPPQNVLNQEPQPGPSSEIVSTLQPSPSVEDLSSSGVTLECQEELSSSD
EEILDDECLTSGDESSTSDGESQRSSPPTKRRKLTHTPPPSDRGSPPGSSSMLMPYYTYGQVSSLQGLQSTLMSL
EDQLATQLRLSIIRSINVLGVCCKDDNQLQPHTFQSKKQTKIKGGIGRSHSTDNEIRPTSVNNSLFFSQQWHVIA

| SEQUENCES |
| --- |

SMDSRISNLETTISSRQAGVFTTPIDGLCLSLLYSNNKKKTQNFYGVVLDSVDGSAKAQIETDNILATVTWNKEH
QGFSGHLAGCYGWGKITNIRTIHFFDNESVSKGISSIHMSGGFIQLGYNVLLGKNYFLIPYVEYMRLAVAWDPYE
EHTGLIPCKVSGHKVHVCEKSIGLRNQWKITDNSQLQFWGSHIFTNHNTGEIASKPLSLSDYRNKISIPGYKKQY
IHREAGISYESNVMDTLSMELYSKLRVTKSIKDVTSYTSFTIRYVY

SEQ ID NO: 5
Name: Law 00147-SlyB
Length: 152
Type: Amino Acid Sequence
Organism: Lawsonia intracellularis
MQRCGLYIICLVLSIGMISCANFSASSFGGKQIRSAHIVEFGKVVSVKPVELEGNTPILGTITGGAVGGVLGSLI
GGGSGRILSTVVGAGAGAVAGNIAERKITTQQGLEIEVKLDNGQIISIVQGADQSFSPGERVRVLRGSDGSARVS
SI SEQ ID NO: 6
Name: Law 0050-AsmA
Length: 1075
Type: Amino Acid Sequence
Organism: Lawsonia intracellularis
MRSFLISIVTLFLLGIIVFFGITFYFIKQHPQYITNKILSTISKQLKDTSISANSIGFHIVPFPKLYLTNVILQT
QKGDTIHIKECLITPKITNILSGNISIYSIEVIQPIASIILQNEQKKNSKTTGYAIPKQVSHLLQLITDSKLFIE
NGSITFQNNDYCFKIIGINGKIGVSKTLTSSLKLTADEIIWEIMNTVSNNSSTAQKSIEKVQLHIEDMPYKINTA
LLHDTSPLYDLFTNTKKTTFKVSGAIPTTNTANNITFDFTTKLEKDNSDKLTMHGQLHIEGTLPNGNTSIPILLS
VPFTTTSSEDMTHFPPLLIKNSKLLFDKTHIDLHGTIKNYDTLSNLFFDGTMDVKNFSFPYWFTFARQLPNGIQH
ALNQLSGEIKFTLSPQQVNAQKIIIHSLDTTFQGNGTVNNFLSPTITLSLATKQFNLNTLLPELKGKKSSQLSYP
KETFLTILSNLHNNNNNNNIKKTINYDITIQADHVTCWKFDGYQFICNIQPKPQGTQIHTNCKNFYDGSLSSSLL
LSNRHTIQLAIENIQLSDITNIITKEYELKGKASGTSRVNGHGDTLASFLSSLKGTIDLYVTDGLVKKTASEAIP
FSMLHLTCDSIGQPSKGNKSSTIPYKGKWSAEISSARWNGSITMDGLIQFSTTDWLSIKAENIPSKVVCSVSGVQ
AVAYGGISFDIDNSFLSFSNFQGEIHPKTALSGTIKTSSSTSNTRQWEGSLTVMTQNLRNLLSKLGYEPKNISPT
MLQYCKLQGDIFISPATIRLTNIQGILDNTLIKFSLNGLQTNPPSWTGDIQLSSLNLDKYLLSINQNKLKKSQEL
WPIELLNKVNIQSTLTLAELIYRKVPYTNVVVPISLNQGTLSITPITASLCDGKTEASFKACPLSTNGNSAQIDF
HYISKGVDMIKLSKKRQQEYLISGLGTFVINIQSIAKSSIDFLKNLQGKWRIFIQNGYFKRNTTTTQQNFSNIGA
TGNIINGIITNNNFAITGPGMVITGSGKIDLPEWNLDYLITIDMEGFPIAIPIKYTGSIDNPKRTINAAKLILST
IGSLGRDTIGLIQDIFSAPLKLLLP SEQ ID NO: 7
Name: Law 0065-LoIA
Length: 249
Type: Amino Acid Sequence
Organism: Lawsonia intracellularis
LKNIINTIIFPKQRNKKMSQKFSMLQLILFFLTFIFYSYITDSYAESIPIVKELQQSYQSIKNFSATFTQELTHQ
ESGSKETRIGKLFFKKPLLVRWETNTPHEELLLINTNAVWDYLPDENLVYKYSTDIVKDSTSIIQVITGQVRLDK
NFSIIENNNNNNELIPLKLYPKEPTTQMVEAFLWINKKSLLIHKVQSIDFYGNTNTITFINITPNTHIDNNIFQ
FTPPKDVTIENLQDSSTPERPLFN SEQ ID NO: 8
Name: Law 0043-PtfH
Length: 900
Type: Amino Acid Sequence
Organism: Lawsonia intracellularis
MTKVGGSNPFSTLASMVGFSKSSSSSSSSKVAELKSKFEALGTLTKASPRPANGTQDTNRLSDRLFRGHYTVPAN
TASRVGGHLQRVDDNKSSSAANVAKRAAAHSSFASSNPGLQGASGSSSGGTGGSITDQVKSRGITARNFSDSNN
NSIGSGSSSGSILDQVRSQGITARGSSISSGNASGTSNVNDGTSSRDYGANVRNTRERFEAGPGGAQGESPGVKD
AKEATKGVSVSNLRGIFEGRGGADNNQVGRSSGGVSGASGSSGGAQGTGGTSGLGGAQGTLGSGGLDGGGVSGAAG
GTSGASGAGGARGTADGITSPGAREAQETIKNAGVSVRDLAGRFSGAQGTSGASGAAGASGASGAGGAAGAGGG
GLDRGGVSGSAGGTSGTSGAGGARGTADGITSPGAREAQETIKNAGVSVRDLAGRFSGAQTSGASGASGAAGVA
GMPAGSGDVVDGLRRGGEDTVDGFGRNQGSGPIPSSADFVDGPIGGIQGAGGASGAAGAAGASGAAGASGAAEPL
PTNGTDQQIAEVVVRNAENGHFDGIDFSTQPGGVESNTGSIPGTDLIVQRDITPGEQGVYNNLSEMGSWMDSPNA
SPTNAPESLTDDHSVLTTLLNNKEGLQDTVPFPLAVGEGTVVTKTLDPDIDTSKIKIPLEIVFGSGSMYGSGIGG
GSSTISSSMSDDGSSIGSTTRKNRAGEIISRIAMNQSPGAGSGGQTVVGGLGSGSSNINISGGRGGIVYGPMPN
VNVVAGDGLNRLQLGSGINPLALLQERMVNFSAAQLEHLHGQLTGMMAMMEAMPGVAFEGASVQMTLPEPGDTQT
MPSIRLSGFGEPRLRENIGQPGQPPTQEAFDALRNGPLNGVSELMSQVQEMITVRSEGSISLSRSSSLSDLSSEI SEQ ID NO: 9
Name: Law 0649-OmpB
Length: 851
Type: Amino Acid Sequence
Organism: Lawsonia intracellularis
MAYLSISKNQCKSFLITLVTIFIMTSIPQLAEAVEHFANGVPTVVQDVNVPADSYFGGADSAVGPNPIASTHLTI
STTQGFGQNALEFVVGGSLANGNGNPANINGDIVLIVENTNTQNSIIGGSMANAAPVTIGGSIFMTLRNVTAVDP
IFGGSVDVRFFAQQQPNEDQLVGGDININLENVTTPEFYGLGYANGVIPVNVLNRNFLVAVQGNITTNISNSNIA
TVMLGSHYDTTMAVGGNGTINVDNSTIGYLSASNSSDFVNPDLTNTVTFNIGPNNRIANIFASNNGVIPHFIVNM
DGSGTEIQELTLGNVIRGGLVLTSELNLSQGTINNLITGNEYYDRSGLRTTVNVRGGTIGVLTSGGSDYSELNFI
PGEISTILATNSIGNQDFASLSQVTIHQGAETLWGMRDEVFELQTNNLQLGGELFIPADGTGGVALITNHIIANS
GVITPVNMSPERMTPIIGFLEPTGEVAQLTIYGPLTVNLSHSPEILGKIITQPIPIAVTNSDVFGTSKLFVEHNT
KGLIWSDIIFNPQDKTWYLTNFRGSEDFYGLSAAREASNWLRQQHIWSLQRRSNKLLDHGVDGLWMNVQGGYEKL
DAAIGDAKMPWIMASLGYDFMHKLSDFYNLKALYGFGFATGKNKWNTINSTTNDIYMGLVGAYVGLMHEATGL

```
YGTVSGQFATNRTKTKCTGFDETYNWKENVPTEAIEIGWKWSIDEFKINPRGQVIFEQLSKHHFSLSQEGDTAIL
DKEFLTTTVIGISGEYDLDLRSKIIKLQASVDWIKGISGDFAAKSEVLNMKFKDKNDTSTFRGTLGASAQLLENF
EVHLDIFGDLGNDKGIGGQVGATYRF*

SEQ ID NO: 10
Name: Law 1082-FeoA
Length: 112
Type: Amino Acid Sequence
Organism: Lawsonia intracellularis
MSAVVDSMTPFPCSEHDELPVINEATACCVFDKVESYISLRDLKVGQHARVVRVQADGELGRRIRDMGLVPGTEV
TIVGRAPLKDPVALRLLGFTLSLRNSEADYVMVSPIS SEQ ID NO: 11
Name: Law 0460-PEBP
Length: 183
Type: Amino Acid Sequence
Organism: Lawsonia intracellularis
MKKLILTFALLLVTNITTFASEPPFTLSSPQMKNGTIATNQVYNSFGCKGKNISPSLEWKNPPEGTKSFAITMFDI
DAPTGSGWWHWIVYNIPTSTSSLVLGAGNDPKKLPKGAVQSINDFGFIGFGGPCPPVGAKLHHYIFTIYALNVET
MDLPATTMPAAIGFNIHMHMIDKATFTATYSRK SEQ ID NO: 12
Name: Law B004-Fluf
Length: 971
Type: Amino Acid Sequence
Organism: Lawsonia intracellularis
MYNIINKHQIIKILLFSLCVFFFTLTEKQKIYAADVFFEGRTETLINVNKPFDSFFGGSDSTIGTLETGPTNLTF
TTVGAFRNSVFRIIGGGRSSFNNPNTVKGNVTLTVYNTDVERIIGAGISNRGLVTVTGSVNMKLENVSVTRGIYG
GVYTQNGHVLGSINMHLKNVQTPLLIGSGVSNGPNRITVNGDINIDVEDSRIQYVNITGEVDAGIKGNATLTVKK
STVELINSGRGNILGNLKISIADSNIRGLSPVDFGSSVYGDTSINVINSQINDITLIPRAGGMLVGPVTLDITSS
TIQNIQCGPVSQNNQLNTLNVTVNTSNITNLNLGSVEGHTISTTATVTDSNITNLNVGTFNGLGVTENASVIINS
GNITNLNVGTNVIAAATTINSSATIHDGLIANLTLGSQGNGRTMIATANVNGGTIGLLTMGSENFIPGTRPITEL
AILNMSGGLIERIIVGNANSSTINFTPGKRSIVKTINGPELPYLVNIQKGAMTQWGTKNMPFLLDTRNLILSGTL
ITSNIQLADLSITNLFVANGGTLVPRKLIPGNQPVIQFLGGPQSLLVIHQPLKVNLSLSPKLIGSSMVPLAFVSQ
SFSSPDLFVKQTRSGLIWSDLEFDPTTSIWYVNNIQASQDFYSFSIARETTNWLRQQHIWTLQNRSSKLLDNEHY
GLWINVQGGHESLDTSIGSKAKMPWIMATAGYDYLQQLPRLDMKALYGLAFGASKGKSKWSSVNSTKNDAELGMV
SGYVGLIHNKTGLYSTLTLQLASSKLHTNSTGFYRNFKWTETTPTEALELGWKYTFNNGIKMNPRGQLIFEQTSK
HHFDLGIQNDKAILDKSQLITSSLGITVEYKLPVTTPINLYAGIERIKGQSGNFAISSQSLQMKFKHDNDTSVVR
ATIGTNILLGEHFNIHCDIFGDKGNDKGIGGQAGFTYKF SEQ ID NO: 13
Name: Law 1153-OmpA
Length: 398
Type: Amino Acid Sequence
Organism: Lawsonia intracellularis
EIVMANVSGIPAPRLLSTTNQMTNAAAGNTNRATGSMNGRNLTQIKTPQSMIDNASEELTTSLESKSSDDFAIKD
RKRQGKGSDSLLKMVQEYTELTNDDTRNAKRAMLSQVLRASQSSQDVLEKTLEQFSNKTDAWASLAEIAQEYGAE
SPQPTGLKSVLDAMETLENEFGDEIKAGLKGALNSKEFTDIGSAAQLRDLYTTTVTITAAPDAVLARLLEEYESD
DDLDRAIDFLLSTLGGELESADPSMDKVHLQSVMGDIEKTQQLHSSHKQCTTALSRWKEKHKGGGENSTLTPLEM
MRELIALKNENFISPSSIDKIVDQADPQDIEKEVLFLQEMLAAVRKFPIMVFDNVENRVRVMGAVQDAVDDAVRR
EDEFLFQKEHPDVPLQPDENNIQ SEQ ID NO: 14
Name: Law 0033-OstA
Length: 2322
Type: Synthetic Nucleic Acid Sequence
Organism: Synthetic
ATTATCAACATCTCTGAATTTGCACAACCGGACATCAACCAGTCTCAGACCCAAATGGAACCTGGAAGCCGACACT
CTGACCACTCTGAGCAATAACACTATTATTGAAGCGAAGGGTAACATCATCCTGACCAAAGGCCAGGATGTGTTT
AAAGCTGACTTTGCACGCTACTATCAGAAGACGGGCTGGCTGTTTCTGAAAGGTCACGTTACCGTGAAAATGGAC
GAAAACGAGATCAATGCAGACGAAGCGGAATTCAACCTGAACACCAAAACCGGCTGGCTGTGAACAACGGCAATATC
TTCATTAGCTCTAGCCATGTGTACTTCAGCGGCGCGCGCATCACTAAACACTACGGCGATTACTACACTTTTAAC
AATGTTAAGGTGACTACCTGCGATGGTCCTCATCCGGCCTGGTCCATCTCTGCGAAAGAAGCTATTGTTGAAGTT
GATGGTTACGCGCAGCTGTATGACAGCACCTTTAAAATCAAGAACATTGATGTTATGTACAGCCCGATCTTCACC
ATCCCGGCGAAACAAACTCGTCAGTCCGGTTTCCTGAATCCGAATTATGGTATCTCTCAACGCCGTGGCATCTAT
TACACGCAGCCGTACTTCCTGAACATCGATCAGTCCTCTGACCTGACTTTCTACGCAGGTCTGATGACCAAAATC
GGTCCTCTGGGCACGGTCGTTACCGCTCCCACAAATTTACGAACCAGAAGACCTGGTTCGCCGCTTCTGGTATC
CACGACAAAAACAACATCGTTACCCCGGGTAAAGACCCGGTTTATCCGTCTAGCCAACTGGTGCGCAATAATCAC
CAGCGCTACTGGGTTCGTGGTATGGCAGACGGTTTTATCGGTAACTCCACCTGGTGCTATATTTCTAATCTGGAT
TACGTGTCTGATCAGGACTATCTGCGTGAATTCGACCAGGGTATCACCGGTTTCTCTCACAGCCGCTCCGAGATG
TTCCAGATGTTTGGCCGTGACATCCAGGAAGACGATCAGTCCCGCCTGAACCGCCCTGCTGATCCGTAAAGACTGG
CAGCGTATCGGCGTAGTGGGTAACATCCGTTACGAACAGGATCCAACTCTGGGTCACGGCAACCACCCGACTTCC
CAAAGCGAGCTGACTCAGCGCATTCCGCAGATTGATATGTTCCTGTACCAGGGTAAGCTGTTTCAGCCGCTGAGC
CTGGAAGGCGCGATCCACCTGCAGAGCGCCTACATGTATCGTGCAAAAGGTACCAAAGGCTGGCGTACCGAACTG
TACCCGAAAGTTACCCTGCCGATCGACCTGAAATACGGCTCTGTAATTACGACGGTTGGTCTGCGCGAAACTTAT
TACCAGACCGGTATCAAATCCCACACCTCTCCGGTAGCTCCGCACGTTCCGGACACCAAGACTCCGCGCCAAACC
GGTCAGCACCGCTCTCTGTTCAACCTGCAGCTGGAATCCAGCACCCAGGCACACCGCATTTGGCGTCTGAAAGAT
```

|     SEQUENCES     |
| --- |
| AAGAAAACCATCAACCTGCACAGCCAGTCTATTGGCAAAACTTTTTGTACTGCTCTGAAACACACGATCCAGCCA<br>CGTATCTGCTACTCTTTCATCCCGCGCGAGGGCCAGGAGAAAAACCCGTTCTATACTCTGAGCGATCGCATCCTG<br>CCGCAGAACGATCTGACCTATTCCATCGTAAACATCCTGACTAAGAAAAATGTCACCATTTCCGTCGACAACAAT<br>AACAACAATAACGATAATAGCGTTACTCCGACTCTGATTACCTCTTACTACGACCTGCTGTACTGGAACCTGAGC<br>ACTGGCTATGACTTCGAAGAAGAACGTCGTAAGCAGTACGTAGAAAAATACCCGAAACGCCCTATTAAAGATATC<br>TACTCCGAACTGGAACTGTACATTCTGTCCTGGCTGACCTACTCTGGCAAAACCTTCATCTCTCCGTACAACGGC<br>AACATCACCCGTCACGATCACAACATCATCTTCAAGAGCGATCGCTTTTCCTGGAAAACCGGCCTGTCTTTCCGT<br>GACCAGTATTACAACTACCGTGAACACCTGCAGTACCGTGATGAAAACAATATCATCATGAGCTCCCGTCTGCGT<br>CTGCTGCAAAACTCTTTCTCTATTCAGCTGCTGCCTAATGTGAGCGTAACCCTGGAGGATTTTCGCAACCTGCGT<br>GAACTGGGCACCTTCGGTAAGACCAACTCTCAACTGGTGGAAGTTACGTATCTGGCTCAATGCTACCGCATTATT<br>GGTCGTTATCGCTACGATGGTTACGACCGTAGCTACACTGTCCTGATTGAAATCCCTGGTCTGTTTGAATAA |

SEQ ID NO: 15
Name: Law 0691-PAL
Length: 414
Type: Synthetic Nucleic Acid Sequence
Organism: Synthetic
AAAAGCGTAGATGTAGAACAAAGCCTGGCAACCGAATGTATCGCACCGGCGCCGGCAATCAACGCGGCGGCAGAA
ACGATCACGGACGGTATCATTTACTTCGACTTCGATAAATACGACATCAAGCCGGAATACCGTGACATGCTGCAG
AAGAAAGCTGAACTGCTGAAGGAATACCCGTGCATCCGTGTTCGCATCGAAGGCAACTGTGATGCGCGCGGTACT
CAGGAATACAATCTGGCGCTGGGTGAACGTCGTGCGCGTGCGGCCTATGAATACCTGGTTATGCTGGGTGTGAAC
CCGAGCCAGCTGGAAATCATCAGCTTCGGCAAAGAGCGCCCAGCTGTTGAGGGTACCGGTCCGGCTGTGTGGGCG
AAAAACCGTCGTGACGATTTCCGCATCATCGCAAAATAA SEQ ID NO: 16
Name: Law 0995-OPRM
Length: 1326
Type: Synthetic Nucleic Acid Sequence
Organism: Synthetic
TTCGCTCCAGATTACAACCGTCCACACCTGGAACTGCCGGAAGTCTGGGTTTCTAGCCCGGAAACTGGCGTGCCG
GCATCCATGCAGTGGTGGAAACGTTTTAATGACTCTACGCTGGACATCCTGGTGGCCGAAGCCCTGCAGCACAAC
CGTGATCTGATCGCGGCGGTTGCGCGTGTAGATTACGCACAGGCTCAGCTGGGTGTTGCGCGCTCTGACCTGTTT
CCGCATTTTAGCGGTAACGCGCAGGCGACTCCTGTTTGGGTTGACCATAAACGTGTAACTGATGGTCAGAGCCCT
TACAGCGCGAACTTCAGCGCTAGCTGGGAGATTGATATCTGGGTAAAATTCGTAACGCTAAAGATGCTGCGTTC
AGCCAACTGATGGCAACCGAAGCAGAAAAAGAGGGTGTGTTCCTGTCTATCGCAGCACAGACTGCTAACGCATAT
TTCCTGCTGCGCTCTCTGGACCTGCAATGCTCTATCGCTGAACGCACGGTAAAAACTCGTGAAGACGCACTGTCT
ATCTATACCGCGCAGTATCAAAAGGGTTTTATCAACAAACTGGATCTGACGCGCGCGAAAACCGAAGTTGAGACT
GCTCGTACCGCGCTGTACCAGAAACGTATCGCACAGGAGAACGCTGAAACCGCGCTGTCTGTCCTGCTGGGCCGC
AGCCCGCGTCTGATTATGGATACTGCTATTGAACGCGGCGTATCCATGAAAGATCTGAGCTGTATCCCGGTTATC
CCGCAGGGCATTCCGTCCGAACTGCTGGAACGTCGTCCTGATATCCGCCAGGCAGGTATACCCTGAAAGCAACC
TCCGCGAACATCGGTGTGGCGCGCGCGGCGTGGCTGCCGTCTATTTCTCTGACCGGCCTGTTTGGTATCGTTTCC
CCGCACCTGTCCGATCTGCTGAAAAATCCTCTGAAAACCTGGAGCTATGGTGAAACCGGCACTGTACCAATCCTG
GACTTCGGTCAGGTTTACTATAACGTTGAAGCGGCCCAGGCGAAGGAACGTGAGGCTCTGGCCAACTACGAGAAA
ACCGTTCAGAACGCCTTCAAAGACATTCACGACGCGCTGATCCGTCAGTATGAATCCAAAAACATCGTCAACAGC
CTGGAACGTATGGTGAAGGAACTGCGTATCGCCGTCCATCTGGCTCTGCTCTGTACGACAACGGCTACACCTCT
TACCTGGACGTTCTGGATGCCGAACGCGCGCGCTGTTCCAGAGCGAGCTGGATCTGGCGAGCGCGTGGAGCGATCGT
CTGTCTAGCATCGTTCAGGTTTGCCTGGCGCTGGGTGGCTCCTGGGAATAA SEQ ID NO: 17
Name: Law C046-SLH
Length: 2286
Type: Synthetic Nucleic Acid Sequence
Organism: Synthetic
AAAAAGGAAGTTAAAATCCTGGACACCACTAAAGTAAAAAAGTATGCGCGTATCGGCACGTTTATCTTTCTGTAC
GTAATCATCAGCTCCCAGGTGTCTCTGTCTCACAACGCCCGTATCGGCTATGAAGACAAAAACAGCGACCGCAAG
AGCAAGCTGATCCTGCATAACAAACTGCAGGTCAACGAATTCGACGAACTGCGCAGCGACATCGTTGTGACTATG
ACGCCTCTGAACATCTACACCTCCACCCAGGAAAACAAAATCACCACCATCGAAGCGAATCTGCTGCGTCTGGAA
GTCATTCAACGTACTCAGCCGGTGCTGCTGGTTGATGTTGAATCTTCTCTGCGTGATATCTATCTGCTGCTGGAC
GAAGCGGAAGGTTGCAATCGCGAAGTGGAGCGCTGTCTGAAAATCTGGGAAACCGCGTCCGAACACACTAAGGTA
CTGCACCGTCAGACTCGTGAGCGTCTGAGCAATGCCGTTATCGAATGTCAGCCGGGTCTGCCTACCAACAATGAA
GGTAAAGTAGTCTCTGTTCCGGAGGAAATCGTCGCGTCTATCGAGAACAAAGTTCTGCACACGGCGAACCAGCAG
CGTACGGCACGTAAAATGGAAGTGGCCATTTCCCGTCACAAAAACAAGAATATCTTTCTGGGGTAACAAACAAAG
CTGCTGCGCTATCGCATTGAAGTTCTGAAAGCTCGTGTGGAAGGCAACCCGGATCCGCCGATTCCGATTCTGACC
CCGCAGGTTCTGGAACTGCCGCTGCTGCCGGATCCACCGCCATCTCCGCCGCCTCTGCCGCAGCAAACCTTCCAG
TTCCCGGACTTCGGCGACCCACTGCCGGAACCACTGAGCCCGCTGGGCGATGATCCACCGCAGAACGTACTGAAC
CAGGAACCGCAGCCAGGTCCGTCTTCCGAAATCGTCTCCACTCTGCAGCCATCTCCGTCTGTTGAGGATCTGAGC
TCCTCCGGCGTCACTCTGGAGTGCCAGGAGGAACTGTCTTCCAGCGATGAAGAGATCCTGGATGAGTGCCTG
ACCTCCGGCGACGAATCTTCTACTTCCGATGGTGAAAGCCAACGTTCCAGCCCGCCGACCAAACGCCGCAAGCTG
ACCCACACTCCTCCACCATCTGACCGTGGTTCCCCGCCAGGCTCTTCTTCTATGCTGATGCCGTACTATACCTAC
GGTCAGGTGTCTTCTCTGCAGGGTCTGCAGTCTACTCTGATGTCTCTGGAAGACCAGCTGGCTACTCAGCTGCGC
CTGAGCATTATCCGTTCTACTTCTATTAACGTCCTGGGTGTTTGCTGCAAAGACGAACAGCTGCAGCCGCACCTTC
CAATCCAAGAAACAAACCAAAATCAAGGGTGTATCGGTCGTTCCCACTCTACCGACAACGAAATTCGTCCGACG
TCCGTTAACAATAGCCTGTTCTTTAGCCAGCAGTGGCATGTGATCGCTTCTATGGACAGCCGTATCTCTAACCTG
GAAACTACTATCTCCTCCCGCAAGCAGGTGTTTTCACCACTCCGATTGATGGCCTGTGCCTGTCTCTGCTGTAC
TCCAACAACAAGAAAAAAACGCAGAATTTCTACGGCGTTGTTCTGGACTCCGTCGATGGCAGCGCAAAAGCCCAG
ATTGAAACCGACAATATCCTGGCGACGGTAACTTGGAACAAAGAACACCAGGGTTTCAGCGGCCACCTGGCCGGC
TGCTACGGCTGGGGTAAAATCACCAACATCCGCACCATCCACTTCTTTGATAACGAGAGCGTTTCTAAAGGTATC

```
                                  SEQUENCES
AGCAGCATCCATATGTCCGGCGGCTTCATCCAGCTGGGTTACAACGTCCTGCTGGGCAAAAACTACTTTCTGATC
CCGTATGTGGAATACATGCGTCTGGCAGTGGCATGGGATCCGTACGAAGAACACACTGGTCTGATTCCGTGTAAA
GTTTCTGGCCACAAAGTTCACGTTTGCGAGAAAAGCATCGGCCTGCGCAACAATGGAAAATCACTGACAATTCC
CAGCTGCAGTTCTGGGGTAGCCATATTTTCACCAACCATAACACCGGCGAAATCGCCTCCAAACCGCTGTCCCTG
AGCGATTACCGCAACAAAATCTCTATCCCGGGCTACAAAAAGCAGTACATCCACCGCGAGGCGGGCATTTCCTAT
GAGTCTAACGTTATGGATACTCTGTCCATGGAACTGTATTCTAAGCTGCGTGTGACTAAATCCATTAAAGATGTG
ACGAGCTACACCTCTTTTACCATCCGTTATGTGTAC

SEQ ID NO: 18
Name: Law 00147-SlyB
Length: 396
Type: Synthetic Nucleic Acid Sequence
Organism: Synthetic
TTAATTAAtaGAATTCacGGTAAACAGATCCGTAGCGCACACATCGTTGAATTTGGTAAAGTTGTTTCTGTTAAA
CCGGTTGAACTGGAAGGTAACACCCCGATCCTGGGTACCATCACCGGTGGTGCGGTTGGTGGCGTGCTGGGTTCT
CTGATTGGCGGTGGTTCCGGTCGTATTCTGTCTACTGTTGTTGGTGCAGGTGCTGGCGCCGTCGCGGGCAACATC
GCTGAACGTAAAATCACCACTCAGCAGGGTCTGGAGATCGAAGTTAAACTGGACAATGGCCAGATCATCAGCATC
GTTCAAGGTGCGGATCAGAGCTTCTCCCCGGGTGAACGTGTTCGCGTTCTGCGTGGTTCCGACGGCAGCGCACGC
GTCAGCTCTATCTGAGGATCC SEQ ID NO: 19
Name: Law 0050-AsmA
Length: 3189
Type: Synthetic Nucleic Acid Sequence
Organism: Synthetic
TTAATTAAtaGAATTCaCATCACGTTCTACTTCATCAAACAGCACCCGCAGTATATCACCAACAAAATTCTGTCC
ACCATCTCTAAACAGCTGAAGGACACCTCTATCTCTGCGAACAGCATCGGCTTCCACATCGTACCGTTCCCTAAA
CTGTATCTGACCAACGTAATCCTGCAGACCCAGAAAGGCGATACCATCCACATCAAAGAATGCCTGATCACTCCG
AAAATCACGAACATTCTGTCCGGTAACATCAGCATCTACTCCATCGAGGTTATTCAGCCAATTGCATCCATTATC
CTGCAGAACGAGCAGAAAAAGAACTCTAAAACGACTGGTTATGCCATTCAAAACAGGTGAGCCACCTGCTGCAG
CTGATCACCGATAGCAAACTGTTTATCGAGAACGGCAGCATCACCTTTCAGAACAACGACTACTGCTTTAAAATC
ATTGGTATCAACGGCAAAATTGGTGTTAGCAAAACTCTGACGTCTTCTCTGAAACTGACTGCAGACGAAATCATT
TGGGAGATCATGAACACCGTATCCAACAACTCCAGCACCGCGCAGAAATCTATTGAAAAAGTGCAACTGCACATC
GAAGACATGCCATACAAAATCAACACCGCCCTGCTGCACGACACGAGCCCGCTGTACGATCTGTTTACTAATACC
AAGAAGACCACCTTCAAGGTGTCCGGCGCTATCCCGACCACCAACACCGCAAACAACATTACCTTTGACTTTACC
ACCAAACTGGAAAAAGATAACTCCGACAAGCTGACCATGCACGGTCAGCTGCACATTGAGGGTACTCTGCCGAAC
GGCAACACCTCCATCCCGATCCTGCTGTCCGTTCCGTTTACCACTACTAGCTCCGAAGACATGACGCATTTCCCT
CCGCTGCTGATCAAAACAGCAAGCTGCTGTTTGATAAAACCCACATCGATCTGCACGGCACCATTAAAAACTAT
GATACCCTGTCCAACCTGTTTTTCGACGGTACCATGGATGTGAAAAACTTCTCTTTTCCGTATTGGTTTACCTTC
GCCCGTCAGCTGCCGAATGGCATTCAGCATGCGCTGAACCAGCTGTCCGGCGAAATTAAATTCACTCTGTCCCG
CAGCAAGTAAACGCACAGAAAATCATCATTCACAGCCTGGACACTACTTTTCAGGGTAACGGCACCGTTAACAAC
TTCCTGTCCCCTACTATTACTCTGAGCCTGGCTACCAAACAGTTCAACCTGAACACCCTGCTGCCAGAACTGAAA
GGTAAAAAGTCCAGCCAGCTGTCTTACCCTAAGGAAACTTTCCTGACCATCCTGAGCAACCTGCACAACAACAAT
AACAACAACAACATTAAGAAAACGATCAACTACGATATCACCATCCAGGCGGACCATGTGACTTGTTGGAAGTTT
GACGGCTATCAGTTCATTTGTAACATTCAGCCGAAACCGCAGGGCACGCAGATCCATACCAACTGTAAAAACTTC
TACGATGGCTCCCTGTCTTCCTCCCTGCTGCTGAGCAATCGTCACACCATCCAGCTGGCCATTGAGAACATTCAG
CTGTCTGATATCACTAACATTATCACTAAAGAGTACGAGCTGAAAGGCAAAGCCTCCGGCACTTCCCGTGTCAAC
GGTCACGGTGATACTCTGGCTAGCTTTCTGAGCTCTCTGAAAGGCACCATCGACCTGTACGTAACCGACGGCCTG
GTCAAGAAAACCGCTGTCTGAAGCCATCCCGTTCTCTATGCTGCACCTGACTTGTGATTCTATCGGCCAGCCGAGC
AAGGGTAACAAGAGCTCCACCATTCCATACAAAGGTAAATGGTCTGCGGAAATTTCTTCTGCTCGCTGGAACGGT
TCCATCACTATGGACGGCCTGATTCAGTTCTCCACCACCGATTGGCTGAGCATCAAAGCAGAAACATTCCGAGC
AAAGTGGTCTGCAGCGTTAGCGGTGTTCAGGCGGTCGCGTATGGCGGCATCTCTTTTGATATCGATAACAGCTTC
CTGAGCTTCAGCAACTTCCAAGGCGAAATTCACCCGAAAACCGCCCTGAGCGGTACCATCAAGACCAGCTCCTCC
ACCTCTAACACCCGTCAATGGGAAGGTTCCCTGACTGTCATGACCCAGAACCTGCGCAACCTGCTGTCCAAACTG
GGTTATGAACCGAAAAATATCAGCCCAACCATGCTGCAGTATTGCAAGCTGCAAGGTGACATTTTCATTTCCCCT
GCTACTATTCGCCTGACTAACATCCAGGGTATCCTGGACAACACCCTGATTAAGTTTTCCCTGAACGGTCTGCAG
ACTAACCCCACCGAGCTGGACCGGCGACATCCAGCTGTCCTCCCTGAACCTGGACAAATATCTGCTGTCTATTAAC
CAAAACAAACTGAAAAAGTCCCAGGAACTGTGGCCTATTGAACTGCAACAAAGTTAACATTCAGTCTACTCTG
ACCCTGGCGGAGCTGATCTATCGCAAAGTGCCGTACACCAACGTGGTAGTGCCTATCTCTCTGAATCAGGGCACC
CTGTCTATCACCCCGATCACCGCCAGCCTGTGCGACGGTAAAACCGAAGCGTCCTTCAAAGCTTGCCCACTGTCT
ACTAACGGCAACTCTGCCCAAATCGACTTCCACTATATTTCCAAGGGCGTCGATATCATCAAGCTGTCTAAGAAA
CGTCAGCAGGAGTACCTGATCTCTGGCTGGGACACCTTCGTAATCAACATCCAGAGCATCGCAAAATCCTCTATT
GACTTCCTGAAAAATCTGCAGGGTAAATGGCGCATTTTTATTCGAACGGTTACTTTAAACGCAACACTACGACC
ACTCAGCAGAACTTTTCTAACATCGGTGCGACCGGCAATATCATTAACGGCATTATCACCAATAACAACTTCGCG
ATCACTGGTCCGGGTATGGTTATCACCGGTAGCGGCAAGATCGACCTGCCAGAATGGAATCTGGATTACCTGATT
ACTATCGACATGGAAGGTTTTCCAATTGCGATCCCGATCAAATATCTGGTAGCATCGATAATCCAAAACGCACC
ATCAATGCGGCTAAACTGATTCTGTCTACCATCGGTTCTCTGGGTCGCGATACCATTGGTCTGATTCAGGACATT
TTCTCTGCTCCGCTGAAACTGCTGCTGCCGTGAGGATCC SEQ ID NO: 20
Name: Law 0065-LoIA
Length: 639
Type: Synthetic Nucleic Acid Sequence
Organism: Synthetic
TTAATTAAtaGAATTCacGAAAGCATCCCGATTGTAAAAGAACTGCAGCAAAGCTACCAGTCTATCAAAAACTTC
AGCGCGACCTTCACCCAAGAGCTGACTCACCAGGAGAGCGGTTCTAAAGAGACTCGTATCGGCAAACTGTTTTTC
AAGAAACCGCTGCTGGTTCGTTGGGAAACCAACACCCCACACGAAGAACTGCTGCTGATCAACACCAACGCCGTG
```

| SEQUENCES |
|---|
| TGGGACTACCTGCCAGATGAAAACCTGGTCTACAAATACTCTACTGATATCGTTAAAGACAGCACGAGCATTATT
CAAGTGATCACCGGTCAGGTTCGTCTGGACAAAAACTTTAGCATCATTGAAAACAATAACAACAACAATAACGAA
CTGATCTTTCTGAAACTGTACCCGAAAGAACCGACCACCCAGATGGTCGAGGCCTTCCTGTGGATCAACAAAAAG
AGCCTGCTGATCCACAAAGTTCAGAGCATCGATTTCTACGGTAACACTAACACCATCACCTTTATCAACATCACC
CCTAACACCCACATTGATAATAACATCTTCCAGTTTACCCCGCCGAAGGACGTTACTATTGAAAACCTGCAGGAT
AGCTCTACTCCGGAGCGCCCACTGTTCAATTAAGGATCC

SEQ ID NO: 21
Name: Law 0649-OmpB
Length: 2472
Type: Synthetic Nucleic Acid Sequence
Organism: Synthetic
TTAATTAAtaGAATTCacGTAGAACACTTCGCAAATGGCGTACCGACTGTAGTTCAAGATGTAAACGTGCCGGCC
GATTCTTATTTCGGTGGCGCTGATTCTGCTGTGGGCCCGAACCCGATTGCGTCTACGCACCTGACCATCTCTACT
ACTCAGGGCTTCGGTCAGAACGCCCTGGAGTTCGTAGTAGGTGGTTCTCTGGCAAACGGTAATGGCAACCCAGCA
AACATCAACGGTGATATTGTACTGATCGTTGAAAACACGAACACTCAGAACAGCATCATTGGTGGTTCCATGGCA
AATGCAGCGCCGGTTACCATTGGTGGTAGCATCTTCATGACGCTGCGTAACGTTACCGCTGTTGATCCGATCTTC
GGTGGCTCTGTTGATGTCCGCTTCTTCGCACAGCAGCAGCCGAACGAGGACCAGCTGGTGGGTGGCGATATCAAC
ATTAACCTGGAGAACGTCACTACTCCGGAGTTCTACGGTCTGGGTTATGCGAATGGCGTAATCCCGGTTAATGTT
CTGAATCGTAACTTTCTGGTGGCGGTTCAGGGTAACATCACCACCAATATCTCTAACAGCAACATCGCAACCGTT
ATGCTGGGCTCCCACTACGACACTACCATGGCAGTAGGTGGTAACGGCACTATCAACGTGGACAACAGCACCATT
GGTTACCTGAGCGCGTCTAATTCTTCTGACTTCGTTAATCCGGACCTGACTAACACGGTTACCTTCAACATCGGC
CCGAACAACCGTATTGCAAACATCTTTGCAAGCAACAACGGCGTGATTCCTCATTTCATTGTTAACATGGACGGT
TCCGGCACGGAAATCCAGGAGCTGACCCTGGGTAACGTAATTCGTGGTGGTCTGGTTCTGACGTCCGAACTGAAC
CTGTCCCAGGGTACCATCAACAACCTGATCACCGGCAACGAGTACTATGATCGTTCCGGTCTGCGTACTACCGTA
AACGTGCGTGGTGGTACCATCGGCGTGCTGACGTCCGGCGGTAGCGATTATTCCGAGCTGAACTTCATCCCAGGC
GAAATCAGCACCATTCTGGCTACTAATAGCATTGGTAACCAAGATTTCGCATCCCTGAGCCAGGTAACTATCCAC
CAAGGCGCCGAAACCCTGTGGGGTATGCGTGATGAAGTGTTCGAGCTGCAGACTAACAACCTGCAGCTGGGTGGC
GAACTGTTCATTCCGGCAGATGGTACCGGTGGTGTAGCCCTGATCACCAACCATATCATTGCAAACAGCGGTGTA
ATCACGCCGGTGAACATGTCCCCGGAGCGCATGACGCCGATCATCGGTTTCCTGGAGCCTACCGGCGAAGTTGCT
CAGCTGACCATCTACGGTCCTCTGACCGTAAACCTGTCCCACTCTCCTGAGATCCTGGGCAAGATCATCACGCAG
CCGATCCCGATCGCTGTGACTAATTCTGATGTGTTCGGCACTTCCAAACTGTTTGTGGAGCACAATACCAAGGGT
CTGATTTGGTCTGATATCATCTTTAATCCGCAGGACAAGACCTGGTACCTGACCAACTTCCGTGGCTCTGAAGAT
TTCTACGGCCTGTCTGCCGCTCGTGAAGCCTCTAACTGGCTGCGTCAACAACACATCTGGTCCCTGCAACGTCGT
TCTAACAAACTGCTGGATCACGGTGTGGACGGTCTGTGGATGAACGTGCAAGGTGGTTATGAAAAGCTGGATGCT
GCTATTGGTGATGCCAAGATGCCGTGGATTATGGCCTCCCTGGGCTATGACTTCATGCACAAACTGAGCGACTTC
TATAATCTGAAGGCGCTGTACGGTTTCGGCTTCGGTTTCGCTACCGGCAAGAACAAATGGAACACTATCAACTCT
ACCACTAATGACATTTACATGGGTCTGGTCGGTGCGTACGTTGGTCTGATGCATGAAGCCACGGGCCTGTATGGT
ACCGTGAGCGGTCAGTTCGCGACGAACCGCACCAAAACCAAATGCACTGGCTTCGACGAAACCTACAATTGGAAA
GAAAACGTTCCGACTGAAGCCATTGAAATCGGTTGGGAAATGGTCCATTGATGAGTTTAAAATTAACCCTCGCGGT
CAGGTAATCTTTGAACAGCTGAGCAAACATCATTTTTCCCTGTCTCAGGAAGGTGATACTGCGATCCTGGATAAG
GAGTTCCTGACGACCACTGTTATCGGTATTTCCGGCGAATATGACCTGGACCTGCGCTCCAAAATCATTAAACTG
CAGGCCAGCGTTGACTGGATTAAAGGCATCTCTGGTGATTTCGCAGCTAAAAGCGAAGTTCTGAACATGAAATTC
AAAGACAAAAACGATACTTCTACCTTCCGTGGCACTCTGGGTGCTAGCGCCCAGCTGCTGGAGAACTTTGAAGTT
CACCTGGATATCTTCGGTGATCTGGGTAACGACAAAGGTATTGGCGGCCAGGTGGGTGCTACCTACCGCTTC SEQ ID NO: 22
Name: Law 0043-PtfH
Length: 2628
Type: Synthetic Nucleic Acid Sequence
Organism: Synthetic
TCTAGCAGCTCTAAGGTTGCAGAACTGAAATCTAAATTCGAAGCGCTGGGTACGCTGACCAAGGCTTCCCCACGT
CCGGCGAACGGTACCCAGGACACCAATCGCCTGTCCGACCGCCTGTTCCGTGACCATTATACTGTCCCTGCAAAC
ACCGCAAGCCGTGTTGGCGGTCATCTGCAGCGCGTCGATGATAACAAATCCTCTTCTAGCGCTGCGAACGTAGCA
AAACGTGCTGCTGCTCACTCCTCTTTTGCGTCTAGCAACCCGGGTCTGCAAGGCGCGTCTGGCTCTTCTAGCGGT
GGTACCGGCGGTAGCATTACCGACCAGGTGAAAAGCCGTGGCATCACTGCTCGTAATTTCTCTGACTCCAACAAC
AACTCCATCGGCAGCGGCTCTAGCTCCGGCTCTATCCTGGACCAGGTCCGTAGCCAGGGTATTACCGCACGTGGC
TCCAGCATCTCTTCTGGCAACGCTTCCGGCACCTCCAACGTTAACGATGGCACCAGCTCCCGTGATTACGGTGCG
AACGTACGTAACACCCGTGAACGTTTTGAAGCAGGTCCGGGCGGTTGCTCAGGGTGAAAGCCCGGGTGTTAAAGAC
GCTAAAGAAGCCACCAAAGGTGTAAGCGTCTCCAACCTGCGTGGTATCTTTGAAGGTCGTGGTGGCGCGGATAAT
AACCAAGTTGGTCGTTCTTCTGGCGGCGTCTCCGGCGCATCCGGCGCTGCGCCAGGCACCGGTGGTACC
TCCGGTCTGGGCGGTGCTCAGGGCACCCTGGGTTCTGGTGGCCTGGACGGTGCGGTGTAAGCGGTGCCGCGGGC
GGTACTTCCGGCGCCAGCGGCGCTGGCGGTGCGCGTGGCACCGCTGATGGCATCACTTCTCCGGGTGCACGTGAA
GCGCAGGAAACCATCAAAAACGCCGGTGTATCCGTTCGTGATCTGGCAGGCCGTTTTTCTGGTGCGCAGGGTACT
AGCGGTGCTTCTGGTGCTGCCGGCGCCTCCGGTGCATCTGGTGCGGGTGGTGCGGCAGGTGCAGCTGGCGGTGGT
GGTCTGGACCGCGGTGGCGTTTCTGGCAGCGCTGGCGGTACCGGCGGTACCGGTGGTACCGGTGGTGCCGCGGGC
ACCGCCGACGGTATCACTTCCCCGGGTGCTCGTGAAGCACAGGAAACCATTAAAAACGCTGGTGTTTCCGTTCGT
GACCTGGCCGGTCGTTTCAGCGGCGCTCAAGGTACTTCTGGTGCATCTGGCGCGTCCGGTGCGGCAGGCGTGGCA
GGCATGCCGGCGGGCTCCGGCGACGTGGTAGACGGTCTGCGTCGCGGTGGCGAAGACACCGTTGACGGTTTCGGT
CGTAACCAAGGTTCCGGCCCTATCCCATCTTCCGCCGACTTTGTTGACGGCCCGATCGGTGGTATTCAGGGCGCG
GGTGGCGCTTCTGGTGCAGCGGGTGCTGCGGGTGCTTCCGGTGCTGCGCAAGCGGTGCAAGCGGGAACCGCTG
CCGACGAACGGTACCGACCAGCAAATCGCCGAGGTGGTTGTTCGTAACGCGGAGAACGGCCACTTCGATGGCATC
GACTTCTCCACGCAGCCGGGTGGCGTTGAATCTAACACTGGTTCTATCCCAGGCACCGATCTGATTGTACAGCGT
GACATCACCCCGGGTGAACAGGGTGTATATAACAACCTGTCTGAAATGGGTTCCTGGATGGACAGCCCAAACGCT
TCCCCGACCAACGCACCAGAATCTCTGACCGATGACCACTCTGTTCTGACCACCCTGCTGAACAACAAGGAAGGT
CTGCAGGATACGGTTCCGTTCCCGCTGGCAGTAGGTAAGGCACGGTCGTGACTAAAACCCTGGATCCGGATATT
GATACCTCCAAAATCAAAATTCCACTGGAGATTGTATTCGGTTCTGGCTCTATGTACGGTTCCGGTATCGGTTGGT |

| SEQUENCES |
|---|
| GGCTCTAGCACCATCTCCTCTTCTATGTCTGATGACGGTTCCTCTTCTATTGGTTCTACCACCCGTAAAAACCGC
GCTGGCGAAATTATCAGCCGCATCGCCATGAACCAGAGCCCAGGCGCGGGTTCTGGCGGTCAAACTGTGGTGGGC
GGCCTGGGTAGCGGCTCTTCTAACATTAATATCTCTGGCGGTCGTGGTGGTATTGTTTACGGTCCAATGCCTAAC
GTTAACGTGGTGGCAGGTGACGGCCTGAACCGCCTGCAACTGGGCAGCGGCATCAACCCGCTGGCGCTGCTGCAG
GAACGTATGGTGAACTTCAGCGCGGCACAGCTGGAACATCTGCATGGCCAGCTGACTGGTATGATGGCAATGATG
GAGGCAATGCCGGGCGTGGCTTTCGAGGGTGCTTCCGTACAGATGACCCTGCCTGAACCTGGTGATACCCAAACC
ATGCCGTCCATTCGTCGTGTCCGGTTTCGGTGAACCGCCGCCTGCGTGAAAACATCGGCCAGCCGGGCCAACCGCCT
ACTCAGGAAGCGTTCGACGCACTGCGTAACGGCCCGCTGAACGGTGTGTCTGAACTGATGAGCCAAGTTCAGGAA
ATGATCACGGTACGCTCTGAAGGCTCTATCTCCCTGTCTCGCTCCAGCAGCCTGTCTGACCTGTCCTCTGAAATC
TAA |

SEQ ID NO: 23
Name: Law 0460-PEBP
Length: 516
Type: Synthetic Nucleic Acid Sequence
Organism: Synthetic
TTAATTAAtaGAATTCacTCTGAACCGTTTACTCTGTCTAGCCCTCAAATGAAAAATGGCACTATCGCAACCAAC
CAGGTTTACAACAGCTTTGGCTGTAAGGGCAAGAACATCTCTCCGTCTCTGGAATGGAAAAACCCACCGGAAGGC
ACGAAAAGCTTCGCCATCACCATGTTCGATATTGATGCCCCGACGGGCAGCGGCTGGTGGCATTGGATCGTTTAT
AACATTCCGACTTCTACCAGCTCTCTGGTCCTGGGCGCAGGCAACGACCCGAAAAAGCTGCCGAAAGGCGCTGTT
CAATCTATTAACGATTTCGGCTTCATCGGCTTCGGTGGCCCGTGTCTCCGGTCGGCGCGAAACTGCACCACTAT
ATCTTCACTATCTACGCTCTGAACGTGGAAACTATGGATCTGCCGGCAACGACTATGCCAGCTGCTATTGGTTTT
AACATCCACATGCATATGATTGATAAAGCTACTTTCACCGCGACCTATAGCCGCAAGTAAGGATCC SEQ ID NO: 24
Name: Law 1082-FeoA
Length: 363
Type: Synthetic Nucleic Acid Sequence
Organism: Synthetic
TTAATTAAtaGAATTCacATGTCTGCCGTTGTTGATTCTATGACTCCTTTTCCGTGCTCTGAACACGATGAGCTG
CCTGTTATTAACGAAGCCACCGCATGCTGTGTTTTTGACAAGGTTGAGAGCTACATTTCCCTGCGCGACCTGAAG
GTGGGCCAGCATGCCCGTGTGGTTCGTGTGCAAGCGGACGGCGAACTGGGTCGCGGTATTCGTGACATGGGTCTG
GTCCCGGGCACCGAAGTAACTATCGTAGGCCGCGCGCCACTGAAAGATCCGGTTGCCCTGCGTCTGCTGGGTTTT
ACTCTGAGCCTGCGTAACTCTGAAGCTGATTACGTTATGGTGTCTCCGATTTCTTAAGGATCC SEQ ID NO: 25
Name: Law B004-Fluf
Length: 2739
Type: Synthetic Nucleic Acid Sequence
Organism: Synthetic
AAACAAAAGATCTACGCGGCGGATGTATTCTTTGAAGGTCGTACCGAAACCCTGATCAACGTGAACAAGCCGTTC
GACTCTTTCTTTGGCGGTAGCGATTCTACCATTGGCACCCTGGAAACCGGCCCGACTAACCTGACTTTCACCACC
GTTGGCGCCTTTCGTAACTCCGTATTCCGTATCATCGGCGGTGGTCGTTCCAGCTTCAACAACCCGAACACTGTG
AAAGGTAACGTGACCCTGACTGTTTACAACACCGACGTTGAACGTATCATCGGTGCTGGCATCTCCAACCGTGGT
CTGGTGACCGTGACCGGTTCCGTTAACATGAAACTGGAGAACTGGTTCCGTCACGCGTGGTATCTACGGTGGCGTT
TACACCCAGAACGGTCACGTGCTGGGTTCTATCAACATGCACCTGAAAAACGTGCAGACCCCGCTGCTGATCGGT
TCTGGCGTATCTAACGGCCCGAACCGTATTACCGTAAACGGCGACATTAACATTGACGTCGAGGATAGCCGTATC
CAGTACGTGAACATCACCGGCGAGGTAGATGCAGGCATTAAAGGTAACGCAACCCTGACCGTTAAAAAGAGCACC
GTGGAACTGATCAACAGCGGTCGCGGCAACATCCTGGGTAATCTGAAAATCTCTATCGCAGACAGCAACATTCGT
GGCCTGTCTCCGGTCGACTTCGGCAGCTCCGTATACGGTGACACGAGCATCAACGTTATTAACTCCCAGATCAAC
GACATCACCCTGATTCCGCGCGCAGGCGGCATGCTGGTTGGCCCGGTCACTCTGGACATTACCTCTTCCACGATT
CAGAACATTCAGTGTGGCCCGGTGTCCCAGAACAACCAGCTGAATACTCTGAATGTGACCGTAAACACGTCCAAT
ATCACCAACCTGAACCTGGGCTCTGTAGAAGGCCATACCATCAGCACCACCGCGACCGTAACGGATTCCAACATC
ACCAATCTGAACGTCGGCACCTTCAACGCCTGGGTGTTACCGAGAATGCATCTGTCATTATTAACAGCGGTAAC
ATTACTAATCTGAACGTAGGCACTAACGTTATTGCGGCTGCGACTACGATCAATTCTTCCGCTACCATCCACGAC
GGCCTGATCGCAAACCTGACTCTGGGCAGCCAGGGTAACGGTCGTACTATGATCGCTACCGCTAACGTCAACGGT
GGCACCATTGGTCTGCTGACCATGGGTTCTGAAAACTTCATTCCGGGTACCCGTCAGCATCACCGAACTGGCGATC
CTGAACATGAGCGGTGGTCTGATCGAACGTATCATTGTGGGTAACGCTAATTCTTCTACTATTAACTTCACGCCA
GGTAAACGTTCCATCGTAAAAACCATCAATGCCCGGAACTGCCGTACCTGGTTAATATCCAGAAAGGCGCGATG
ACTCAATGGGGCACCAAAAACATGCCGTTCCTGCTGGACACCCGTAACCTGATTCTGTCCGGTACTCTGATCACT
AGCAACATCCAGTCTGGCAGACCTGAGCATTACCAATCTGTTTGTGGCTAATGGTGGCACCCTGGTTCCTCGCAAA
CTGATTCCGGGTAACCAGCCGGTTATTCAGTTCCTGGGGTGGCCGCAGTCTCTGCTGGTGATCCATCAGCCGCTG
AAAGTAAACCTGAGCCTGTCTCCAAAGCTGATCGGCTCCAGCATGGTCCCTCTGGCGTTCGTATCCCAGTCTTTC
AGCTCTCCAGATCTGTTTGTGAAACAGACCCGCTCCGGCCTGATTGGTCCGATCTGGAATTTGACCCAACGACT
AGCATCTGGTACGTTAACAACATTCAGGCGTCCCAGGATTTCTATAGCTTCAGCATTGCGCGTGAAACCACCAAC
TGGCTGCGTCAACAGCATATTTGGACCCTGCAGAACCGTTCCTCCAAACTGCTGGACAACGAACACTACGGCCTG
TGGATTAACGTACAAGGCGGCCACGAGTCTCTGGACACTTCCATCGGTAGCAAGGCAAAAATGCCATGGATCATG
GCTACCGCGGGTTATGATTATCTGCAGCAACTGCCGCGTCTGGACATGAAAGCACTGTACGGCCTGGCATTTGGT
GCCTCTAAAGGTAAAAGCAAGTGGTCTTCCGTAAATAGCACTAAGAACGATGCGAACTGGGCATGGTTTCTGGT
TACGTCGGTCTGATCCACAACAAAACTGGCCTGTATAGCACTCTGACTCTGCAGCTGGCTTCTTCTAAACTGCAT
ACCAATAGCACGGGTTTTTATCGTAACTTTAAATGGACGGAAACCACTCCAACTGAGGCGCTGGAGCTGGGTTGG
AAATACACCTTTAACAATGGCATCAAAATGAACCCTCGTGGTCAGCTGGATTTTCGAACAGACTAGCAAACACCAC
TTCGACCTGGGTATCCAGAACGACAAAGCGATCCTGGACAAAAGCCAGCTGATCACCAGCTCCCTGGGTATTACG
GTTGAGTACAAACTGCCGGTCACCACGCCTATCAACCTGTACGCAGGTATCGAGCGTATTAAAGGCCAATCCGGC
AACTTTGCGATTTCCAGCCAGTCCCTGCAGATGAAGTTCAAGCATGATAACGACACCAGCGTGGTCCGTGCTACC
ATCGGTACGAACATTCTGCTGGGCGAGCACTTCAACATCCACTGCGATATCTTCGGTGACAAAGGCAATGACAAG
GGTATCGGCGGTCAGGCTGGTTTCACCTACAAATTCTAA

SEQUENCES

SEQ ID NO: 26
Name: Law 1153-OmpA
Length: 1140
Type: Synthetic Nucleic Acid Sequence
Organism: Synthetic
TTAATTAAtaGAATTCacGGTAACACTAATCGTGCTACTGGCTCTATGAATGGTCGTAATCTGACCCAGATCAAA
ACGCCGCAGAGCATGATCGACAACGCGTCTGAGGAACTGACCACCTCTCTGGAAAGCAAATCTTCCGACGACTTC
GCGATTAAGGATCGTAAACGTCAGGGCAAGGGCTCCGACAGCCTGCTGAAAATGGTTCAGGAATATACTGAGCTG
ACGAATGATGACACCCGTAACGCGAAACGTGCGATGCTGTCTCAAGTGCTGCGTGCTAGCCAGTCTAGCCAGGAC
GTGCTGGAGAAAACCCTGGAGCAGTTCTCTAACAAAACTGACGCCTGGGCGTCTCTGGCCGAAATCGCACAAGAA
TACGGCGCGGAATCTCCGCAGCCGACTGGTCTGAAAAGCGTACTGGACGCCATGGAAACGCTGGAAAACGAGTTC
GGCGACGAGATCAAAGCAGGTCTGAAGGGCGCCCTGAACTCCAAAGAGTTCACTGATATCGGTAGCGCTGCTCAG
CTGCGTGACCTGTACACTACTACCGTCACCATTACCGCTGCACCTGATGCAGTACTGGCCCGCCTGCTGGAAGAA
TATGAATCCGATGACGACCTGGACCGCGCGATCGATTTCCTGCTGTCTACTCTGGGTGGCGAACTGGAAAGCGCA
GATCCGAGCATGGATAAAGTCCACCTGCAATCTGTGATGGGTGATATCGAGAAAACTCAACAGCTGCACAGCTCC
CACAAGCAGTGCACTACTGCTCTGAGCCGTTGGAAGGAAAAACACAAGGGCGGTGGTGAGAACTCTACTCTGACC
CCGCTGGAAATGATGCGCGAGCTGATCGCACTGAAAAACGAAACTTCATTTCTCCTTCCTCCATCGACAAAATT
GTGGACCAGGCAGACCCGCAGGACATCGAGAAGAAGTTCTGTTCCTGCAAGAAATGCTGGCTGCCGTGCGTAAA
TTTCCGATTATGGTATTCGATAACGTTGAAAACCGCTTCGTGTAATGGGTGCCGTTCAGGATGCGGTGGACGAT
GCCGTACGTCGTGAAGATGAGTTCCTGTTCCAGAAAGAGCATCCAGATGTGCCGCTGCAGCCGGATGAAAACAAC
ATCCAGTAAGGATCC SEQ ID NO: 27
Name: Law 0033-OstA
Length: 2421
Type: *Lawsonia* Nucleic Acid Sequence
Organism: *Lawsonia intracellularis*
ttgtataatctttttttaccatttattctaactaaccttatatattatataattattccatccttatttatagca
tttttttcctctacaagcttatctattataaacatatccgaatttgcacaaccagatattaaccaatctcaaact
aaatggaaccttgaagctgatacgttaactacactatcaaataatactattattgaagctaaaggaaacattatc
cttacaaaaggacaggatgtatttaaagctgactttgcaaggtattatcaaaaaacaggttggcttttccttaaa
ggtcatgtcactgtaaagatggatgaaaatgaaatcaatgctgacgaagcagaatttaatttgaatactaaaaca
ggctggcttaataatgggaacatatttatctcttcatcacatgtttacttttctggtgcacgtattaccaaacat
tacggagattattatactttaataatgtcaaagttactacatgtgacggacctcatccagcatggtcaatatca
gctaaagaggcaatagtagaagttgatggatatgcacaattatatgattctacctttaaaattaaaaacatagat
gtaatgtatagccctattttacaatacctgcaaaacaaacaagacaatcaggtttttaaatcctaattatgga
atcagtcagcgacgtggaatttattatactcaaccatactttttaaatattgatcaaagcagcgatctaacattt
tatgctggactgatgacaaaatggtcattaggaactgtaagatatcgttcacacaaatttacaaatcaaaaa
acatggtttgctgctagtggcattcatgataaaaataatattgtcacaccagggaaagatcctgtctatccatca
agccaacttgtacgtaataaccatcaacgttattgggttcgtggaatggctgatggtgatggtttttattggaaactcaact
tggtgctatatatctaatttagactatgtatcagaccaagattatcttagagaatttgatcaaggtataacaggc
ttttcacactcccgtagtgaaatgtttcaaatgtttggcagagatatccaagaagatgaccaatctcgattaaat
gctttacttattagaaaagattggcagcgtataggggtagtaggaaatattagatatgaacaagatccaacatta
ggacatgggaatcatcctactagtcaaagtgagttaacgcaacgaattccacaaattgacatgtttctttaccaa
ggaaaactatttcaacctctttcattagagggtgccattcatttacagtctgcttatatgtatcgtgctaaaggc
actaaaggttggagaacagaactttatccaaaagttacattaccaatcgatctcaaatatggatctgttataaca
actgttgggctacgtgaaacttactatcaaacaggtataaaatcacacacaagtcctgtagcaccacatgtccct
gatactaaaacaccacgtcaaacaggtcagcatcgttcactttttaacttacaactagaaagtagtacacaagct
caccgaatatggcgactaaaggataaaaaaactattaatcttcattctcaaagtataggaaaaacctttttgtaca
gcactcaagcatacaatccaaccacgtatatgctatagctttatacctagagaaggccaagaaaaaaatccattt
tatacactatcagataggatccttccccaaaatgaccttacttattcaatagtaaatattctcacaaaaaagaat
gttactattagtgtagataataataataataatgataataagtgttacaccaacacttattacttcctactat
gatcttctctactggaacttatcaacaggatatgattttgaagaagaacgccgaaaacaatatgtagaaaaatat
ccaaagcgccctataaaagacatctattctgaactagaactttatatactatcttggttaacttattcaggtaag
acatttatttctccatataacggtaatattactagacatgatcataatatcatattcaaatcagacagattttct
tggaaaacaggccttagcttttcgtgatcaatactataattacggtgagcatcttcaatatcgagatgaaaataat
attattatgtctagtaggttacgcttacttcaaaactctttttctatacagctattaccaaatgtatctgttacg
ttagaagatttccgaaacctacgagaacttggaacttttggtaaaacaaactctcaactagttgaagttacatat
ttagcacaatgttatcgtattattggtagataccgatatgacggctatgatcgtagctatacagtattaatagaa
atacctggattatttgaataa SEQ ID NO: 28
Name: Law 0691-PAL
Length: 489
Type: *Lawsonia* Nucleic Acid Sequence
Organism: *Lawsonia intracellularis*
atggaagtatttagacgttatggcatagttctggttctgttagtagtattaagtgcaggttttggttgttgtaaa
aagagtgttgatgtagaacaatctttagcaacggagtgtattgctccagcaccagcaattaatgcagctgcagaa
actataactgatgggattatttattttgattttgataaatatgatattaaacctgaatatcgtgatatgttgcag
aagaaagctgaacttttaaaagaatatccttgtattcgtgtccgtatagaaggtaattgtgacgctcgtggtact
caagagtataatttagcacttggagagcgtcgtgcacgtgcagcatatgaatatttagtcatgcttggagtaaat
ccatctcagcttgagataataagttttgggaaagagcgtccagctgttgaaggaacagggccagctgtatgggca
aaaaatcgtcgtgatgattttcgtattattgccaagtaa SEQ ID NO: 29
Name: Law 0995-OPRM -continued

SEQUENCES

Length: 1380
Type: *Lawsonia* Nucleic Acid Sequence
Organism: *Lawsonia intracellularis*
atgaaaagattgttactctgtattataacatgtgttattgtatcaagttgctcttttgctccagattacaatcga
ccacatttagagttacctgagggtatgggttagttcaccagagacaggagttcctgcttctatgcagtggtggaaa
cgctttaatgattctacacttgatattttagtagcagaagctttgcagcataatagagacttaattgcagctgtg
gccagagtagattatgcacaagctcagttaggagttgctcgatcagattttgtttccacatttttcaggaaatgct
caagcaacacctgtatgggtagatcataagagggttacagatggacaatctccatatagcgcaaacttttcagca
agttgggaaattgatatttggggaaagatacggaatgccaaagatgctgcatttttctcaattaatggctacagaa
gcagaaaaagagggtgttttttctttctattgctgcccaaacagcaaatgcttatttttgttgaggagccttgac
ttacaatgttctattgcagagaggacagtaaaaacacgtgaagatgcattaagtatctatactgcacaatatcaa
aaaggatttattaacaaattagatttaactcgagcaaaaacagagttgagacagcacgtacagcacttatcaa
aaacgtattgcacaagagaatgctgaaacagctttatctgttttgttaggccgttctccacggttaattatggac
acagcaattgagcgtggggtatctatgaaagatttatcttgtattcctgttattcctcaaggtattccttcagag
cttttagaaagacgtcctgatatacgtcaagctgaatatacgttaaaagctactagtgcaaatattggtgtggca
agagcagcttggttaccatctatttcattaacaggattatttggtattgtaagcccacattaagtgatttatta
aaaaatccttttaaaaacatggagttatggggaaactggaactgtgcctattttagattttggtcaggtatactat
aatgtggaagcagcccaggcaaaagaacgtgaagcattagctaactatgaaaaaacagtacaaaatgcttttaaa
gatattcatgatgctcttatacggcaatatgaatcaaagaatatagttaattcacttgaacgaatggtgaaagag
ttacgtatagctgtacatcttgcacgtactctttacgataatggttatacatcttatcttgatgtgttagatgca
gaacgtgctcttttcaaagtgaactagatcttgctagtgcttggagtgatcgcctatcttctattgtacaagtt
tgtttagcattaggaggcagttgggaataa SEQ ID NO: 30
Name: Law C046-SLH
Length: 2391
Type: *Lawsonia* Nucleic Acid Sequence
Organism: *Lawsonia intracellularis*
atgtataaatttattatattttatattatatgtatatatgaaacaatagccatatatttactcttaggtagtttt
atatcctatttttaatagagtctttcttaaaaaagaagtaaaaatattagatactactaaagtaaaaaagtatgct
agaataggaacatttattttttgtatgtaataataagttctcaagtatcgttatctcataatgctcgtataggc
tatgaagataaaaatagtgataggaagagtaaactgattttacataacaaattacaagtaaatgagtttgatgag
cttcgttcagatattgtagttacaatgacaccattaaatatatacttctactcaggaaaatagaaattacaact
atagaagccaacctttaagattagaggtgatacagcgaacacaacctgtgcttttagtagatgtcgaaagcagt
cttcgtgacatatatcttctactggacgaagctgaagggtgtaatagagaagtagaaagatgtcttaaaatatgg
gaaacagtagtgaacatacaaaagtactgcatcgtcagactagggagcgtttatctaatgcagtaatagagtgt
caaccagggttacctactaataatgagggtaaagtagtaagtgtaccagaaaattgtggcttccattgaaaat
aaggtgttacatacagcaaatcaacaaagaactgcacgaaaaatggaagtagctatatcacgcactaaaaaataaa
aatattttcttggggaataaacaaaaactacttaggtatcgaattgaagtactgaaagcgcgtgtagaaggtaat
cctgatcctcctataacctatacttacaccacaagtgcttgaattaccacttttacctgatccaccaccatcacca
ccaccattgccacagcagacttttcaattcccagattttggagatcctcttccggaaccattgtctctccttagga
gatgatcctccccaaaatgtactaaatcaagagcctcagccaggaccatcttctgagattgtctcaacttttacag
ccttcaccttcagtagaggatctatctagttcaggagtgactttagaatgtcaagaagagctttctagcagtgat
gaggagatattagatgatgagtgtttaacctctggcgatgaatcttcaacatcagatggtgagtctcaaaggtca
tcaccgccaacaaaacgtaggaagctaactcatactccaccaccttctgatagaggctctcctccaggggagttct
tctatgcttatgccatattacacatatggacaagtcagttctcttcaaggattacaaagtacgttaatgagttta
gaggatcagttagcaacacaattacgactatctattattagatccattaatgttttaggtgtttgttgtaaggac
gacaatcagttacaacctcatacttttcaaagtaaaaaacagactaaaattaaaggaggaataggaagaagtcac
tcaacagataatgaaatacgtccaacttctgtgaataattcattattttttcgcagcaatggcatgttattgca
tctatggatagtcgtatatctaatttagagactactatttcttcaagacaagcaggggttttttacaacacctatc
gatgggactctgtttatcttttattgtatagtaataacaaaaagaaaactcaaaatttctatggagttgtactagac
tcagtagatggttctgcaaaagctcagatagaaacagataacattttagcaacagtgacatggaataaagaacat
caaggttttttcaggtcatttagcaggttgttatgggtggggaaaataacaaatattcgtacaatacatttttt
gataacgaaagtgtttctaaaggtatttcaagtatacatatgagtggtggatttattcagctaggatataacgtt
ttactaggaaaaaattattttcttattccatatgttgaatatatgagattagcagtagcatgggatccatatgaa
gaacatacaggtcttattccttgtaaagtgagtggacataaagttcatgtttgtgagaaaagtataggtttgcgt
aatcaatggaaaattacagataattcccagctacagtttgggtgttctcatatttttacaaatcataatacaggt
gaaatagcttctaaaccacttagtttatctgactataggaataaaatatctattcctggttataagaagcaatat
atccataggagcagggattcttatgagtcaaatgtaatggatacattatctatggagctttatagtaagtta
agggtaactaaaagcataaaagatgttactagttatacaagttttacaataagatacgtttattaa SEQ ID NO: 31
Name: Law 00147-SlyB
Length: 459
Type: *Lawsonia* Nucleic Acid Sequence
Organism: *Lawsonia intracellularis*
atgcagcgttgtggtctttatatcatttgtttagtgttatctataggtatgataagttgtgcaaatttttagtgct
tcttcttttggagggaagcaaattcgtagtgcacatattgttgaatttgaaaagtcgtttctgtaaaacctgtt
gaactagaaggaaataccaattctaggtactattactggtggagctgttggtggtgttcttggtagtttaatc
ggtggaggatcaggaagaatattatcaactgttgttggtgctggagcaggggctgttgctggaaacattgctgaa
agaaaaattacaacgcaacaaggtctcgaaatagaagtgaaacttgataatggtcaaatttatttctatagttcaa
ggtgctgatcaatccttttagtcctggcgaacgtgttcgagtactacgtgaagtgatggttcggctcgagtatct
tcaatatag SEQ ID NO: 32
Name: Law 0050-AsmA
Length: 3228

-continued

SEQUENCES

Type: *Lawsonia* Nucleic Acid Sequence
Organism: *Lawsonia intracellularis*
atgagatcttttctcattagtatagttactctctttctattaggaattatagtatttttggtattacattctac
tttatcaaacaacatccacaatatattacaaataaaatactttctactatttcaaaacaattaaaggatacttct
atttctgctaattctattgggtttcatattgtaccttttcctaagctttacttaacaaatgttatacttcaaaca
caaaaaggtgatacaattcatattaaagaatgcttgattactccaaaaatcaccaacatattatcaggaaacatt
tctatatattctattgaggtaatccaaccaatagcctccattattcttcaaaatgaacaaaaaaaaaatagtaaa
accacaggatatgctataccaaaacaagtttcgcatcttctccaattaattacagatagtaaactttttattgaa
aatggtagtattacctttcaaaataatgactattgttttaagataataggtattaatggtaaaattggtgtttct
aagacacttacaagctcattaaagctcactgcagatgaaataatctgggaaataatgaatactgtaagtaataat
tctagcactgcacaaaaaagtattgaaaaagtacagctccacatagaggatatgccgtataaaataaatacagca
ttacttcatgatacttctcctttatacgatttatttacaaatactaaaaaaactacatttaaggtttcaggggct
atacctacaaccaatacagctaataacattacattcgacttcacgacaaaactagaaaaagataactctgataaa
cttacaatgcatgggcagttacatattgaaggaacactccctaatggtaatacatccattcctatactattatct
gttccgtttacaacaacatcttctgaggacatgacacactttcctccactgctgataaaaaactcaaaactactt
tttgataaaactcatatagatcttcatggaacaataaaaaattatgatacactatcaaatctctttttgatgga
acaatggatgtaaaaaattttagttttccctattggtttacttttgcaaggcaactaccaaatggtattcaacat
gctcttaatcaattatctggagaaataaaatttacattatctcctcaacaagttaatgcccaaaaaataatcatt
cattctttagatactacatttcaagggaatggaactgtcaataatttttttatccccaacgattacattatccctt
gccacaaaacagttcaaccttaatacacttcttccagaactaaagggtaaaaaatettcacaactatcctatcct
aaagaaacgtttttaactatcttaagtaatctccataataataataataataatataaaaaaaacaatcaac
tatgacattactattcaggctgatcatgtaacatgttggaaatttgatggatatcagtttatatgtaacatacaa
cctaaacctcagggtactcagattcatactaactgtaaaaatttttatgatggcagtttatcttcctcactttta
ctatctaataggcacacaatacaattagctatagaaaatattcaactgtctgatataacaaatattattacaaaa
gaatatgaactaaaaggtaaagcttctggcacaagtcgtgttaatggacatggtgatactttagcatcatttctt
tcaagtctaaaaggtacaattgatttatatgtaactgatggattagtaaaaaaaacagcgtctgaagctattcct
ttttctatgcttcatctaacatgtgacagtattggtcaaccatcaaagggaaataaatcctctacaattccatat
aaagggaagtggagtgcagagatatcatcagcaagatggaatggctcaattacaatggatgggttaatacaattt
tcaaccactgactggctttctattaaagcagaaaacataccatcaaaagttgtatgttctgtatctggcgtacaa
gctgtggcttatggaggaatatcttttgacatagataatagttttcttagcttctctaattttcaaggtgaaata
catcctaaaacagccctatctggaacaatcaaaactagttctagtacaagtaacacaagacaatgggagggttct
ctcactgtcatgacacaaaatcttagaaatttattaagtaaacttggttatgaaccaaaaaatatttctccaact
atgttgcaatattgtaaattgcaaggagatatctttatttctcctgcaacaattcgccttacaaatatacaggga
atattagataatacactgattaaatttctctcaatggattacagacaaaccctccaagttggacaggagatatc
caactaagttcattaaacttagataaatatttactatcaattaaccaaaataaactgaaaaaatcacaggaactc
tggccgatagaattgctgaataaagtaaatattcaatctacactgactctagctgagcttatctatagaaaagtt
ccatatactaatgtagtagtacccattagtcttaatcaaggaacattatctatcactccaattacagcatcacta
tgtgatggaaaaacagaagcaagctttaaggcttgccctctttcaactaatggcaatagtgcacagatagatttt
cattatatttcaaaaggtgtggatatgattaaactaagtaaaaaacgtcaacaagaatatcttatttcaggcctt
ggtacatttgttattaatatacagtcaatagcaaaatcatctatagatttccttaaaaatcttcaagggaaatgg
cgtatttttatccagaatggctatttcaaaagaaacaccactactactcaacaaaattttagtaacattggtgca
acaggaaatattataaatggtattattacaaataataattttgcaataacagggcctggaatggtaataacaggg
agtggaaaaattgatcttcctgaatggaatcttgactacctcatcactatagatatggaaggatttcctatagct
atccccataaaatatacaggaagtatagataacccaaaaagaacaattaatgcggccaagttaattcttagtact
ataggttctcttgggagagatactataggattaatacaagatatttttcagctccactgaagttacttcttccc
taa SEQ ID NO: 33
Name: Law 0065-LoIA
Length: 750
Type: *Lawsonia* Nucleic Acid Sequence
Organism: *Lawsonia intracellularis*
ttgaagaatattataaatactataatttttcctaagcaaaggaacaaaaaaatgtcacaaaaattttctatgcta
caactaatattattttttttaacttttatattttattcatatataacagatagttatgcagagtctataccaata
gtaaaagaattacagcaatcatatcaatccattaaaaacttttctgcaacatttactcaagaacttactcatcaa
gaaagtgggtccaaagaaacacgtattgggaaactctttttttaaaaaaccacttcttgtcagatgggaaacaaac
acacctcatgaagaacttcttettattaataccaatgctgtatgggattatcttcctgatgaaaaccttgtttat
aagtactctacagatattgtaaaagattccacatctattattcaggttattactggacaagtacgacttgataaa
aacttctcaattattgaaaataataataataataataatgagctaatcttccttaaattatacccaaaagaacca
acgactcaaatggttgaggcattttttatggattaataaaaaaagtttactcattcacaaagtacaatcaattgat
ttttatggaaatacaaatactattacttttattaatattacacccaatactcatattgataataacatatttcaa
tttactccacctaaagatgttactatagaaaatttacaagattcatctacaccagaacgaccactatttaattag SEQ ID NO: 34
Name: Law 0649-OmpB
Length: 2466
Type: *Lawsonia* Nucleic Acid Sequence
Organism: *Lawsonia intracellularis*
atggcatacctatctatttcaaaaaatcaatgtaagtctttttttaataactctagtaactatatttataatgaca
tcaataccacaactagctgaggctgttgaacactttgctaatggtgtccccacagtagtacaagatgttaatgtc
ccagctgactcatactttggtggtgctgactcagctgtaggtccaaacccaatagcttctactcaccttacaatt
tctacaactcaagggtttggacaaaatgcactagaatttgttgtgggtggtagccttgcaaatggtaatggaaat
ccagccaacataaatggagatatagtecttattgttgaaaatacaaatactcagaatagtattattggtggtagt
atggcaaatgctgcccctgtaactattggtggctctatttttatgactcttagaaatgttactgcagtagatcca
atttttggtggctctgtagatgtacgctttttcgcccaacagcaacctaatgaggatcaacttgtaggtggagat
attaatataaatctagagaatgtaacaactccagagttttatggtctaggctacgcaaatggtgtaatacctgtt
aacgtcctcaatagaaatttttttggtagctgttcagggaaatataactacaaatatttctaattctaacattgca

```
accgttatgttaggttcacactatgatacaactatggctgtaggaggtaatggaacaataaatgttgataattca
acaattggttatctttcagctagcaatagtagcgactttgttaaccctgacttaacaaacactgttacttttaat
attggtcccaacaacagaatagcaaatattttgcaagcaataatggtgttatcccacattttattgtaaatatg
gatggatctggaacagaaatacaagagttaacacttggtaatgtaattcgaggtggccttgtacttacttcagag
ctaaatctatctcaaggaacaataaataatttaatcactggtaatgaatattacgatagatcaggattaagaact
actgtaaatgttagaggaggtacaattggcgtattgacttcaggaggttctgactattcagaattaaacttcatt
cctggagaaatatccactatattagcaacaaattcaataggtaaccaagattttgcatctctttctcaagttaca
atacaccaaggtgctgaaactctttggggaatgagagatgaagtatttgaacttcaaactaacaatctacagtta
ggtggtgaactatttattcctgctgatggaactggaggagtagccctaatcacaaatcatattattgcaaattca
ggtgtgataactccggtaaatgtctccagaaaggatgacccctatcattggattttagaacctactggtgag
gtagcacagttaacaatatatggaccacttacagttaaccttagccattctccagaaattcttgggaaaattatt
acacaacctatccctattgcagttactaatagtgatgtttttggtacttctaaactatttgtggaacataacaca
aaaggactaatttggagtgatatcatttttaatcctcaagataaaacatggtatctaactaactttagaggttct
gaagacttctacggactttcagcagcacgggaagcatctaattggttaagacaacaacatatctggagcctacaa
cgtcgctctaataaattattagatcatggtgtagatgggttatggatgaatgttcaaggtggttatgaaaagctt
gatgcagcaattggtgatgctaagatgccttggattatgcaagcttaggatatgattttatgcataagttaagt
gattttttataacttaaaagcactttatggattcggatttggatttgctacaggtaaaaataaatggaataccata
aactcaactactaatgatatctacatggggctggttggtgcctatgttggccttatgcatgaagccacaggcctt
tatggtacagtatccggacagtttgcaactaaccgtacaaaaacaaaatgtacaggctttgatgaaacctataac
gaaatggagcattgatgagtttaaaataaacccacgtggacaagttattttttgaacaattatctaaacatcactt
tagtcaaccgttataggtatctctggagaatatgatttagatttaagaagtaaaataataaagcttcaagctagt
gttgactggattaaaggcatctctggtgactttgcagctaaatccgaagttcttaatatgaagtttaaagataaa
aatgatactagtacatttagaggaacactgggtgctagtgcacaacttctagaaaactttgaagttcaccttgat
attttggtgatcttggcaatgataaaggtattggtggacaggtaggagctacttatagattctaa SEQ ID NO: 35
Name: Law 0043-PtfH
Length: 2703
Type: Lawsonia Nucleic Acid Sequence
Organism: Lawsonia intracellularis
atgactaaagttggtggtagtaatccttttcaacacttgcatcaatggttggctttagcaaatcttcttccagc
tcatcttcaagtaaggtagctgaattaaaaagtaaatttgaagcacttgggacactaacaaaagcaagtcctcgt
cctgcaaatggcactcaggatactaatcgattaagtgatagactatttaggaggacactatacagttcctgctaat
acagcttcaagagtaggtggtcatcttcagcgggttgatgacaataaaagtagcagttcagcagctaatgttgca
aaaagagctgcagcacattcttcttttgcaagttcaaacccaggactccaaggagctagcggttcttcttctgga
ggaacaggcggaagtataacagatcaagttaaaagtaggggaattactgcaaggaattttttcggattctaataat
aattctataggatcagggtcaagcagtggaagtatattatgatcaggttcaggatcaaggtattactgccagagga
tcatctatttcttctggtaatgcatcaggtactagcaatgttaatgatggaacaagttcaagagattatggagct
aatgtccgtaatactcgtgaaagatttgaagctggtcctggaggtgctcaaggagagtctcctggagtaaaagat
gctaaagaagctactaaaggagttagtgtttctaatttaagaggaatatttgaaggaagaggtggtcagataat
aatcaagtaggtagaagctctggtggagtttcaggagcatcaggatcagggaggagctcaagggacaggaggaaca
tcgggattaggtggagcacaaggtacattaggaagtggaggtcttgatggaggaggagtttcaggtgctgctggt
ggaacttcaggcgcctcaggagccggaggagcaagaggtactgctgatggaataacgtctcctggagcaagagaa
gcacaagaaactattaaaaatgctggtgttagtgtaagagatttagctggaagatttagtggagctcaaggtaca
agtggagcttcaggagcagcgggagcttcaggagcctcaggagccggaggacagctggtgcggcaggaggttgga
ggtcttgatagaggaggagtttcaggttctgctggtggaacttcaggcacctcaggagccggaggagcaagaggt
actgctgatggaataacatctcctggagcaagagaagcacaagaaactattaaaaatgctggtgttagtgtaaga
gatttagctggaagatttagtggagctcaaggtacaagtggagcttcaggagcttcaggagcagctggtgtggca
ggaatgccagcaggtagtggagatgttgttgatggactaagaagaggaggaagatactgtcgatggatttgga
agaaatcagggtagtggtcctatccctagttctgcagattttgtagatggtcctataggcggtatacaaggagct
ggaggagcttcaggagcagcgggagcagctggtgcttcaggagcagcgggagcttcaggagcagcagagccactt
cctactaatggtacagatcagcagatagctgaagtcgttgtaagaaatgcagaaaatggtcattttgatggtatt
gatttctcgacacagcctggtggtgtagaatcaaatacaggtagtatccctggaacagatcttattgtccaacga
gacatcactcctggagaacaaggagtgtataataatctcagtgagatgggatcatggatggatagccctaatgct
agtcctacaaatgcaccagagtctcttacagatgatcatagtgttttgactacactacttaataataaagaaggc
ctacaagatactgttccttttcctcttgctgtgggtgaaggcactgttgttactaaaactcttgatccagacatt
gatacaagtaagattaaaatcccacttgaaattgttttggttctggaagtatgtatggttctggtattggagga
ggtagtagtacaattagctcctcaatgtctgatgatggaagttctagcataggatcaactacacgtaaaaataga
gcaggtgaaataataagtagaattgcaatgaatcaatcacctggcgctggtagcgggggtcaaactgtagttggt
ggtcttggttctggtagtagtaatatcaatataagtggtggacgtggtggtattgtttatggaccaatgcctaat
gtgaatgtagtagctggagatggccttaatagactacagcttggtagtggaataaatccattagcacttcttcag
gaaagaatggttaattttctgctgctcaactagagcatttacatggccaacttacaggtatgatggctatgatg
gaagctatgcctggcgtagcatttgaaggtgcaagtgtccaaatgacattacctgaaccaggtgatacacagact
atgcctagtataaggctatcaggttttggagagccaaggttgcgggaaaatataggacagccagggcaacctcca
acacaagaagcatttgatgcattaaggaatggtccactaaatggagtaagcgagttaatgagccaagttcaagaa
atgataactgtaaggagtgaaggaagtatttcactaagcagaagtagtagtttatcagatttaagttcagaaata
taa SEQ ID NO: 36
Name: Law 0460-PEBP
Length: 552
Type: Lawsonia Nucleic Acid Sequence
Organism: Lawsonia intracellularis
ATGAAAAAACTGATTCTAACTTTTGCTTTATTATTAGTAACAAATATAACTACTTTTGCTTCTGAGCCTTTTACT
CTATCAAGCCCACAAATGAAAATGGAACTATTGCAACTAATCAAGTTTATAATAGTTTTGGATGCAAAGGAAAA
AATATTTCTCCAAGTCTAGAGTGGAAAAATCCTCCTGAAGGAACTAAAAGCTTTGCTATAACTATGTTTGATATA
GATGCACCAACAGGTAGTGGATGGTGGCATTGGATAGTTTATAACATTCCTACATCCACTTCCTCATTAGTACTA
```

```
GGAGCAGGAAATGATCCTAAAAAACTTCCCAAAGGTGCAGTTCAATCAATAAATGACTTTGGTTTTATTGGATTT
GGAGGACCTTGTCCTCCAGTTGGTGCAAAACTTCATCACTATATTTTTACTATCTATGCTCTCAATGTAGAGACA
ATGGATTTACCAGCAACAACTATGCCTGCAGCTATTGGATTCAATATTCATATGCATATGATTGACAAAGCTACT
TTTACTGCTACTTATTCTCGTAAGTAA

SEQ ID NO: 37
Name: Law 1082-FeoA
Length: 339
Type: Lawsonia Nucleic Acid Sequence
Organism: Lawsonia intracellularis
ATGTCTGCAGTTGTTGATAGTATGACACCATTTCCTTGTTCAGAACATGATGAGCTTCCAGTTATAAATGAAGCA
ACAGCATGCTGTGTCTTTGATAAGGTAGAGAGTTATATTTCATTGCGTGATTTAAAAGTAGGACAACATGCTCGT
GTTGTACGTGTGCAAGCAGATGGAGAGCTAGGAAGACGTATCCGTGATATGGGTCTTGTCCCAGGGACAGAGGTA
ACTATTGTTGGGAGGGCACCTCTTAAAGATCCAGTTGCATTAAGGTTACTAGGTTTTACTCTTAGTCTTAGAAAT
AGTGAAGCAGACTATGTGATGGTATCACCTATTTCATAA SEQ ID NO: 38
Name: Law 1153-OmpA
Length: 1197
Type: Lawsonia Nucleic Acid Sequence
GAGATAGTTATGGCTAATGTTAGTGGAATCCCTGCACCACGATTACTTTCCACAACAAATCAAATGACCAATGCA
GCTGCTGGTAATACTAATAGAGCTACCGGTAGTATGAACGGTCGTAATCTCACACAAATAAAAACACCTCAGTCC
ATGATTGATAATGCTTCAGAAGAATTAACAACTTCTCTTGAATCTAAAAGCAGTGACGACTTTGCAATTAAAGAT
CGTAAAAGACAAGGGAAAGGATCTGATTCTCTATTAAAAATGGTTCAAGAAATATACAGAGCTGACGAATGATGAT
ACCCGTAATGCTAAAAGAGCTATGTTATCCCAGGTATTACGTGCAAGTCAAAGTTCACAAGATGTACTCGAAAAA
ACATTAGAACAATTTTCTAATAAAACAGATGCTTGGGCTTCTCTTGCAGAAATTGCACAAGAATATGGTGCAGAA
TCTCCACAGCCAACAGGATTAAAATCTGTATTAGATGCTATGGAGACATTAGAAAATGAGTTTGGTGATGAAATT
AAAGCAGGACTAAAAGGAGCTCTAAATTCAAAAGAATTTACTGATATAGGCAGTGCAGCACAGTTAAGAGATCTT
TATACAACAACAGTAACTATAACAGCTGCACCTGATGCAGTGTTAGCAAGACTTCTTGAAGAATATGAGAGTGAT
GATGATCTGGATAGAGCCATTGATTTCCTTCTATCTACACTTGGTGGAGAGCTTGAATCAGCTGATCCAAGTATG
GATAAAGTACATCTTCAAAGTGTAATGGGTGATATTGAAAAAACACAACAACTTCATAGCTCTCATAAACAATGT
ACTACAGCCCTTAGCAGGTGGAAAGAGAAACATAAAGGTGGGGGGGAAAATGTACACTAACTCCTTTAGAAATG
ATGCGTGAACTAATTGCACTAAAAAATGAAAATTTTATTTCTCCTTCCTCTATAGATAAAATTGTTGATCAAGCT
GATCCCCAAGATATTGAAAAGAAGTCCTTTTTTTACAAGAGATGTTAGCTGCTGTAAGAAAATTTCCCATTATG
GTATTTGATAATGTCGAAAATCGTGTAAGAGTTATGGGTGCTGTACAAGATGCTGTTGACGATGCTGTAAGAAGA
GAAGATGAATTCCTCTTTCAAAAAGAACATCCTGATGTACCACTACAACCAGATGAAAATAATATACAATAA SEQ ID NO: 39
Name: Law B004-Fluf
Length: 2820
Type: Lawsonia Nucleic Acid Sequence
atgtataatataattaataagcatcaaatcataaaaattttattattttccttatgtgttttcttttttacactt
acagaaaaacaaaaaatttatgctgcagacgtctttttttgagggcagaaccgaaaccttaatcaatgtaaacaaa
ccatttgattcttttttttggaggttctgactctacaataggaacccttgaaacaggacctactaatcttaccttc
acaacagtaggagccttccgcaattcctgttttcagaattattggtggtggtaggtctagttttaacaacccaaat
acagttaaaggcaatgttactctaactgtttataatactgatgtagaaagaataattggtgcaggtatcagcaat
agaggacttgtaaccgttactggctcagtaaatatgaagctagaaaatgtttctgttactagaggaatttatggt
ggtgtctatactcaaaatggacatgtactaggctctatcaacatgcatttgaaaaacgtccaaactccactata
ataggttctggagtaagcaatggacctaatcgtattactgtaaatggagacataaacattgatgttgaagactct
aggattcaatatgtaaacattacaggagaagtagatgcagggataaaaggaaatgctactctaactgtaaaaaaa
tctactgttgagcttataaactctggtagaggtaatatcttaggtaatctcaaaatatctatagcagattcaaat
ataagggggttatcaccagtagactttggttcttcagtatatggggacacatctataaatgtaattaattctcag
attaatgatattactcttataccaagggctggtggaatgcttgtaggtcctgttaccctagatatcacaagcagt
actataccaaaatatacaatgtgggcctgtcagtcaaaataatcaactttaacacactaaatgtaactgttaatact
agtaacattactaacttaaaccttggtagtgtcgaaggtcatacaatatcaactacagcaactgttactgatagt
aatattactaaccttaatgtcggaaccttcaatggactttggagtaactgagaatgcctctgtaatcattaatagt
ggcaatattactaaccttaatgtcggaactaatgtaatagctgcagccacaactattaattcctctgcgaccata
cacgacggacttattgcaaaccttaccttaggctcacaaggtaatggtcgtactatgatagctacagcaaatgtt
aatggtggaactattggattattaactatgggttcagaaaacttcataccaggcacaagaccaattactgaatta
gcaatactaaacatgtctggtggattaattgaaagaattatcgtaggtaatgccaactcttcaaccataaacttt
actcctgggaagagatcaattgtaaaaacaataaatggtccagaacttccatatttagttaacatacaaaaaggt
gctatgacacaatggggcactaaaaatatgcccttttattggataacaagaaattttaatcttgtccggaactctg
attacctcaaatattcaactagctgattttatctataaccaatctatttgttgctaatggcggtacactagtacct
agaaaattaatacctgggaaccaacctgttatacagtttcttggaggtcctcaatcactcttagttatccatcaa
ccattaaaagtaaatttaagcttatcaccaaaacttattggaagtagcatggtgccacttgcttttgtctctcaa
tcttttttcatccaccagatctttttgttaaacaaactagaagtggtctcatttggagtgatcttgagtttgatcca
acaacatctatttggtatgttaataatatccaagcatctcaagattttttactctttctctattgctcgtgagact
actaactggctaagacaacaacatatatggactctacaaaaccgttcaagtaaacttttagacaacgaacattat
ggactatggatataatgttcaaggtggacatgaaagtcttgatacttctattggtagcaaagcaaaaatgccatgg
ataatggcaacagcaggatatgactatcttcaacaactaccaaggttagatatgaaagcccttttatggtcttgct
tttggtgcttctcaaaggtaaaagtaaatggtctagccgtcaactctacaaaaaatgatgctgagctaggtatggtt
agtggttatgtaggtcttatccataacaaaactgggctctatagtacattgaccttacaacttgcgtctagtaaa
ttacatactaattctacagggttctatagaaattttaaatggacagaaacaactccaacagaagcacttgaactt
ggatggaaatacactttcaacaacggtattaaaatgaatcctcgtggacaacttattttttgaacaaacatctaaa
caccattttgatttaggaattcaaaatgataaggctatattagataaaagccagttaataacaagttctcttggt
attaccgttgaatataagctaccagttaccacacctattaatctttatgctggtattgaaaggataaaaggtcag
tctggaaaactttgcaattagttcccagagccttcaaatgaagttcaagcatgacaatgatacaagtgtagttaga
```

-continued

SEQUENCES gcaacaataggtacaaatatattattgggagaacattttaatattcactgtgatatatttggagataaaggaaat
gataaaggcattggtgggcaagcaggatttacatacaaattttaa SEQ ID NO: 40
Name: Law 0033-OstA
Vector: pMAL-c2X
Length: 30
Type: Synthetic Nucleic Acid Sequence
Organism: Primer
5'-AACCTTAGATCTATTATCAACATCTCTGAA-3'

SEQ ID NO: 41
Name: Law 0033-OstA
Vector: pMAL-c2X
Length: 33
Type: Synthetic Nucleic Acid Sequence
Organism: Primer
5'-AACCTTAAGCTTTTATTCAAACAGACCAGGGAT-3'

SEQ ID NO: 42
Name: Law 0691-PAL
Vector: pET23a+
Length: 30
Type: Synthetic Nucleic Acid Sequence
Organism: Primer
5'-AACCTTGGATCCAAAAGCGTAGATGTAGAA-3'

SEQ ID NO: 43
Name: Law 0691-PAL
Vector: pET23a+
Length: 30
Type: Synthetic Nucleic Acid Sequence
Organism: Primer
5'-AACCTTAAGCTTTTTTGCGATGATGCGGAA-3'

SEQ ID NO: 44
Name: Law 0691-PAL
Vector: pMAL-c2X
Length: 30
Type: Synthetic Nucleic Acid Sequence
Organism: Primer
5'-AACCTTGGATCCAAAAGCGTAGATGTAGAA-3'

SEQ ID NO: 45
Name: Law 0691-PAL
Vector: pMAL-c2X
Length: 33
Type: Synthetic Nucleic Acid Sequence
Organism: Primer
5'-AACCTTAAGCTTTTATTTTGCGATGATGCGGAA-3'

SEQ ID NO: 46
Name: Law0995-OPRM
Vector: pMAL-c2X
Length: 30
Type: Synthetic Nucleic Acid Sequence
Organism: Primer
5'-AAACTAGGATCCTTCGCTCCAGATTACAAC-3'

SEQ ID NO: 47
Name: Law0995-OPRM
Vector: pMAL-c2X
Length: 33
Type: Synthetic Nucleic Acid Sequence
Organism: Primer
5'-AACCAAAAGCTTTTATTCCCAGGAGCCACCCAG-3'

SEQ ID NO: 48
Name: Law C046-SLH
Vector: pMAL-c2X
Length: 30
Type: Synthetic Nucleic Acid Sequence
Organism: Primer
5'-AACCTTAGATCTAAAAAGGAAGTTAAAATC-3'

SEQ ID NO: 49
Name: Law C046-SLH

SEQUENCES

Vector: pMAL-c2X
Length: 33
Type: Synthetic Nucleic Acid Sequence
Organism: Primer
5'-AACCTTAAGCTTTTAGTACACATAACGGATGGT-3'

SEQ ID NO: 50
Name: Law00147-SlyB
Vector: pMAL-c2X
Length: 30
Type: Synthetic Nucleic Acid Sequence
Organism: Primer
5'-AACCTTAGATCTGGTAAACAGATCCGTAGC-3'

SEQ ID NO: 51
Name: Law00147-SlyB
Vector: pMAL-c2X
Length: 33
Type: Synthetic Nucleic Acid Sequence
Organism: Primer
5'-AACCTTAAGCTTTCAGATAGAGCTGACGCGTGC-3'

SEQ ID NO: 52
Name: Law 0050-AsmA
Vector: pMAL-c2X
Length: 30
Type: Synthetic Nucleic Acid Sequence
Organism: Primer
5'-AACCTTAGATCTATCACGTTCTACTTCATC-3'

SEQ ID NO: 53
Name: Law 0050-AsmA
Vector: pMAL-c2X
Length: 33
Type: Synthetic Nucleic Acid Sequence
Organism: Primer
5'-AACCTTTCTAGACGGCAGCAGCAGTTTCAGCGG-3'

SEQ ID NO: 54
Name: Law 0065-LoIA
Vector: pMAL-c2X
Length: 30
Type: Synthetic Nucleic Acid Sequence
Organism: Primer
5'-AACCTTAGATCTGAAAGCATCCCGATTGTA-3'

SEQ ID NO: 55
Name: Law 0065-LoIA
Vector: pMAL-c2X
Length: 33
Type: Synthetic Nucleic Acid Sequence
Organism: Primer
5'-AACCTTAAGCTTTTAATTGAACAGTGGGCGCTC-3'

SEQ ID NO: 56
Name: Law 0043-PtfH
Vector: pMAL-c2X
Length: 30
Type: Synthetic Nucleic Acid Sequence
Organism: Primer
5'-AACCTTAGATCTTCTAGCAGCTCTAAGGTT-3'

SEQ ID NO: 57
Name: Law 0043-PtfH
Vector: pMAL-c2X
Length: 34
Type: Synthetic Nucleic Acid Sequence
Organism: Primer
5'-AACCTTAAGCTTAGATTTCAGAGGACAGGTCAGA-3'

SEQ ID NO: 58
Name: Law 0649-OmpB
Vector: pMAL-c2X
Length: 30
Type: Synthetic Nucleic Acid Sequence
Organism: Primer
5'-AACCTTAGATCTGTAGAACACTTCGCAAAT-3'

SEQUENCES -continued

SEQ ID NO: 59
Name: Law 0649-OmpB
Vector: pMAL-c2X
Length: 33
Type: Synthetic Nucleic Acid Sequence
Organism: Primer
5'-AACCTTAAGCTTTCAGAAGCGGTAGGTAGCACC-3'

SEQ ID NO: 60
Name: Law 1082-FeoA
Vector: pMAL-c2X
Length: 30
Type: Synthetic Nucleic Acid Sequence
Organism: Primer
5'-AACCTTAGATCTATGTCTGCCGTTGTTGAT-3'

SEQ ID NO: 61
Name: Law 1082-FeoA
Vector: pMAL-c2X
Length: 33
Type: Synthetic Nucleic Acid Sequence
Organism: Primer
5'-AACCTTAAGCTTTTAAGAAATCGGAGACACCAT-3'

SEQ ID NO: 62
Name: LawB004-Fluf
Vector: pMAL-c2X
Length: 30
Type: Synthetic Nucleic Acid Sequence
Organism: Primer
5'-AACCTTGGATCCAAACAAAAGATCTACGCG-3'

SEQ ID NO: 63
Name: LawB004-Fluf
Vector: pMAL-c2X
Length: 33
Type: Synthetic Nucleic Acid Sequence
Organism: Primer
5'-AACCTTAAGCTTTTAGAATTTGTAGGTGAAACC-3'

SEQ ID NO: 64
Name: Law 1153-OmpA
Vector: pET23a+
Length: 33
Type: Synthetic Nucleic Acid Sequence
Organism: Primer
5'-AACCTTAGATCTGGTAACACTAATCGTGCTACT-3'

SEQ ID NO: 65
Name: Law 1153-OmpA
Vector: pET23a+
Length: 30
Type: Synthetic Nucleic Acid Sequence
Organism: Primer
5'-AACCTTAAGCTTCTGGATGTTGTTTTCATC-3'

SEQ ID NO: 66
Name: N-terminal HIS tag adaptor
Vector: pUEX2-M3
Length: 60
Type: Synthetic Nucleic Acid Sequence
Organism: Primer
5'-AATTCATCATCATCATCATCATAGCAGCGGCATCGAAGGCCGCGGCCGCTTAATTAATAG-3'

SEQ ID NO: 67
Name: N-terminal HIS tag adaptor
Vector: pUEX2-M3
Length: 60
Type: Synthetic Nucleic Acid Sequence
Organism: Primer
5'-AATTCTATTAATTAAGCGGCCGCGGCCTTCGATGCCGCTGCTATGATGATGATGATGATG-3'

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An immunogenic composition consisting of a first polypeptide having an amino acid sequence at least 90% identical to a sequence selected from the group consisting of SEQ ID NOs: 1, 2, 3, 5, 7, 9, 10; and 11; a second polypeptide having an amino acid sequence at least 90% identical to a sequence selected from the group consisting of SEQ ID NOs: 12 and 13; and one or more pharmaceutically acceptable components selected from the group consisting of an appropriate pharmaceutical carrier and a pharmaceutically acceptable adjuvant.

2. The immunogenic composition of claim 1 wherein the adjuvant is selected from the group consisting of aluminum hydroxide, aluminum phosphate, the combination of oil, water and aluminum hydroxide, Quil A, Quil A plus cholesterol, and Immune Stimulating Complex (ISCOM).

3. The immunogenic composition according to claim 1 wherein the first polypeptide has an amino acid sequence at least 90% identical to SEQ ID NO: 9.

4. The immunogenic composition according to claim 3 wherein the second polypeptide has an amino acid sequence at least 90% identical to SEQ ID NO: 13.

5. An immunogenic composition consisting of a first polypeptide having an amino acid sequence at least 90% identical to a sequence selected from the group consisting of SEQ ID NOs: 1, 2, 3, 5, 7, 9, 10, and 11; a second polypeptide having an amino acid sequence at least 90% identical to a sequence selected from the group consisting of SEQ ID NOs: 12 and 13; one or more antigenic components of *Mycoplasma hyopneumoniae Erysipelas* spp. *salmonella, Haemophilus parasuis, Clostridium* spp. *Streptococcus suis, Brachyspira* spp. *Bordetella, Pasteurella, Escherichia coli* (*E. coli*), Coronavirus, Parvovirus, porcine reproductive and respiratory syndrome virus (PRRS), porcine circovirus (PCV), or swine influenza virus (SIV); and one or more pharmaceutically acceptable components selected from the group consisting of an appropriate pharmaceutical carrier and a pharmaceutically acceptable adjuvant.

6. The immunogenic composition of claim 5 wherein the adjuvant is selected from the group consisting of aluminum hydroxide, aluminum phosphate, the combination of oil, water and aluminum hydroxide, Quil A, Quil A plus cholesterol, and Immune Stimulating Complex (ISCOM).

7. The immunogenic composition according to claim 6 wherein the first polypeptide has an amino acid sequence at least 90% identical to SEQ ID NO: 9.

8. The immunogenic composition according to claim 7 wherein the second polypeptide has an amino acid sequence at least 90% identical to SEQ ID NO: 13.

9. The immunogenic composition according to claim 5 wherein the first polypeptide has an amino acid sequence at least 90% identical to SEQ ID NO: 9.

10. The immunogenic composition according to claim 9 wherein the second polypeptide has an amino acid sequence at least 90% identical to SEQ ID NO: 13.

11. The immunogenic composition according to claim 2 wherein the first polypeptide has an amino acid sequence at least 90% identical to SEQ ID NO: 9.

12. The immunogenic composition according to claim 11 wherein the second polypeptide has an amino acid sequence at least 90% identical to SEQ ID NO: 13.

13. An immunogenic composition consisting of one or more polypeptides having an amino acid sequence at least 90% identical to a sequence selected from the group consisting of SEQ ID NOs: 1, 2, 3, 5, 7, 9, 10, and 11; one or more polypeptides having an amino acid sequence at least 90% identical to a sequence selected from the group consisting of SEQ ID NOs: 12 and 13; and one or more pharmaceutically acceptable components selected from the group consisting of an appropriate pharmaceutical carrier and a pharmaceutically acceptable adjuvant.

14. The immunogenic composition of claim 13 wherein the adjuvant is selected from the group consisting of aluminum hydroxide, aluminum phosphate, the combination of oil, water and aluminum hydroxide, Quil A, Quil A plus cholesterol, and Immune Stimulating Complex (ISCOM).

15. An immunogenic composition consisting of one or more polypeptides having an amino acid sequence at least 90% identical to a sequence selected from the group consisting of SEQ ID NOs: 1, 2, 3, 5, 7, 9, 10, and 11; one or more polypeptides having an amino acid sequence at least 90% identical to a sequence selected from the group consisting of SEQ ID NOs: 12 and 13; and one or more antigenic components of *Mycoplasma hyopneumoniae Erysipelas* spp, *salmonella, Haemophilus parasuis, Clostridium* spp. *Streptococcus suis, Brachyspira* spp. *Bordetella, Pasteurella, Escherichia coli* (*E. coli*), Coronavirus, Parvovirus, porcine reproductive and respiratory syndrome virus (PRRS), porcine circovirus (PCV), or swine influenza virus (SIV); and one or more pharmaceutically acceptable components selected from the group consisting of an appropriate pharmaceutical carrier and a pharmaceutically acceptable adjuvant.

16. The immunogenic composition of claim 15 wherein the adjuvant is selected from the group consisting of aluminum hydroxide, aluminum phosphate, the combination of oil, water and aluminum hydroxide, Quil A, Quil A plus cholesterol, and Immune Stimulating Complex (ISCOM).

\* \* \* \* \*